(12) United States Patent
Smith et al.

(10) Patent No.: US 9,045,505 B2
(45) Date of Patent: Jun. 2, 2015

(54) NITRIC OXIDE DONORS

(75) Inventors: Robin Andrew James Smith, Dunedin (NZ); Michael Patrick Murphy, Highfields (GB)

(73) Assignees: University of Otago (NZ); Medical Research Council (GB)

(*) Notice: Subject to any disclaimer, the term of this patent is extended or adjusted under 35 U.S.C. 154(b) by 505 days.

(21) Appl. No.: 12/732,909

(22) Filed: Mar. 26, 2010

(65) Prior Publication Data
US 2010/0240615 A1 Sep. 23, 2010

Related U.S. Application Data

(63) Continuation-in-part of application No. 12/412,930, filed on Mar. 27, 2009, now abandoned, which is a continuation-in-part of application No. PCT/NZ2007/000282, filed on Sep. 26, 2007.

(60) Provisional application No. 60/847,686, filed on Sep. 28, 2006.

(51) Int. Cl.
| | | |
|---|---|---|
| *A61K 31/66* | (2006.01) | |
| *C07F 9/54* | (2006.01) | |
| *A61K 31/662* | (2006.01) | |
| *A61K 47/48* | (2006.01) | |

(52) U.S. Cl.
CPC .............. *C07F 9/5407* (2013.01); *A61K 31/662* (2013.01); *A61K 47/48023* (2013.01); *C07F 9/5456* (2013.01)

(58) Field of Classification Search
CPC ................ A61K 31/66; A61K 31/662; A61K 47/48023; C07F 9/5407; C07F 9/5456; C07F 9/2483; C07F 9/4488; A01N 57/30; A01N 57/26; A01N 57/28
USPC ................ 514/183, 509, 116; 564/15; 568/11
See application file for complete search history.

(56) References Cited

U.S. PATENT DOCUMENTS

| | | |
|---|---|---|
| 6,331,532 B1 | 12/2001 | Murphy et al. |
| 6,984,636 B2 | 1/2006 | Murphy et al. |
| 7,109,189 B2 | 9/2006 | Murphy et al. |
| 7,232,809 B2 | 6/2007 | Murphy et al. |
| 2002/0005234 A1 | 1/2002 | Vandeputte et al. |
| 2004/0038947 A1 | 2/2004 | Wink et al. |
| 2004/0039063 A1 | 2/2004 | Wink et al. |
| 2004/0106579 A1 | 6/2004 | Murphy et al. |
| 2005/0245487 A1 | 11/2005 | Murphy et al. |
| 2006/0122267 A1 | 6/2006 | Brookes et al. |
| 2006/0229278 A1 | 10/2006 | Taylor et al. |
| 2007/0161609 A1 | 7/2007 | Buck et al. |
| 2007/0238709 A1 | 10/2007 | Murphy et al. |
| 2008/0032940 A1 | 2/2008 | Kalyanaraman et al. |
| 2008/0108545 A1 | 5/2008 | Eccles et al. |
| 2008/0161267 A1 | 7/2008 | Taylor et al. |
| 2008/0176929 A1 | 7/2008 | Skuulachev |
| 2008/0275005 A1 | 11/2008 | Murphy et al. |

FOREIGN PATENT DOCUMENTS

| | | |
|---|---|---|
| EP | 0 412 699 | 2/1991 |
| WO | WO 99/26582 | 6/1999 |
| WO | WO 00/12075 | 3/2000 |
| WO | WO 2007/016136 | 2/2007 |
| WO | WO 2007/076322 | 7/2007 |
| WO | WO 2007/123818 | 11/2007 |
| WO | WO 2008/039085 | 4/2008 |

OTHER PUBLICATIONS

Murphy, M. P., Trends Biotechnol., 1997, 15(8), 326-330.*
Soulère et al, Tetrahedron, 2001, 57, 7173-7180.*
Moynihan et al, J. Chem. Soc. Perkin Trans.1, 1994, 797-805.*
Brown et al. "Nanomolar concentrations of nitric oxide reversibly inhibit synaptosomal respiration by competigin with oxygen at cytochrome oxidase." *FEBS Letters*. vol. 356. 1994. pp. 295-298.
Burwell et al. "Direct evidence for S-nitrosation of mitochondrial complex I." *Biochem. J.* vol. 394. 2006. pp. 627-634.
Cleeter et al. "Reversible inhibition of cytochrome c oxidase, the terminal enzyme of the mitochondrial respiratory chain, by nitric oxide." *FEBS Letters*. vol. 345. 1994. pp. 50-54.
Costa et al. "Interactions of Mitochondrial Thiols with Nitric Oxide." *Antioxidants & Redox Signaling*. vol. 5. No. 3. 2003. pp. 291-306.
Dahm et al. "Persistent S-Nitrosation of Complex I and Other Mitochondrial Membrane Proteins by S-Nitrosothiols but Not Nitric Oxide or Peroxynitrite." *J. of Biol. Chem.* vol. 281. No. 15. 2006. pp. 10056-10065.
Feelisch et al. "Concomitan S-, N-, and heme-nitros (yl)ation in biological tissues and fluids: implications for the fat of NO in vivo." *The FASEB Journal*. vol. 17. 2002. pp. 1775-1785.
Galkin et al. "S-Nitrosation of Michondrial Complex I Depends on Its Structural Conformation." *J. of Biol. Chem.* vol. 282. No. 52. 2007. pp. 37448-37453.
Hagen et al. "Redistribution of Intracellular Oxygen in Hypoxia Nitric Oxide: Effect on HIF1α" *Science*. vol. 302. 2003. pp. 1975-1978.
Hogg. "The Biochemistry and Physiology of S-Nitrosothiols." *Annu. Rev. Pharmacol. Toxicol.* vol. 42. 2002. pp. 585-600.
Moncada et al. "Does nitric oxide modulate mitochondrial energy generation and apoptosis?" *Nature*. vol. 3. 2002. pp. 214-216.
Murphy et al. "Targeting Antioxidants to Mitochondria by Conjugation to Lipophilic Cations." *Annu. Rev. Pharmacol. Toxicol.* vol. 47. 2007. pp. 629-656.
Murphy. "Targeting lipophilic cations to mitochondria." *Biochimica et Biophysica Acta*. vol. 1777. 2008. pp. 1028-1031.
Nadtochiy et al. "Cardioprotection and mitochondrial S-nitrosation: Effects of S-nitroso-2-mercaptopropionyl glycine (SNO-MPG) in cardiac ischemia—reperfusion injury." *J. of Molecular and Cellular Cardiology*. vol. 42. 2007. pp. 812-825.

(Continued)

*Primary Examiner* — Jason Sims
*Assistant Examiner* — Ibrahim D Bori
(74) *Attorney, Agent, or Firm* — Thomas G. Peterson; Bradley Arant Boult Cummings LLP

(57) ABSTRACT

The invention relates to novel NO donors which are targeted to the mitochondria. The NO donor compounds of the invention allow NO to be selectively provided to the mitochondria.

11 Claims, 19 Drawing Sheets

(56) References Cited

OTHER PUBLICATIONS

Ridnour et al. "Antioxidant Properties of Nitric Oxide in Celluar Physiological and Pathophysilogical Mechanisms. The Implications of Biological Balance between NO and Oxidative Stress." *Curr. Med. Chem.—Anti-Inflammatory & Anti-Allergy Agents*. vol. 3. 2004. pp. 181-188.

Schweizer et al. "Nitric Oxide Potently and Reversibly Deenergizes Mitochondria At Low Oxygen Tension." *BioChem. BioPhys. Research Communications*. vol. 204. No. 1. 1994. pp. 169-175.

Seel et al. "The Reaction of Polysulfides with Nitrogen Monoxide in Non-Aqueous Solvents—Nitrosodisulfides." *Zeitzchrift fuer. Naturforschung., Teil B: Anorganische Chemie, Organische Chemi*, vol. 40B. No. 6. 1985.. pp. 762-764. (Abstract provided).

Shiva et al. Nitrite augments tolerance to ischemia/reperfusion injury via the modulation of mitochondrial electron transfer. *JEM*. vol. 204. No. 9. 2007. pp. 2089-2102.

Smith et al. "Selective targeting of an antioxidant to mitochondria." *Eur. J. Biochem.* vol. 263. 1999. pp. 709-716.

International Search Report and Written Opinion for International Application No. PCT/NZ2010/000059, 2010.

Clancy et al. "Preparation and Properties of S-Nitroso-L-Cysteine Ethyl Ester, an Intracellular Nitrosating Agent." *J. Med. Chem*. vol. 44. 2001. pp. 2035-2038.

Bertinaria et al. "Synthesis and Pharmacological Characterization of New $H_2$-Antagonists Containing NO-Donor Moieties, Endowed with Mixed Antiscretory and Clastroprotective Activities." *Helvetica Chimica Acta*. vol. 83. 2000. pp. 287-299.

Roy et al. "New Thinitries: Synthesis, Stability, and Nitric Oxide Generation." *J. Org. Chem*. vol. 59. pp. 7019-7026, 1994.

\* cited by examiner

NITRIC OXIDE DONORS

This application is a Continuation-in-Part of U.S. Ser. No. 12/412,930, filed 27 Mar. 2009, which is a Continuation-in-Part of PCT/NZ2007/000282, filed 26 Sep. 2007, which claims benefit of U.S. Ser. No. 60/847,686, filed 28 Sep. 2006 and which applications are incorporated herein by reference. To the extent appropriate, a claim of priority is made to each of the above disclosed applications.

TECHNICAL FIELD

The invention relates to nitric oxide donor compounds and uses thereof, in particular nitric oxide donor compounds comprising a thionitrite conjugated to triphenylphosphonium cation.

BACKGROUND OF INVENTION

The endogenous formation of nitric oxide (NO) plays a key role in many bio-regulatory systems including immune stimulation, platelet inhibition, neurotransmission, and smooth muscle relaxation (Wang, P. G., Xian, M., Tang, X., Wu, X., Wen, Z., Cai, T., Janczuk, A. *J. Chem. Rev.* 2002, 102, 1091-1134). Due to the instability and inconvenience of handling aqueous solutions of NO, there is increasing interest in compounds capable of generating NO in situ, i.e., NO donors.

All nitrogen-oxygen bonded compounds have the potential to decompose, be oxidized, or be reduced to produce reactive nitrogen species. Accordingly, a diverse range of NO donors has been developed including organic nitrates and nitrites, metal-NO complexes, N-nitrosamines, thionitrites, furoxans and benzofuroxans, oximes and N-hydroxyguanidines. However, the NO donors developed to date are poorly taken up by cells and are not targeted to particular compartments of the cell. Therefore, the presently known NO donors mainly produce NO in the circulation and thus expose a range of NO receptors to NO.

S-Nitrosylation (also referred to as S-nitrosation) is the post-translational addition of a nitrosyl group to a protein. In addition to releasing free NO, NO donors can also transfer a nitrosonium group to a protein thiol to form an S-nitrosylated product. The modulation of S-nitrosylation may be involved in regulating a number of pathways important in cell metabolism (*Nature Reviews:Molecular Cell Biology*, 2005, 6:2, pp 150-166).

Recently, it has been shown that cytochrome c oxidase (complex IV of the mitochondrial respiratory chain) is reversibly inhibited by NO (Brown, G. C. and Cooper, C. E. *FEBS Lett.* 1994, 356, 295-298; Cleeter, M. J. W., Cooper, J. M., Darley-Usmer, V. M., Moncada, S. and Schapira, A. H. V. *FEBS Lett.* 1994, 345, 50-54; Schweizer, M. and Richter, C. *Biochem. Biophys. Res. Commum.* 1994, 204, 169-175).

This may be a physiologically relevant mechanism to limit oxygen consumption, mitochondrial ROS (reactive oxygen species) production, apoptosis and mitochondrial biogenesis and morphology.

Transfer of the nitrosonium group to protein thiols may also be involved in regulating mitochondrial function, for example at complex I (Dahm, C. C., Moore, K., Murphy, M. P., *J. Biol. Chem.* 2006, 281, pp 10056-10065). S-Nitrosylation of particular mitochondrial thiol proteins such as complex I may play a protective role in conditions such as ischaemia-reperfusion injury (*Journal of Molecular and Cellular Cardiology*, 2007, 42:4, pp 812-825).

In order to investigate this function of NO, it would be useful to have a NO donor compound that selectively released NO in the mitochondria. In addition, a number of medical conditions are influenced by the selective, reversible inhibition of mitochondria. Therefore a mitochondrially targeted NO donor would have potential as a therapeutic agent.

It is therefore an object of the invention to provide a targeted NO donor compound, or at least to provide the public with a useful choice.

SUMMARY OF INVENTION

In one aspect the invention provides a compound comprising a lipophilic cation linked by a linker group to a thionitrite moiety;
and a pharmaceutically acceptable anion;
wherein the lipophilic cation is capable of mitochondrially targeting the thionitrite moiety.

In one embodiment the lipophilic cation is a substituted or unsubstituted triphenylphosphonium cation. In one embodiment, a substituted triphenylphosphonium cation is substituted with one or more alkyl groups, preferably methyl or ethyl groups.

In one embodiment the linker group is selected from the group comprising
(a) $(C_1-C_{30})$ alkylene,
(b) $(C_1-C_x)$ alkylene-NR—$(C_1-C_y)$ alkylene, wherein R is H, alkyl, or aryl,
(c) $(C_1-C_x)$ alkylene-NR—C(=O)—$(C_1-C_y)$ alkylene, wherein R is H, alkyl, or aryl,
(d) $(C_1-C_x)$ alkylene-C(=O)—NR—$(C_1-C_y)$ alkylene, wherein R is H, alkyl, or aryl,
(e) $(C_1-C_x)$ alkylene-O—$(C_1-C_y)$ alkylene,
(f) $(C_1-C_x)$ alkylene-O—C(=O)—$(C_1-C_y)$ alkylene,
(g) $(C_1-C_x)$ alkylene-S—$(C_1-C_y)$ alkylene, and
(h) $(C_1-C_x)$ alkylene-aryl-$(C_1-C_y)$ alkylene,
wherein $x+y=30$ and wherein the alkylene group is optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the substituent groups of adjacent carbon atoms in the linker group can be taken together with the carbon atoms to which they are attached to form a carbocycle or a heterocycle.

In another aspect the invention provides a compound of formula (I)

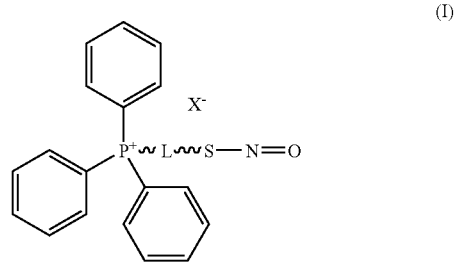

(I)

wherein ~L~ is a linker group and X is an optional anion.

In another aspect the invention provides a compound of formula (I)

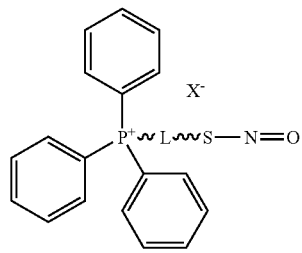

(I)

wherein ~L~ is a linker group and X is an optional anion where the linker group is selected from the group comprising (a) $(C_1-C_{30})$ alkylene,
(b) $(C_1-C_x)$ alkylene-NR—$(C_1-C_y)$ alkylene, wherein R is H, alkyl, or aryl,
(c) $(C_1-C_x)$ alkylene-NR—C(=O)—$(C_1-C_y)$ alkylene, wherein R is H, alkyl, or aryl,
(d) $(C_1-C_x)$ alkylene-C(=O)—NR—$(C_1-C_y)$ alkylene, wherein R is H, alkyl, or aryl,
(e) $(C_1-C_x)$ alkylene-O—$(C_1-C_y)$ alkylene,
(f) $(C_1-C_x)$ alkylene-O—C(=O)—$(C_1-C_y)$ alkylene,
(g) $(C1-C_x)$ alkylene-S—$(C_1-C_y)$ alkylene, and
(h) $(C_1-C_x)$ alkylene-aryl-$(C_1-C_y)$ alkylene, wherein x+y=30 and wherein the alkylene group is optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the substituent groups of adjacent carbon atoms in the linker group can be taken together with the carbon atoms to which they are attached to form a carbocycle or a heterocycle.

In another aspect the invention provides a compound of formula (II)

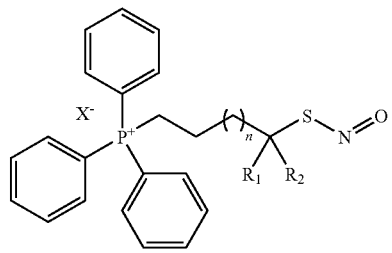

(II)

wherein n is from 0 to 27, X is an optional anion and $R_1$ and $R_2$ are independently selected from the group comprising hydrogen, alkyl and aryl.

In another aspect the invention provides a compound of formula (III)

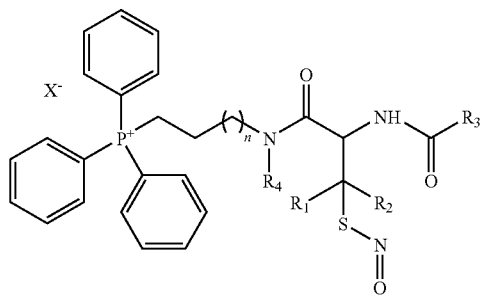

(III)

wherein n is from 0 to 27, X is an optional anion and $R_1$, $R_2$, $R_3$ and $R_4$ are independently selected from the group comprising hydrogen, alkyl and aryl.

In another aspect the invention provides a compound of formula (IV)

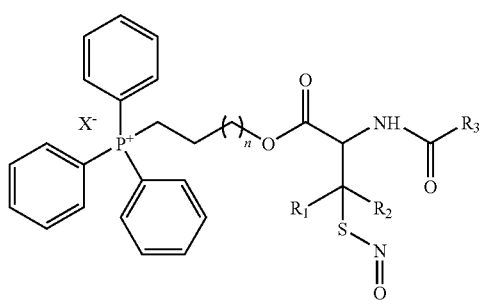

(IV)

wherein n is from 0 to 27, X is an optional anion and $R_1$, $R_2$ and $R_3$ are independently selected from the group comprising hydrogen, alkyl and aryl.

In another aspect the invention provides a compound of formula (V)

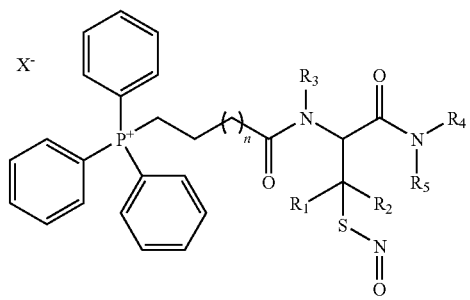

(V)

wherein n is from 0 to 24, X is an optional anion and $R_1$, $R_2$, $R_3$, $R_4$ and $R_5$ are independently selected from the group comprising hydrogen, alkyl and aryl.

In another aspect the invention provides a compound of formula (VI)

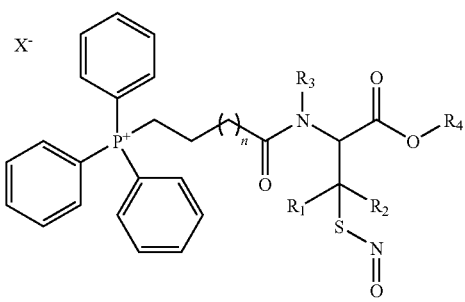

(VI)

wherein n is from 0 to 24, X is an optional anion and $R_1$, $R_2$, $R_3$, and $R_4$ are independently selected from the group comprising hydrogen, alkyl and aryl.

In another aspect the invention provides a pharmaceutical composition comprising a therapeutically effective amount of a compound of the invention in combination with one or more pharmaceutically acceptable excipients, carriers or diluents.

In another aspect the invention provides a method of treating Alzheimer's disease in a subject in need thereof, said method comprising administering to the subject a therapeutically effective amount of a compound of the invention or a pharmaceutical composition comprising same.

In another aspect the invention provides a method of treating Parkinson's disease in a subject in need thereof, said method comprising administering to the subject a therapeutically effective amount of a compound of the invention or a pharmaceutical composition comprising same.

In another aspect the invention provides a method of treating a disease or disorder selected from the group comprising cancer, neoplasms, tumor growth, metastatsis, angina, stroke, myocardial infarction and ischaemia-reperfusion injury in a subject in need thereof, said method comprising administering to the subject a therapeutically effective amount of a compound of the invention or a pharmaceutical composition comprising same.

In another aspect the invention provides a method of inhibiting angiogenesis in a subject in need thereof, said method comprising administering to the subject a therapeutically effective amount of a compound of the invention or a pharmaceutical composition comprising same In another aspect the invention provides a method for generating NO in the mitochondria of a subject comprising administering to the subject, a therapeutically effective amount of a compound of the invention or a pharmaceutical composition comprising same In another aspect the invention provides a method for inhibiting cytochrome oxidase in the mitochondria of a subject comprising administering to the subject, a therapeutically effective amount of a compound of the invention or a pharmaceutical composition comprising same.

In another aspect the invention provides a method for S-nitrosylating proteins in the mitochondria of a subject comprising administering to the subject, a therapeutically effective amount of a compound of the invention or a pharmaceutical composition comprising same.

BRIEF DESCRIPTION OF THE DRAWINGS

Preferred features of the invention will be described, by way of example only, with reference to the following figures.

DETAILED DESCRIPTION OF THE INVENTION

1. Definitions

Figure 1:
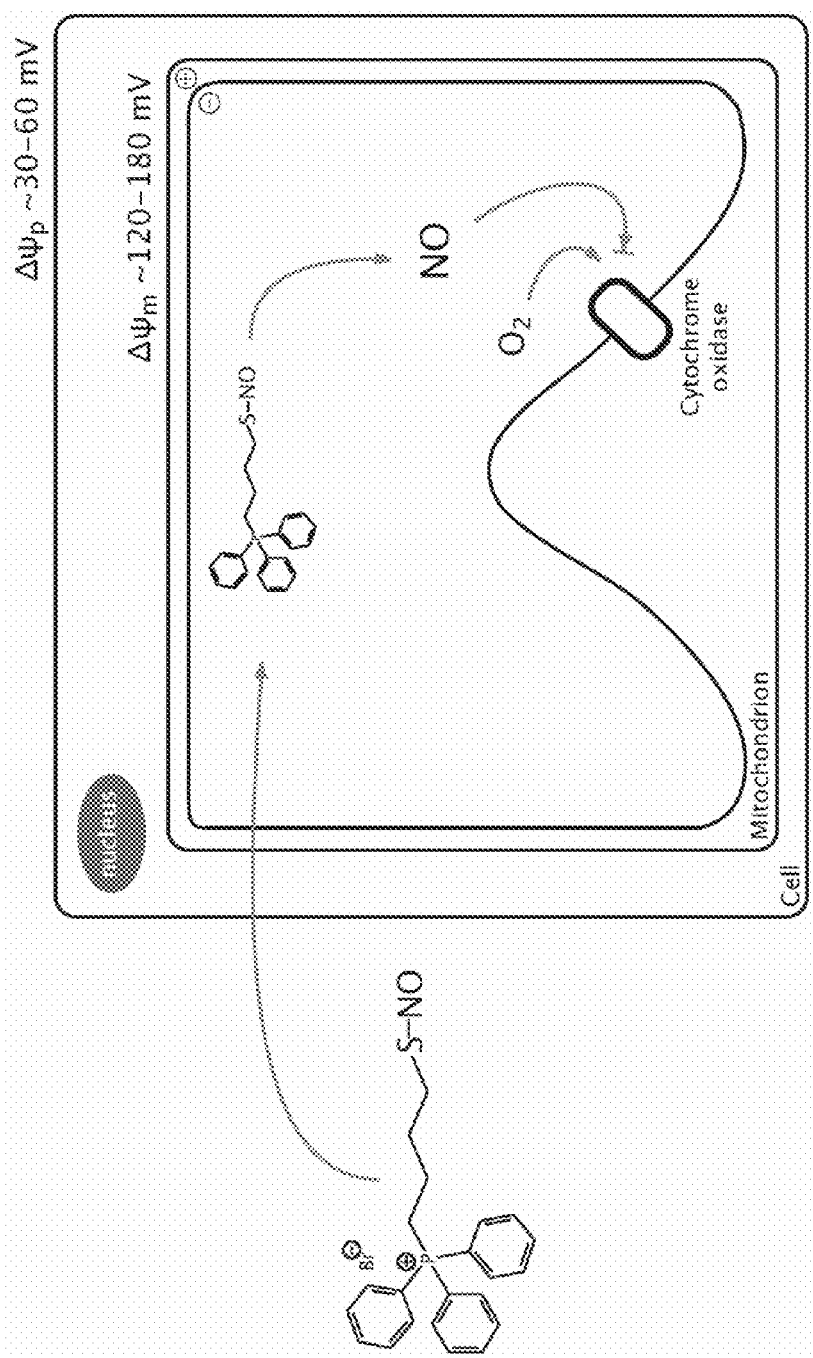
FIG. 1 is a schematic diagram showing the effects of a compound of the invention (MitoSNO) when delivered to a cell. MitoSNO accumulates within the mitochondria and releases NO, inhibiting cytochrome oxidase by competing with oxygen.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "cycloalkyl" and "alkylene." The term "alkylene" by itself or as part of another substituent means a divalent radical derived from an alkane, as exemplified by —$CH_2CH_2CH_2CH_2$—.

Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "cycloalkyl" by itself or in combination with other terms, represent, unless otherwise stated, a cyclic versions of "alkyl". Examples of cycloalkyl include cyclopentyl, cyclohexyl, 1-cyclohexenyl, 3-cyclohexenyl, cycloheptyl, and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl 4-pyrimidyl, 2-benzothiazolyl, 5-benzothiazolyl, 2-benzoxazolyl, 5-benzoxazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. Substituents for each of the above noted aryl ring systems are selected from the group of acceptable substituents described herein.

The term "alkoxy", as used herein, means an O-alkyl group wherein "alkyl" is defined above.

The term "sulfonyl" refers to a radical —$S(O)_2R$ where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

The term "sulfinyl" refers to a radical —$S(O)R$ where R is an alkyl, substituted alkyl, substituted cycloalkyl, substituted heterocycloalkyl, substituted aryl, or substituted heteroaryl group as defined herein. Representative examples include, but are not limited to, methylsulfinyl, ethylsulfinyl, propylsulfinyl, butylsulfinyl, and the like.

The term "aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenymethylene, 2-phenethyl and naphthalenylmethyl. The bond to the parent moiety is through the alkyl.

The term "pharmaceutically acceptable" as used herein refers to compounds, ingredients, materials, compositions, dosage forms and the like, which are within the scope of sound medical judgment, suitable for use in contact with the tissues of the subject in question (e.g. human) without excessive toxicity, irritation, allergic response, or other problem or complication, commensurate with a reasonable benefit/risk ratio. Each carrier, diluent, exipient, etc., must also be "acceptable" in the sense of being compatible with the other ingredients of the formulation.

The term "subject" as used herein refers to a human or non-human mammal Examples of non-human mammals include livestock animals such as sheep, horses, cows, pigs, goats, rabbits, deer, ostriches and emus; and companion animals such as cats, dogs, rodents, and horses.

The term "treatment" as used herein in the context of treating a condition, pertains generally to treatment and therapy, whether of human or animal, in which some desired therapeutic effect is achieved, for example, the inhibition of progress of the condition, and includes a reduction in the rate of progress, a halt in the rate of progress, amelioration of the condition, and cure of the condition. Treatment as a prophylactic measure (i.e., prophylaxis) is also included.

"Treatment" also includes combination treatments and therapies, in which two or more treatments or therapies are combined, for example, sequentially or simultaneously. For example, a therapeutically effective amount of a compound of the invention could be combined with or used in conjunction with radiation therapy or chemotherapy in the treatment of cancer.

The term "therapeutically-effective amount" as used herein, pertains to that amount of an active compound, or a material, composition or dosage form comprising an active compound, which is effective for producing some desired therapeutic or prophylactic effect, commensurate with a reasonable benefit/risk ratio.

As used herein the term "comprising" means "consisting at least in part of". When interpreting each statement in this specification that includes the term "comprising", features other than that or those prefaced by the term may also be present. Related terms such as "comprise" and "comprises" are to be interpreted in the same manner.

The statements wherein, for example, $R^1$, $R^2$ and $R^3$, are said to be independently selected from a group of substituents, mean that $R^{1'}$ $R^2$ and $R^3$ are independently selected, but also that where an R, $R^1$, $R^2$ and $R^3$ variable occurs more than once in a molecule, each occurrence is independently selected (e.g., if R is —$OR^6$ wherein $R^6$ is hydrogen, $R^2$ can be —$OR^6$ wherein $R^6$ is lower alkyl). Those skilled in the art will recognize that the size and nature of the substituent(s) will affect the number of substituents that can be present.

Some compounds of the invention have at least one asymmetrical carbon atom and therefore all isomers, including enantiomers, stereoisomers, rotamers, tautomers and racemates of the compounds are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the invention. Isomers may also include geometric isomers, e.g., when a double bond is present.

Those skilled in the art will appreciate that for some of the compounds of the invention, one isomer may show greater pharmacological activity than other isomers.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

2. Compounds of the Invention

Thionitrites (RSNO) are an important class of NO donor molecules. They are produced in biological systems in response to NO and are believed to play an important role in storing, transporting and releasing NO under physiological conditions. It has now been shown that conjugation of a thionitrite-containing molecule to a lipophilic cation such as a triphenylphosphonium cation produces a compound that rapidly enters the cell through direct passage through the plasma membrane.

These compounds enable production of NO in the thiol reducing environment within the cell. Therefore, use of the lipophilic cation compounds of the invention may enable more efficient and regulated intracellular production of NO. Intracellular production of NO may have applications for regulating signaling pathways dependent on NO such as vasodilation, regulating activity of intracellular signaling pathways that impact on cell function and on the regulation of mitochondrial biogenesis.

In addition, NO itself may act as an antioxidant, therefore the intracellular production of NO may to protect against oxidative damage in pathologies (*Current Medicinal Chemistry: Anti-inflammatory and Anti-Allergy agents*, 2004, 3:3, pp 181-188).

The compounds of the invention not only release free NO but can also transfer a nitrosonium group to a protein thiol, thereby forming a S-nitrosylated (S-nitrosated) product. Therefore, the compounds of the invention allow for manipulation of both free NO and the S-nitrosylation (S-nitrosation) status of cells, in order to manipulate and modify the cell's metabolism and function.

In addition to rapidly causing NO release inside the cell, conjugation to a lipophilic cation enables the NO donor to accumulate within the mitochondria. Therefore, the compounds of the invention can selectively release NO in the mitochondria and/or can S-nitrosylate proteins in the mitochondria.

Mitochondria have a substantial membrane potential of up to 180 mV across their inner membrane (negative inside). Because of the potential, membrane permeant lipophilic cations such as the triphenylphosphonium cation accumulate several-hundred fold within the mitochondrial matix. This is illustrated in FIG. 1 which shows the effect of a compound of the invention (MitoSNO) when delivered to a whole cell.

MitoSNO is taken up by cells, courtesy of the plasma membrane potential ($\Delta\psi p$), and further accumulates in the mitochondrial matrix, driven by the mitochondrial membrane potential ($\Delta\psi m$). Once inside mitochondria, MitoSNO releases NO, which results in direct inhibition of respiration at complex (IV) of the respiratory chain (Brown, G. C. and Cooper, C. E. *FEBS Lett.* 1994, 356, 295-298; Cleeter, M. J. W., Cooper, J. M., Darley-Usmer, V. M., Moncada, S. and Schapira, A. H. V. *FEBS Lett.* 1994, 345, 50-54; Schweizer, M. and Richter, C. *Biochem. Biophys. Res. Commum.* 1994, 204, 169-175).

Previously, NO donors have been used to modify blood pressure. However, these NO donors mainly produce NO in the circulation and thus expose a range of NO receptors to NO, thereby affecting blood pressure as well as mitochondria. The compounds of the present invention selectively produce NO within the mitochondria, thereby focusing on the NO effects on the respiratory chain.

In one aspect the invention provides a compound comprising a lipophilic cation linked by a linker group to a thionitrite moiety; and a pharmaceutically acceptable anion wherein the lipophilic cation is capable of mitochondrially targeting the thionitrite moiety.

Lipophilic cations may be targeted to the mitochondrial matrix because of their positive charge. Such ions are accumulated provided they are sufficiently lipophilic to screen the positive charge or delocalize it over a large surface area, also provided that there is no active efflux pathway and the cation is not metabolized or immediately toxic to a cell.

Preferably the lipophilic cation is a substituted or unsubstituted triphenylphosphonium cation. Other lipophilic cations that may be linked to the thionitrite moiety include tribenzyl ammonium and phosphonium cations, arsonium cations or other aromatic and delocalized systems that can act as lipophilic cations and be accumulated inside mitochondria in response to the membrane potential.

In another aspect the invention provides a compound of formula (I)

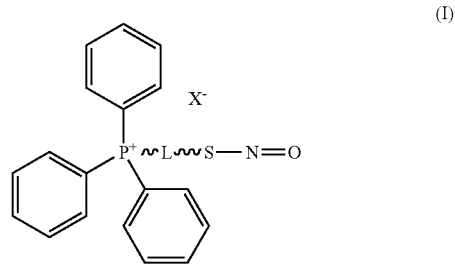

(I)

wherein ~L~ is a linker group and X is an optional anion.

The linker group (~L~) linking the lipophilic cation to the thionitrite moiety may be any chemically non-active distance-making group (spacer) which joins the triphenylphosphonium cation moiety to the thionitrite moiety, and enables the two moieties to remain bonded together when crossing the plasma and mitochondrial membranes. In particular ~L~ is stable under physiological conditions.

In one embodiment the linker group will be an alkylene group. The term "alkylene" as used herein, means a bidentate moiety obtained by removing two hydrogen atoms, either both from the same carbon atom, or one from each of two different carbon atoms, of a hydrocarbon compound having from 1 to 30 carbon atoms, preferably 2 to 20, more preferably 2 to 10, even more preferably 3 to 5 and most preferably 4, which may be aliphatic or alicyclic, and which may be saturated, partially unsaturated, or fully unsaturated. Thus, the term "alkylene" includes the sub-classes alkenylene, alkynylene, and cycloalkylene.

In one embodiment the linker group is $(C_1-C_{30})$ alkylene or substituted $(C_1-C_{30})$ alkylene. Preferably the linker group is $(C_2-C_{20})$ alkylene or substituted $(C_2-C_{20})$ alkylene. More preferably, the linker group is $(C_2-C_{10})$ alkylene or substituted $(C_2-C_{10})$ alkylene. Most preferably, the linker group is $(C_3-C_5)$ alkylene or substituted $(C_3-C_5)$ alkylene.

The linker group may also be substituted by one or more substituent groups that increases the solubility of the molecule, increases the uptake of the molecule across the plasma and/or mitochondrial membranes, or decreases the rate of degradation of the molecule in vivo.

In one embodiment the linker group is substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the substituent groups of adjacent carbon atoms in the linker group can be taken together with the carbon atoms to which they are attached to form a carbocycle or a heterocycle.

In one embodiment the linker group may be substituted by alkyl, hydroxyl, thio, amino, carboxy, amido groups or groups derived from sugars or sugar derivatives.

In one embodiment the linker group is alkyl or aryl substituted. Preferably the linker group is substituted with one or more substituents selected from the group comprising hydrogen, methyl, ethyl, propyl, butyl, pentyl, hexyl and aryl.

In one embodiment the linker group is substituted at the carbon α to the S atom. Preferably, the linker group is disubstituted with alkyl or aryl at the carbon α to the S atom. More preferably, the linker group is disubstituted with methyl groups at the carbon α to the S atom.

In one embodiment the linker group is substituted at the carbon β to the S atom. Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom.

In one embodiment the linker group is alkyl-substituted $(C_3-C_5)$ alkylene, preferably alkyl substituted butylene, more preferably, dimethyl substituted butylene.

In one embodiment the linker group is $(C_1-C_{30})$ alkylene substituted at the carbon α to the S atom. Preferably the linker group is $(C_2-C_{20})$ alkylene substituted at the carbon α to the S atom. More preferably the linker group is $(C_2-C_{10})$ alkylene substituted at the carbon α to the S atom. Most preferably the linker group is $(C_3-C_5)$ alkylene substituted at the carbon α to the S atom. Preferably, the linker group is dimethyl substituted at the carbon α to the S atom.

The linker group may also include within its structure, one or more aryl groups. The aryl group(s) may be positioned anywhere in the linker.

In one embodiment the linker group is an aryl-containing alkylene chain. Preferably, the linker group is $(C_1-C_x)$ alkylene-aryl-$(C_1-C_y)$ alkylene, or substituted $(C_1-C_x)$ alkylene-aryl-substituted $(C_1-C_y)$ alkylene where x+y=30. Preferably the linker group is $(C_2-C_{15})$ alkylene-aryl-$(C_2-C_{15})$ alkylene or substituted $(C_2-C_{15})$ alkylene-aryl-substituted $(C_2-C_{15})$ alkylene. More preferably the linker group is $(C_2-C_{10})$ alkylene-aryl-$(C_2-C_{10})$ alkylene or substituted $(C_2-C_{10})$ alkylene-aryl-substituted $(C_2-C_{10})$ alkylene. Most preferably the linker group is $(C_2-C_5)$ alkylene-aryl-$(C_2-C_5)$ alkylene or substituted $(C_2-C_5)$ alkylene-aryl-substituted $(C_2-C_5)$ alkylene.

In one embodiment the aryl group of the linker is substituted. Preferably, the aryl group is substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl.

The linker group may also include within its structure, one or more heteroatoms such as N, O and S. The heteroatom may be positioned anywhere in the linker.

In one embodiment the linker group is $(C_1-C_x)$ alkylene-NR—$(C_1-C_y)$ alkylene, or substituted $(C1-C_x)$ alkylene-NR-substituted $(C_1-C_y)$ alkylene, wherein R is hydrogen, alkyl or aryl, and x+y=30. Preferably the linker group is $(C_2-C_{15})$ alkylene-NR—$(C_2-C_{15})$ alkylene or substituted $(C_2-C_{15})$ alkylene-NR-substituted $(C_2-C_{15})$ alkylene. More preferably the linker group is $(C_2-C_{10})$ alkylene-NR—$(C_2-C_{10})$ alkylene or substituted $(C_2-C_{10})$ alkylene-NR-substituted $(C_2-C_{10})$ alkylene. Most preferably the linker group is $(C_2-C_5)$ alkylene-NR—$(C_2-C_5)$ alkylene or substituted $(C_2-C_5)$ alkylene-NR-substituted $(C_2-C_5)$ alkylene. Preferably, R is hydrogen.

Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom. Preferably, the linker group is substituted with an alkyl or aryl group at the carbon α to the S atom.

In one embodiment the linker group is $(C_1-C_x)$ alkylene-NR—C(=O)—$(C_1-C_y)$ alkylene, or substituted $(C_1-C_x)$ alkylene-NR—C(=O)-substituted $(C_1-C_y)$ alkylene, wherein R is hydrogen, alkyl or aryl and x+y=30. Preferably the linker group is $(C_2-C_{15})$ alkylene-NR—C(=O)—$(C_2-C_{15})$ alkylene or substituted $(C_2-C_{15})$ alkylene-NR—C(=O)-substituted $(C_2-C_{15})$ alkylene. More preferably the linker group is $(C_2-C_{10})$ alkylene-NR—C(=O)—$(C_2-C_{10})$ alkylene or substituted $(C_2-C_{10})$ alkylene-NR—C(=O)-substituted $(C_2-C_{10})$ alkylene. Most preferably the linker group is $(C_2-C_5)$ alkylene-NR—C(=O)—$(C_2-C_5)$ alkylene or substituted $(C_2-C_5)$ alkylene-NR—C(=O)-substituted $(C_2-C_5)$ alkylene. Preferably, R is hydrogen.

Where the linker group is $(C_1-C_x)$alkylene-NR—C(=O)—$(C_1-C_y)$alkylene, either end of the linker may be attached to the triphenylphosphonium ion. In other words, in one embodiment the linker group is $(C_1-C_x)$ alkylene-C(=O)—NR—$(C_1-C_y)$ alkylene, or substituted $(C_1-C_x)$ alkylene-C(=O)NR—$(C_1-C_y)$ substituted alkylene wherein R is hydrogen, alkyl or aryl and x+y=30. Preferably the linker group is $(C_2-C_{15})$ alkylene-C(=O)—NR—$(C_2-C_{15})$ alkylene or substituted $(C_2-C_{15})$ alkylene-C(=O)—NR-substituted $(C_2-C_{15})$ alkylene. More preferably the linker group is $(C_2-C_{10})$ alkylene-C(=O)—NR—$(C_2-C_{10})$ alkylene or substituted $(C_2-C_{10})$ alkylene-C(=O)—NR-substituted $(C_2-C_{10})$ alkylene. Most preferably the linker group is $(C_2-C_5)$ alkylene-C(=O)—NR—$(C_2-C_5)$ alkylene or substituted $(C_2-C_5)$ alkylene-C(=O)—NR-substituted $(C_2-C_5)$ alkylene. Preferably, R is hydrogen.

Preferably, the linker group is orientated so that the NR is on the triphenylphosphonium end of the —C(=O)NR— group in the chain.

Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom. Preferably, the linker group is substituted with an alkyl or aryl group at the carbon α to the S atom.

In one embodiment the linker group is $(C_1-C_x)$ alkylene-O-$(C_1-C_y)$ alkylene, or substituted $(C_1-C_x)$ alkylene-O-substituted $(C_1-C_y)$ alkylene where x+y=30. Preferably the linker group is $(C_2-C_{15})$ alkylene-O-$(C_2-C_{15})$ alkylene or substituted $(C_2-C_{15})$ alkylene-O-substituted $(C_2-C_{15})$ alkylene. More preferably the linker group is $(C_2-C_{10})$ alkylene-O-$(C_2-C_{10})$ alkylene or substituted $(C_2-C_{10})$ alkylene-O-substituted $(C_2-C_{10})$ alkylene. Most preferably the linker group is $(C_2-C_5)$ alkylene-O-$(C_2-C_5)$ alkylene or substituted $(C_2-C_5)$ alkylene-O-substituted $(C_2-C_5)$ alkylene.

Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom. Preferably, the linker group is substituted with an alkyl or aryl group at the carbon α to the S atom.

In one embodiment the linker group is $(C_1-C_x)$ alkylene-O—C(O)—$(C_1-C_y)$ alkylene, or substituted $(C_1-C_x)$ alkylene-O—C(O)-substituted $(C_1-C_y)$ alkylene where x+y=30. Preferably the linker group is $(C_2-C_{15})$ alkylene-O—C(O)—$(C_2-C_{15})$ alkylene or substituted $(C_2-C_{15})$ alkylene-O—C(O)-substituted $(C_2-C_{15})$ alkylene. More preferably the linker group is $(C_2-C_{10})$ alkylene-O—C(O)—$(C_2-C_{10})$ alkylene or substituted $(C_2-C_{10})$ alkylene-O—C(O)-substituted $(C_2-C_{10})$ alkylene. Most preferably the linker group is $(C_2-C_5)$ alkylene-O—C(O)—$(C_2-C_5)$ alkylene or substituted $(C_2-C_5)$ alkylene-O—C(O)-substituted $(C_2-C_5)$ alkylene.

Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom. Preferably, the linker group is substituted with an alkyl or aryl group at the carbon α to the S atom.

In one embodiment the linker group is $(C_1-C_x)$ alkylene-S—$(C_1-C_y)$ alkylene, or substituted $(C_1-C_x)$ alkylene-S-substituted $(C_1-C_y)$ alkylene wherein x+y=30. Preferably the linker group is $(C_2-C_{15})$ alkylene-S—$(C_2-C_{15})$ alkylene or substituted $(C_2-C_{15})$ alkylene-S-substituted $(C_2-C_{15})$ alkylene. More preferably the linker group is $(C_2-C_{10})$ alkylene-S—$(C_2-C_{10})$ alkylene or substituted $(C_2-C_{10})$ alkylene-S-substituted $(C_2-C_{10})$ alkylene. Most preferably the linker group is $(C_2-C_5)$ alkylene-S—$(C_2-C_5)$ alkylene or substituted $(C_2-C_5)$ alkylene-S-substituted $(C_2-C_5)$ alkylene.

Preferably, the linker group is substituted with a group selected from alkylcarbonylamino, arylcarbonylamino, alkylaminocarbonyl, arylaminocarbonyl, alkoxycarbonyl and aryloxycarbonyl. More preferably, the linker group is substituted with alkylcarbonylamino at the carbon β to the S atom. Preferably, the linker group is substituted with an alkyl or aryl group at the carbon α to the S atom.

Linker groups containing aryl and/or heteroatoms may also be substituted at other positions within the linker. In one embodiment the linker is optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl.

Preferably, the linker group is optionally substituted with one or more functional groups independently selected from the group consisting of alkyl, aryl, alkoxycarbonyl, aryloxycarbonyl, alkylaminocarbonyl, arylaminocarbonyl, alkylcarbonylamino and arylcarbonylamino.

The anion comprises a suitable inorganic or organic anion known in the art and is present when required for overall electrical neutrality. Examples of suitable inorganic anions include, but are not limited to, those derived from hydrochloric, hydrobromic, hydroiodic, sulfuric, sulfurous, nitric, nitrous, phosphoric or phosphorous acid or from an alkylsulfonic or an arylsulfonic acid.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyuvic, salicylic, stearic, succinic, sulfanilic, tartaric, toluenesulfonic, and valeric. All are generally recognized as pharmaceutically acceptable salts.

In one embodiment the anion is an anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide, most preferably bromide.

In another embodiment the anion is methanesulfonate.

In another aspect the invention provides a compound of formula (II)

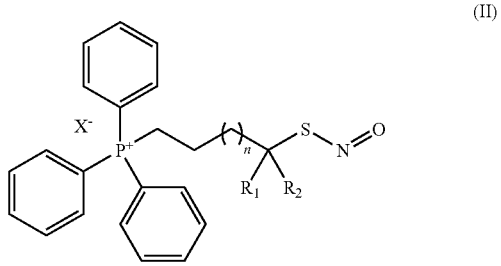

(II)

wherein n is from 0 to 27, X is an optional anion and $R_1$ and $R_2$ are independently selected from the group comprising hydrogen, alkyl and aryl.

In one embodiment n is from 0 to 20. Preferably n is from 0 to 10. More preferably n is from 0 to 2. Most preferably, n is 1.

In one embodiment $R_1$ and $R_2$ are independently selected from the group comprising hydrogen, methyl, ethyl, propyl, butyl, pentyl, hexyl and aryl. Preferably, $R_1$ and $R_2$ are methyl.

In one embodiment the anion is an inorganic anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide or methanesulfonate. Preferably, the anion is bromide or methanesulfonate.

In the compound of formula (II) the linker group comprises ($C_3$-$C_{30}$) alkylene optionally substituted with alkyl or aryl at the carbon α to the sulfur atom.

In another aspect the invention provides a compound of formula (III)

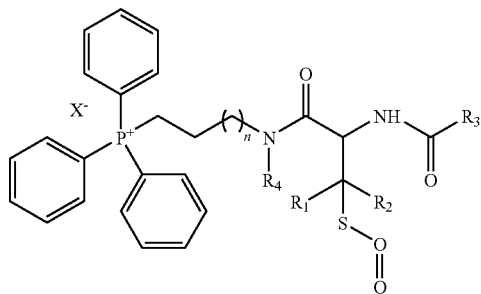

(III)

wherein n is from 0 to 27, X is an optional anion and $R_1$, $R_2$, $R_3$ and $R_4$ are independently selected from the group comprising hydrogen, alkyl and aryl.

In one embodiment n is from 0 to 20. Preferably n is from 0 to 10. More preferably n is from 1 to 5. Most preferably, n is 3.

In one embodiment $R_1$ $R_2$, $R_3$ and $R_4$ are independently selected from the group comprising hydrogen, methyl, ethyl, propyl, butyl, pentyl, hexyl and aryl. Preferably, $R_1$ $R_2$ and $R_3$ are methyl, and $R_4$ is hydrogen.

In one embodiment the anion is an inorganic anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide or methanesulfonate. Preferably, the anion is bromide or methanesulfonate.

In the compounds of formula (III) the linker group comprises ($C_2$-$C_{29}$) alkylene-NR—C(═O)—$C_2$ alkylene substituted with alkylcarbonylamino or arylcarbonylamino at the carbon β to the S atom and substituted with alkyl or aryl at the carbon α to the S atom.

In another aspect the invention provides a compound of formula (IV)

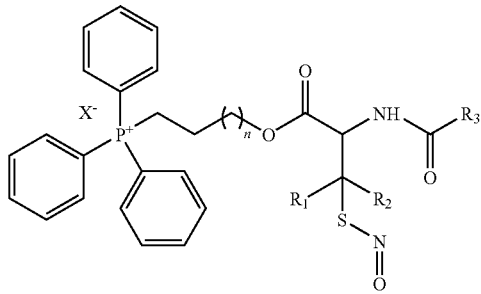

(IV)

wherein n is from 0 to 27, X is an optional anion and $R_1$, $R_2$ and $R_3$ are independently selected from the group comprising hydrogen, alkyl and aryl.

In one embodiment n is from 0 to 20. Preferably n is from 0 to 10. More preferably n is from 1 to 5. Most preferably, n is 3.

In one embodiment $R_1$ $R_2$ and $R_3$ are independently selected from the group comprising hydrogen, methyl, ethyl, propyl, butyl, pentyl, hexyl and aryl. Preferably, $R_1$ $R_2$ and $R_3$ are methyl.

In one embodiment the anion is an inorganic anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide or methanesulfonate. Preferably, the anion is bromide or methanesulfonate.

In the compound of formula (IV) the linker group comprises ($C_2$-$C_{29}$) alkylene-O—C(═O)-$C_2$ alkylene substituted with alkylcarbonylamino at the carbon β to the S atom and substituted with alkyl or aryl at the carbon α to the S atom.

In another aspect the invention provides a compound of formula (V)

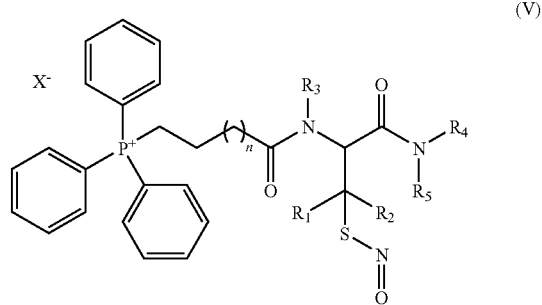

(V)

wherein n is from 0 to 27, X is an optional anion and $R_1$, $R_2$, $R_3$, $R_4$ and $R_5$ are independently selected from the group comprising hydrogen, alkyl and aryl.

In one embodiment n is from 0 to 20. Preferably n is from 0 to 10. More preferably n is from 1 to 5. Most preferably, n is 3.

In one embodiment $R_1$ $R_2$, $R_3$, $R_4$ and $R_5$ are independently selected from the group comprising hydrogen, methyl, ethyl, propyl, butyl, pentyl, hexyl and aryl. Preferably, $R_1$ $R_2$, $R_3$, $R_4$ and $R_5$ are methyl.

In one embodiment the anion is an inorganic anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide or methanesulfonate. Preferably, the anion is bromide or methanesulfonate.

In the compound of formula (V) the linker group comprises ($C_2$-$C_{29}$) alkylene-C(═O)—NR—$C_2$ alkylene substituted with alkylaminocarbonyl or arylcarbonylamino at the carbon β to the S atom and substituted with alkyl or aryl at the carbon α to the S atom.

In another aspect the invention provides a compound of formula (VI)

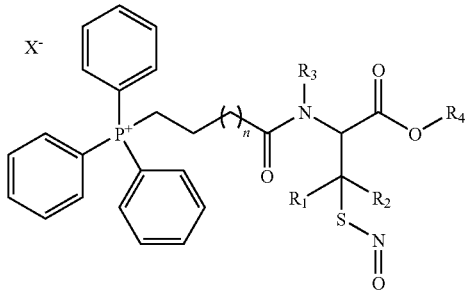

(VI)

wherein n is from 0 to 27, X is an optional anion and $R_1$, $R_2$, $R_3$ and $R_4$ are independently selected from the group comprising hydrogen, alkyl and aryl.

In one embodiment n is from 0 to 20. Preferably n is from 0 to 10. More preferably n is from 1 to 5. Most preferably, n is 3.

In one embodiment $R_1$ $R_2$, $R_3$ and $R_4$ are independently selected from the group comprising hydrogen, methyl, ethyl, propyl, butyl, pentyl, hexyl and aryl. Preferably, $R_1$ $R_2$, $R_3$ and $R_4$ are methyl.

In one embodiment the anion is an inorganic anion derived from hydrochloric, hydrobromic, hydroiodic, sulfuric, sulfurous, nitric, nitrous, phosphoric or phosphorous acid, or from an alkylsulfonic or an arylsulfonic acid.

In one embodiment the anion is chloride, bromide, iodide or methanesulfonate. Preferably, the anion is bromide or methanesulfonate.

In the compound of formula (IV) the linker group comprises ($C_2$-$C_{29}$) alkylene-C(=O)—NR—$C_2$ alkylene substituted with alkoxycarbonyl or aryloxycarbonyl at the carbon β to the S atom and substituted with alkyl or aryl at the carbon α to the S atom.

3. Synthesis of Compounds of the Invention

The compounds of the invention can be made using any convenient synthetic process. In one embodiment the compounds of the invention can be synthesised by reacting the convenient intermediate thiol of formula (VII) with nitrous acid under an inert atmosphere as shown in Scheme 1 below.

Scheme 1

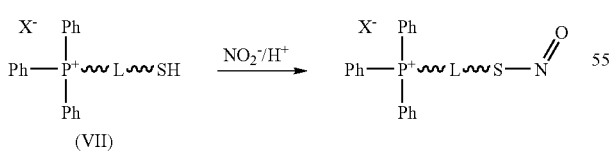

The intermediate thiol (VII) can be prepared in a number of ways depending on the final compound required. For example, in one embodiment the intermediate thiol (VII) can be prepared using Scheme 2 as outlined below (Burns, R. J., Smith, R. A. J. and Murphy, M. P. *Archives of Biochemistry and Biophysics*, 1995, 322, 60-68).

Scheme 2

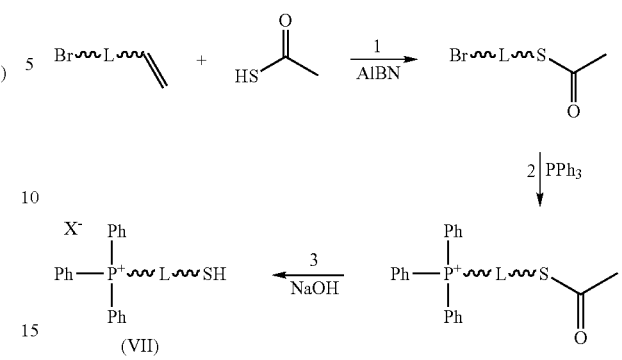

1. A linker group including a bromine group at one end and an alkylene group at another end are reacted with thioacetic acid using the radical generator 2,2'-azobisisobutyronitrile (AIBN).
2. The product of step 1 is then fused together with triphenylphosphine ($PPh_3$).
3. The intermediate thiol (VII) is generated by base hydrolysis with NaOH and anion exchange.

Using the synthetic schemes provided above, a number of different compounds of the invention can be prepared via nitrous acid reaction with the intermediate thiol of formula (VII). For example, Schemes 3 to 5 demonstrate how compounds of the invention incorporating substituted linker groups can be made using these synthetic schemes.

Scheme 3

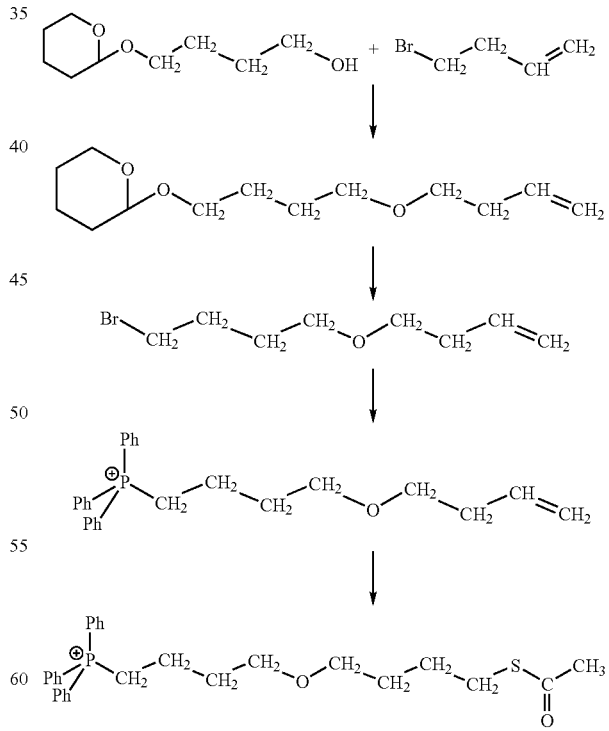

Scheme 3 outlines the synthesis of a protected thiol intermediate compound incorporating an ether functionality in the linker. Base hydrolysis provides a compound of the invention wherein the linker group is $C_4$ alkylene-O—$C_4$ alkylene.

Scheme 4

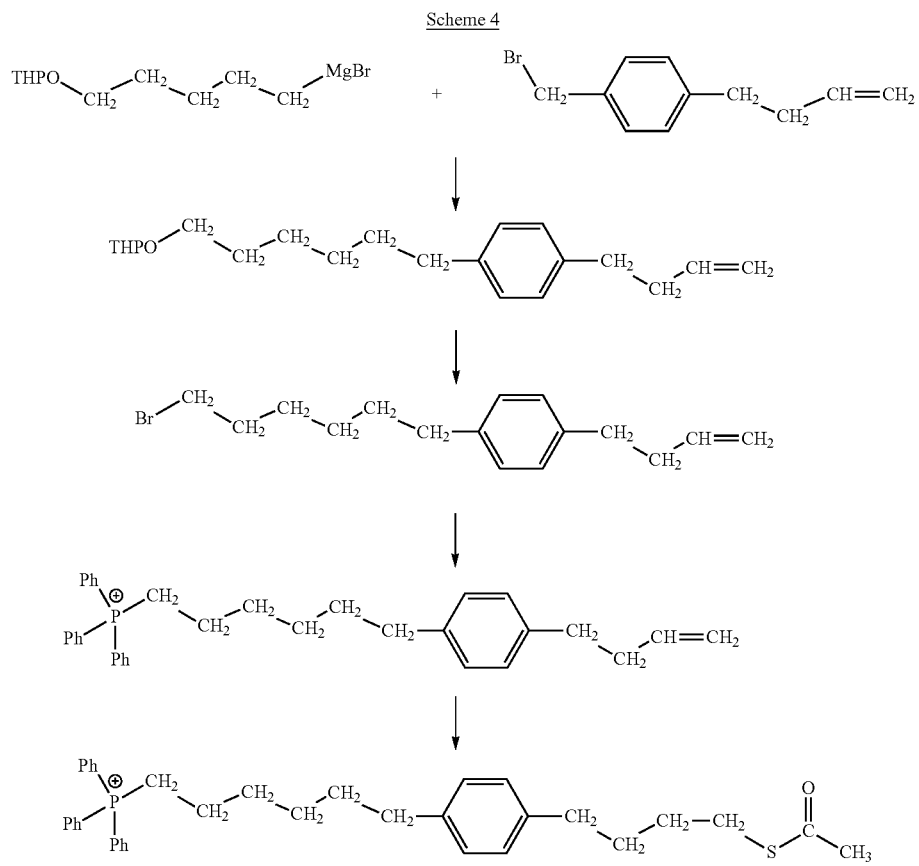

Scheme 4 outlines the synthesis of a protected thiol intermediate compound incorporating a benzene functionality in the linker. THP is tetrahydrophyran. Base hydrolysis provides a compound of the invention wherein the linker group is an aryl-containing alkylene chain, $C_6$ alkylene-aryl-$C_4$ alkylene.

Scheme 5

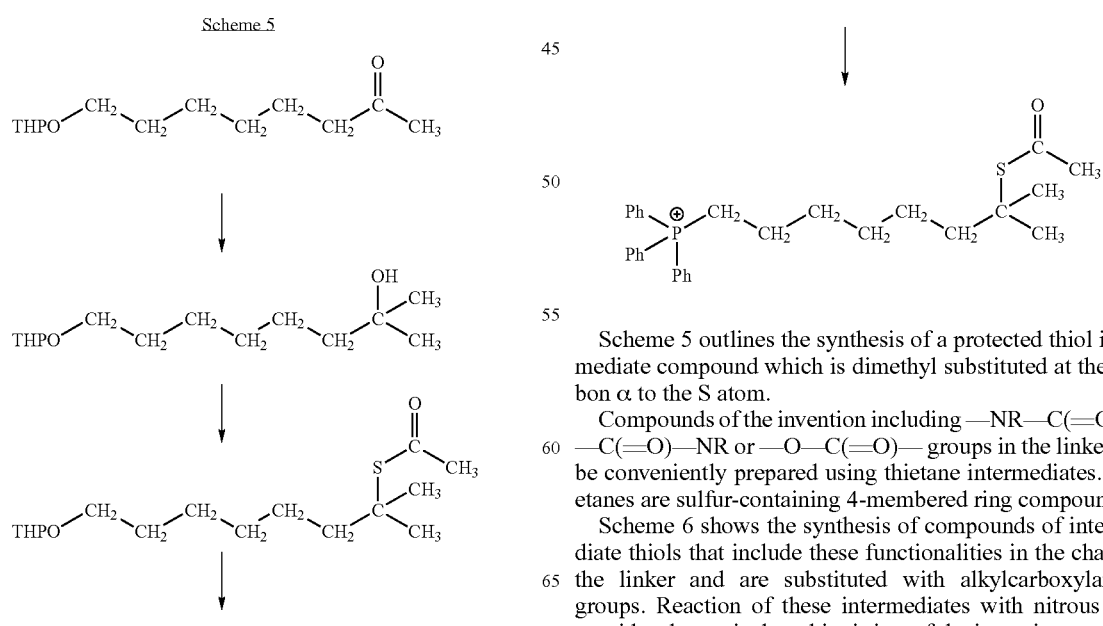

-continued

Scheme 5 outlines the synthesis of a protected thiol intermediate compound which is dimethyl substituted at the carbon α to the S atom.

Compounds of the invention including —NR—C(=O)—, —C(=O)—NR or —O—C(=O)— groups in the linker can be conveniently prepared using thietane intermediates. Thietanes are sulfur-containing 4-membered ring compounds.

Scheme 6 shows the synthesis of compounds of intermediate thiols that include these functionalities in the chain of the linker and are substituted with alkylcarboxylamine groups. Reaction of these intermediates with nitrous acid provides the equivalent thionitrites of the invention Scheme 6

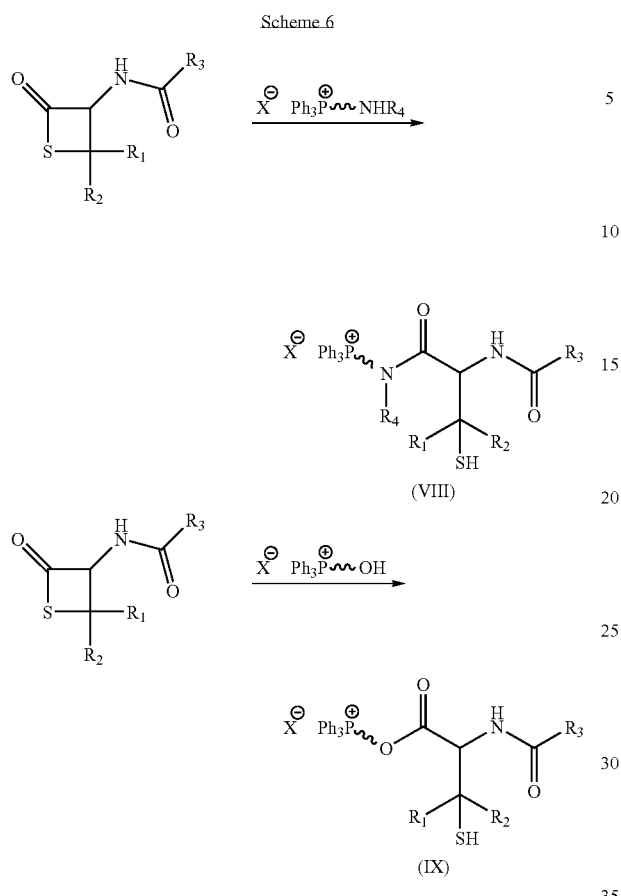

Compounds of formula (VIII) are prepared using a triphenylphosphonium cation attached to a linker group that includes an amine group at the opposite end. Compounds of formula (IX) are prepared using a triphenylphosphonium cation with a hydroxy attached to the end of the linker group. Generally the remainder of the linker group is an alkylene chain but the linker group of the thiol intermediate can be altered further by using triphenylphosphonium cations linked to the amine or hydroxy groups via other chains, for example, substituted alkylene chains.

When reacted with the thietane compound, the amine or alcohol group at the end of the linker group opens the thietane ring to provide the thiol intermediate. If the amine group is a secondary amine ($R_4$ is alkyl or aryl), the resulting compound of formula (VIII) is N-alkyl or aryl substituted.

Reaction with the thietane shown above provides a thiol intermediate that is substituted with an amide group at the position β to the sulfur atom and also substituted at the carbon α to the sulfur atom. The nature of the substitution at $R_1$, $R_2$ and $R_3$ depends on the thietane used. Many thietanes are commercially available, for example, N-(2-ethyl-2-methyl-4-oxo-3-thietanyl)acetamide. Other alkyl and aryl groups can be introduced using thiotanes with different $R_1$, $R_2$ and $R_3$ substituents. Such thietanes can easily be prepared by a person skilled in the art using known techniques.

For example, thietanes for use in synthesising compounds of the invention can also be prepared by reaction of modified cysteine, as shown in scheme 7 below.

Scheme 7

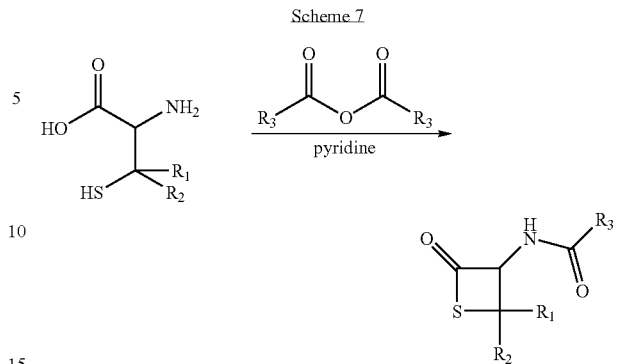

Generally, $R_1$, $R_2$ and $R_3$ will be alkyl or aryl.

However, if a triphenylphosphonium cation linked acid chloride is added to the reaction in Scheme 7, it is possible to make a thietane intermediate that incorporates the triphenylphosphonium cation linked functionality in the $R_3$ position. This compound can then be opened with an amine or alcohol to provide thiol intermediate compounds where the C(=O) is on the triphenylphosphonium end of the —C(=O)NR— group in the linker chain. Additionally, alcohol opening provides a thiol intermediate where the linker is substituted at the carbon α to the sulfur with an ester group. These reactions are shown in Scheme 8 below.

Scheme 8

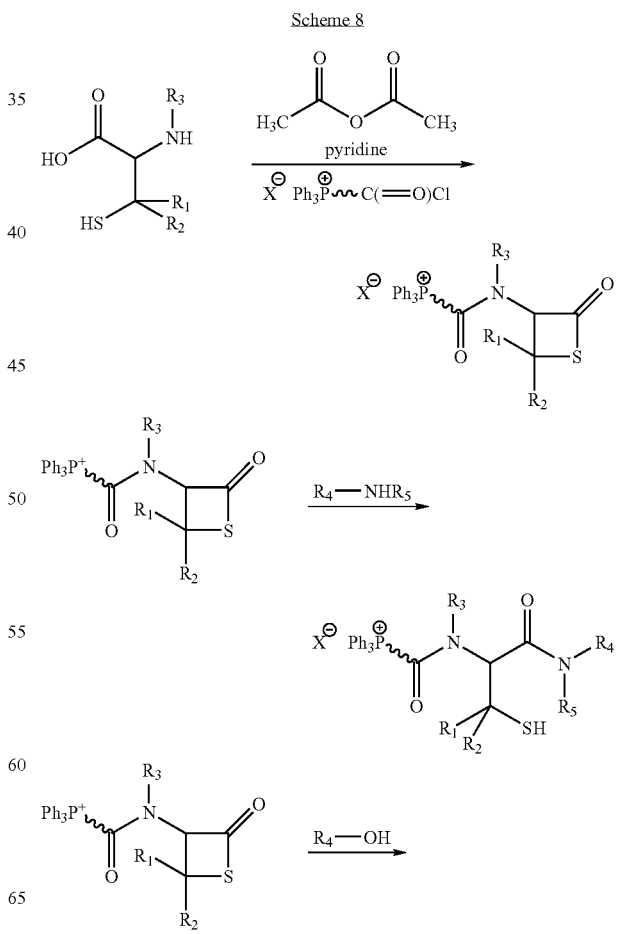

-continued

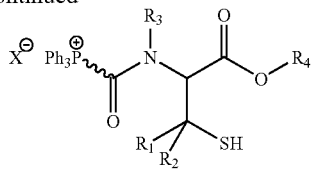

Compounds of the invention may be prepared according to the general methodology described above. It is to be understood that a skilled worker will be able, without undue experimentation and with regard to that skill and this disclosure, to select appropriate reagents and conditions to modify this methodology to produce compounds of the invention.

Those of skill in the art will also appreciate that other synthetic routes may be used to synthesize the compounds of the invention. In addition, it will be appreciated by those of skill in the art that, in the course of preparing the compounds of the invention, the functional groups of intermediate compounds may need to be protected by protecting groups. Functional groups which it is desirable to protect include, but are not limited to hydroxyl, amino and carboxylic acid. Protecting groups may be added and removed in accordance with techniques that are well known to those skilled in the art. The use of protecting groups is fully described in "Protective Groups in Organic Chemistry", edited by J. W. F McOmie, Plenum Press (1973), and "Protective Groups in Organic Synthesis", $2^{nd}$ Ed, T. W. Greene and P. G. M Wutz, Wiley-Interscience (1991).

4. Uses of Compounds of the Invention

In another aspect the invention provides a pharmaceutical composition comprising a therapeutically effective amount of a compound of the invention in combination with one or more pharmaceutically acceptable excipients, carriers or diluents.

Suitable excipients, carriers and diluents can be found in standard pharmaceutical texts. See, for example, Handbook for Pharmaceutical Additives, $2^{nd}$ Edition (eds. M. Ash and I. Ash), 2001 (Synapse Information Resources, Inc., Endicott, N.Y., USA) and Remington's Pharmaceutical Science, (ed. A. L. Gennaro) 2000 (Lippincott, Williams and Wilkins, Philadelphia, USA) which are incorporated herein by reference.

Excipients for use in the compositions of the invention include, but are not limited to microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavouring agents, colouring matter or dyes, and, if so desired, emulsifying and/or suspending agents as well, together with such diluents as water, ethanol, propylene glycol, glycerin and various like combinations thereof.

Pharmaceutical carriers include solid diluents or fillers, sterile aqueous media and various non-toxic organic solvents, and the like.

NO has been shown to be a reversible inhibitor of the mitochondrial respiratory chain by competing with oxygen at cytochrome oxidase. Selective delivery of NO to mitochondria by the compounds of the invention enables the respiration rate to be reversibly modulated within patients. Consequently, the compounds of the invention may be useful in the treatment of conditions that are affected by the inhibition of cytochrome oxidase.

The compounds of the invention do not act like other cytochrome oxidase inhibitors such as cyanide, because they compete with oxygen and thereby only affect respiration when the oxygen concentration is low. This effect is reversed once the oxygen concentration increases. Accordingly, the compounds of the invention can be considered modulators of the effective $K_m$ of cytochrome oxidase.

Selective, reversible inhibition of mitochondria by the compounds of the invention can be used to treat ischaemia-reperfusion injury by preventing hypoxic tissue from becoming entirely anaerobic. Ischaemia is the condition suffered by tissues and organs when deprived of blood flow. It is mostly the result of inadequate nutrient and oxygen supply. Reperfusion injury refers to the tissue damage inflicted when blood flow is restored after an ischemic period of more than about ten minutes. Ischaemia and reperfusion can cause serious brain damage in stroke or cardiac arrest.

Compounds of the invention have been shown to protect against heart ischemia and reperfusion injury (see Examples 14 and 15).

Example 14 shows that compounds of the invention protected against cardiac I/R injury when the compound was administered during the reperfusion phase in an ex vivo Langendorff heart I/R injury model. Example 15 demonstrates the efficacy of the compounds in a well established murine model of in vivo I/R injury by subjecting mice to occlusion of the left anterior descending coronary artery (LAD) for 30 min followed by reperfusion and recovery over 24 h.

Figure 19:
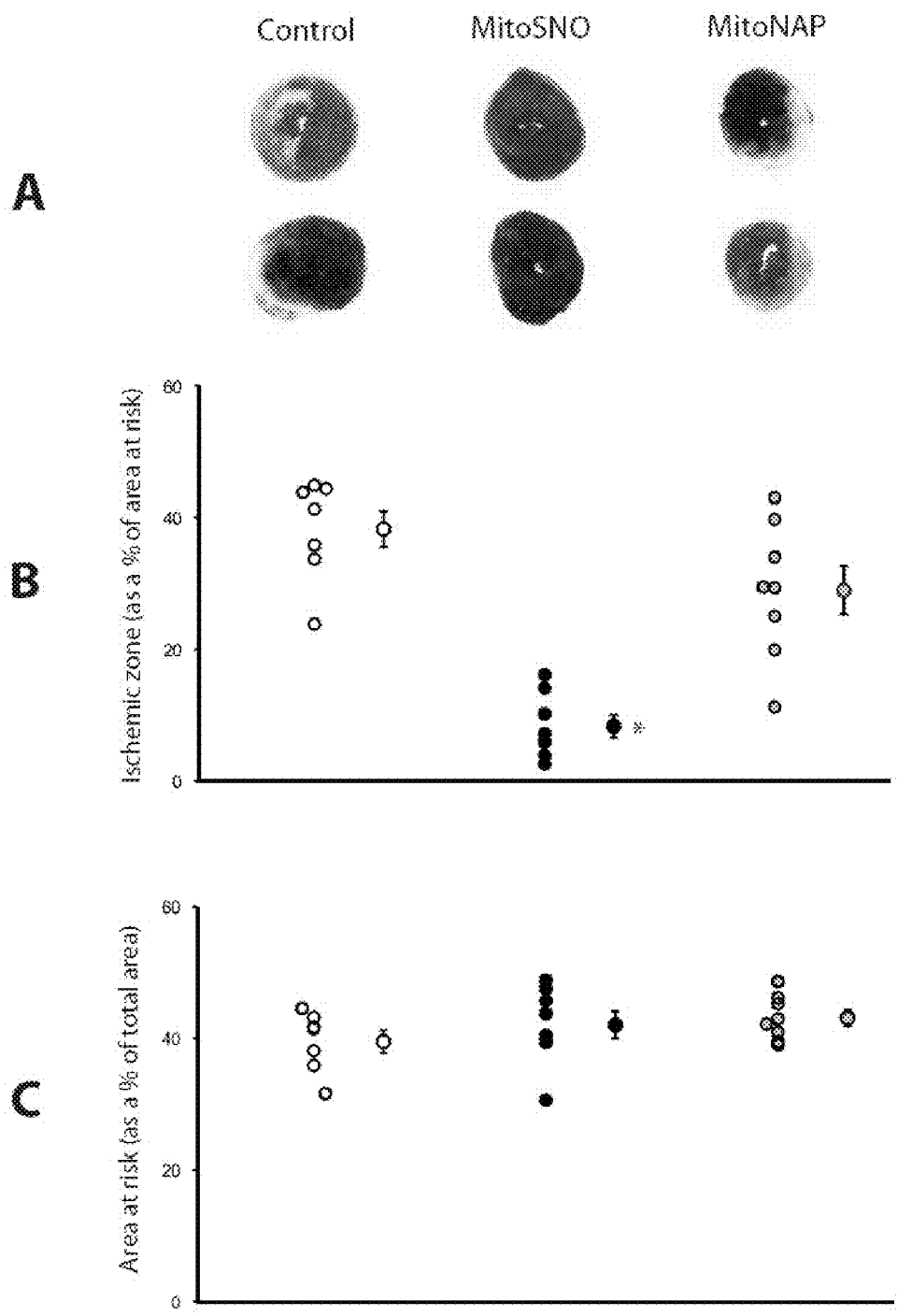
FIG. 19 is a pictorial representation of the area at risk (AR) and infarct zone, stained with Evans' blue and TTC respectively, then scanned. The infarct/AR ratios were determined with NIH ImageJ software.

Following the recovery period, analysis of the heart showed significant damage, as indicated by the area of infarcted tissue (FIG. 19A, white tissue), and by comparison of the infarcted zone to the area of tissue at risk (AR) (FIG. 19B). In contrast, injection of a compound of the invention into the left ventricle 5 min prior to reperfusion significantly decreased heart damage (FIGS. 19, A and B). Control injections with MitoNAP, the MitoSNAP precursor that lacks the S-nitrosothiol, were not protective (FIG. 19). These results confirm our initial findings of protection against cardiac I/R injury by compounds of the invention and are consistent with a protective role for mitochondrial protein S-nitrosation during cardiac I/R injury.

These experiments indicate that compounds of the invention provide a protective effect when administered during reperfusion. This provides a significant advantage as most cardioprotective agents must be administered prior to ischemia and reperfusion injury. Consequently, the compounds of the invention may be useful in the treatment of myocardial infarction and stroke to prevent ischaemia-reperfusion injury.

During general surgery the blood supply is often halted to key organs or tissues which can result in damage. The compounds of the invention may be used pre-surgically to minimise damage to organs and tissues caused by reperfusion, for example, during heart surgery.

Compounds of the invention may also be useful for preserving organs during organ transplant procedures.

The compounds of the invention have activity as angiogenesis inhibitors to prevent tumour growth and metastasis.

Tumors above a certain size have to attract blood vessels to them in order to grow and blocking angiogenesis has proven to be a successful approach to targeting cancers. The signaling pathway for angiogenesis involves sensing that oxygen concentration is lowered due to poor blood supply. This is done by the oxygen dependent degradation of hypoxia inducible factor 1-α (HIF-1α). Under hypoxia, HIF-1α is no longer degraded and acts as a transcription factor inducing a range of processes including angiogenesis. It has been shown that exposure to NO can facilitate HIF-1α degradation by partially inhibiting respiration and thereby increasing the local oxygen concentration (Hagen, T., Taylor, C. T., Lam, F., Moncada, S. *Science,* 2003, 302, 1975-1978).

The compounds of the invention act as angiogenesis inhibitors by inhibiting cytochrome oxidase thereby increasing the local oxygen concentration in hypoxic tumours. This destabilises the transcription factor hypoxia inducible factor 1-α (HIF-1α) thereby blocking angiogenesis to the tumour.

Thus, the selective production of NO within mitochondria by the compounds of the invention may act to switch off angiogenesis in tumors without affecting respiration in fully aerobic tissues. This will result in a slowing of tumour development.

The compounds of the invention have also shown to relax the smooth muscle in blood vessel walls thereby acting as vasodilators (see Example 13). Consequently, they may have application in the treatment of angina and high blood pressure.

The compounds of the invention can also be used in conjunction with other therapies such as anti cancer agents and other pharmaceuticals.

The conjugates or pharmaceutical compositions of the invention can be administered via oral, parenteral (such as subcutaneous, intravenous, intramuscular, intracisternal and infusion techniques), rectal, intranasal or topical routes. In general, these compounds are administered in doses ranging from about 0.5 to about 500 mg per day, in single or divided doses (such as from 1 to 4 doses per day).

It will be appreciated by one of skill in the art that appropriate dosages of the compounds, and compositions comprising the compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition and the general health and prior medical history of the patient.

The active compounds of this invention can be administered alone or in combination with pharmaceutically acceptable excipients, carriers or diluents by any of the routes previously indicated, and such administration may be carried out in single or multiple doses.

More particularly, the novel therapeutic agents of this invention can be administered in a wide variety of different dosage forms, they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions injectable solutions, elixirs, syrups, and the like. Such carriers include solid diluents or fillers, sterile aqueous media and various non-toxic organic solvents, and the like. Injectable forms are preferred.

Moreover, oral pharmaceutical compositions can be suitably sweetened and/or flavoured. In general, the conjugates of the invention are present in such dosage forms at concentration levels ranging from about 1.0% to about 70% by weight, preferably about 1.0% to about 70% by weight.

For oral use in treating the various disorders and conditions referred to above, the conjugates can be administered, for example, in the form of tablets or capsules, or as an aqueous solution or suspension. Tablets may contain various excipients such as described above.

For parenteral administration, solutions of a compound of the present invention in oils such as sesame or peanut oil, or an aqueous propylene glycol may be employed. The aqueous solutions should be suitably buffered (preferably pH less than 8) if necessary and the liquid diluent first rendered isotonic. These aqueous solutions are suitable for intravenous injection purposes. The oily solutions are suitable for intra-muscular and subcutaneous injection purposes. The preparation of all these solutions under sterile conditions is readily accomplished by standard pharmaceutical techniques well known to those skilled in the art.

For intramuscular, parenteral and intravenous use, sterile solutions of the active ingredient can be prepared, and the pH of the solutions should be suitably adjusted and buffered. For intravenous use, the total concentration of solutes should be controlled to render the preparation isotonic.

Various aspects of the invention will now be illustrated in non-limiting ways by reference to the following examples.

Methods

Nitrite, nitric oxide and S-nitrosothiol measurements. Nitrite was analyzed by the Griess assay (Molecular Probes). Nitric oxide was measured using an NO$^\bullet$ electrode (World Precision Instruments Ltd, UK) connected to an Apollo 4000 Free Radical Analyser. The electrode was inserted into a stirred, sealed 3 ml chamber with a Clark type $O_2$ electrode (Rank Brothers, UK) built into its base and was thermostatted at 37° C. The NO$^\bullet$ electrode was calibrated by adding SNAP to argon-purged, saturated CuCl. OxyHb was prepared by reduction of bovine methemoglobin with sodium dithionite. Protein S-nitrosothiols were measured using a chemiluminescence assay in an EcoMedics CLD 88 Exhalyzer (Annex, Herts, UK) (Feelisch, M. et al. Concomitant S—, N—, and heme-nitros(yl)ation in biological tissues and fluids: implications for the fate of NO in vivo. *FASEB. J.* 16, 1775-85 (2002)).

Cell culture. Cells were grown in medium supplemented with 10% fetal calf serum (FCS), penicillin (100 U.ml$^{-1}$) and streptomycin (100 μg.ml$^{-1}$) at 37° C. in a humidified atmosphere of 95% air/5% $CO_2$. Jurkat cells were cultured in Roswell park memorial institute (RPMI) 1640 medium supplemented with 2 mM Glutamax and 25 mM Hepes. HeLa cells were grown in minimum essential eagle medium (MEM) containing 2 mM glutamine and non-essential amino acids and were grown to 100% confluence prior to use. C2C12 cells were grown in Dulbecco's modified Eagle's medium (DMEM) and were seeded at ~25,000-30,000 cells/cm$^2$ and grown overnight prior to experiments. A mitochondria-enriched fraction from C2C12 cells was prepared from C2C12 cells, as described below.

Mitochondrial preparations and incubations. Rat liver mitochondria were prepared in 250 mM sucrose, 5 mM Tris-HCl, 1 mM ethylene glycol-bis(β-aminoethyl ether)-N,N,N', N'-tetraacetic acid (EGTA), pH 7.4. Rat heart mitochondria were prepared in 250 mM sucrose, 5 mM Tris-HCl, 1 mM EGTA, 0.1% bovine serum albumin (BSA), pH 7.4. Mitochondrial membranes were prepared from bovine heart mitochondria as described (Beer, S. M. et al. Glutaredoxin 2

Catalyzes the reversible oxidation and glutathionylation of mitochondrial membrane thiol proteins: implications for mitochondrial redox regulation and antioxidant defense. *J. Biol. Chem.* 279, 47939-51 (2004)). Protein concentration was determined by the biuret assay using BSA as a standard or by the bicinchoninic acid assay.

Mitochondrial incubations were usually in KCl buffer (120 mM KCl, 10 mM HEPES, 1 mM EGTA, 100 µM N,N-bis(2-bis[carboxymethyl]aminoethyl) glycine (DTPA) and 10 µM neocuproine, pH 7.2) with 10 mM succinate and 4 µg/ml rotenone in the dark at 37° C., unless stated otherwise. An electrode selective for the TPP moiety of MitoSNAP and MitoNAP was made and used as described previously (Asin-Cayuela, J., Manas, A. R., James, A. M., Smith, R. A. & Murphy, M. P. Fine-tuning the hydrophobicity of a mitochondria-targeted antioxidant. *FEBS Letts.* 571, 9-16 (2004)). Respiration rates were measured in a Clark type $O_2$ electrode (Rank Brothers, UK). To measure GSH and GSSG, mitochondria (1 mg protein/ml) were incubated with 0-10 µM MitoSNO1 or MitoNAP for 10 min, pelleted by centrifugation and the GSH and GSSG contents assessed by the recycling assay (Scarlett, J. L., Packer, M. A., Porteous, C. M. & Murphy, M. P. Alterations to glutathione and nicotinamide nucleotides during the mitochondrial permeability transition induced by peroxynitrite. *Biochem. Pharmacol.* 52, 1047-1055 (1996)). The measurement of exposed mitochondrial protein thiols is described below.

Aorta Relaxation Measurements

Sprague-Dawley rats (male 250-350 g) were anesthetized by intraperitoneal injection of ketamine and xylazine (100 and 16 mg/kg, respectively) and thoracic aortas were excised and placed in Krebs-Henseleit buffer (pH 7.3) at 37° C. Aortic segments were cut into seven to eight ~3 mm-long rings, mounted in baths containing 15 ml Krebs-Henseleit buffer equilibrated with 21% $O_2$, 5% $CO_2$ at 37° C. and isometric vessel tension was established using a vessel bioassay system (Radnoti, Monrovia Calif.). Indomethacin (5 µM) treated aorta was pre-contracted with phenylephrine (100 nM) and L-$N^G$-monomethylarginine (100 µM) and then treated with test compounds. For decomposition MitoSNAP and SNAP were exposed to light for 2 h, resulting in >90% SNO degradation. All vasodilatation studies were performed under subdued light settings. The concentrations of MitoSNAP and SNAP were calculated using $\epsilon=950$ $M^{-1}.cm^{-1}$ and 1168 $M^{-1}.cm^{-1}$ at 340-344 nm respectively in PBS supplemented with 10 µM DTPA.

Heart Ischemia-Reperfusion Injury (Ex Vivo)

Male C57BL6 mice (30-35 g) were obtained from Harlan (Indianapolis, Ind.) and were maintained with food and water available ad libitum. All procedures were carried out in accordance with the Guide for the Care and Use of Laboratory Animals (NIH publication #85-23, 1996). Isolated mouse hearts were retrograde reperfused in Langendorff mode under constant flow (4 ml/min), essentially as described for rat hearts (Nadtochiy, S. M., Tompkins, A. J. & Brookes, P. S. Different mechanisms of mitochondrial proton leak in ischaemia/reperfusion injury and preconditioning: implications for pathology and cardioprotection. *Biochem. J.* 395, 611-8 (2006)).

Heart Ischemia-Reperfusion Injury (In Vivo)

Male C57BL/6 mice (~25 g) were purchased from the Jackson Laboratory and handled in accordance with the procedures of the University of Rochester Committee on Animal Research. All surgical procedures were sterile and performed as described previously. Briefly, analgesics (acetaminophen 0.75 mg/ml in drinking water) were administered 24 hr before, and during the perioperative period. Acetaminophen does not impact on I/R injury.

Measurement of S-Nitrosothiols

After incubation the mitochondrial, or mitochondrial membrane, suspensions were supplemented with 10 mM NEM and 1 min later was pelleted by centrifugation (10,000×g for 5 min) and resuspended 1 ml KCl buffer supplemented with 10 mM NEM and pelleted once more. The pellet was then resuspended in 1 ml 25 mM HEPES pH 7.2, 100 µM DTPA, 10 µM neocuproine and 10 mM NEM, snap frozen on dry ice/ethanol, freeze/thawed (×3) and stored at −20° C. until analysis. For measurements on cells, the medium was removed then the cell layer was washed in PBS/10 mM NEM, then scraped into 1 ml PBS/NEM and snap frozen on dry ice/ethanol, freeze/thawed (×3) and stored at −20° C. until analysis. Samples (225-450 µl) were thawed rapidly just prior to analysis and made up to a final volume of 250-500 µl containing 0.1 M HCl and 0.5% sulphanilamide±0.2% $HgCl_2$ and incubated in the dark for 30 min. Then duplicate 100-500 µl samples were injected into 20 ml of an acidic $I^-/I_2$ solution (33 mM KI, 14 mM $I_2$ in 38% (v/v) acetic acid) through which bubbled helium that carried the NO produced through a 1 M NaOH trap to the analyser where it is mixed with ozone and the chemiluminescence measured. The peak area is compared to a standard curve generated from $NaNO_2$ standards. As $HgCl_2$ selectively degrades SNOs, the SNO content was the difference between the samples with and without $HgCl_2$. A control experiment was carried out in which mitochondria were incubated with 5 µM MitoSNAP for 5 min when the mitochondrial suspension was supplemented with 10 mM NEM and 1 min later was pelleted by centrifugation (10,000×g for 5 min) as above. The pellet was then resuspended in 1 ml 5% sulfosalicylic acid to fully lyse mitochondria and precipitate protein which was pelleted and washed again in 1 ml 5% sulfosalicylic acid, when the protein pellet was resuspended in 1 ml 25 mM HEPES pH 7.2, 100 µM DTPA, 10 µM neocuproine and 10 mM NEM KCl buffer supplemented with 10 mM NEM and assessed for SNOs as above. This gave a significant amount of S-nitrosated proteins (359±89 pmol SNO/mg protein, mean±SEM of 4), confirming that the SNOs measured in mitochondria are due to S-nitrosated proteins and not to carry over of MitoSNAP trapped within mitochondria into the SNO assay.

Measurement of Exposed Protein Thiols

To measure exposed mitochondrial protein thiols, mitochondria (1 mg protein/ml) were incubated in 1 ml KCl Buffer for 5 min, pelleted by centrifugation and the pellet resuspended in 75 µl 250 mM sucrose, 5 mM HEPES, 1 mM EGTA, pH 7.4 supplemented with 0.1% dodecylmaltoside. Small molecules were removed by centrifugation through MicroBioSpin Columns (cut off=6 kDa), the eluate was clarified by centrifugation (2 min at 10,000×g) and protein thiols measured in triplicate by mixing 10 µl sample or GSH standard with 160 µl of 200 µM dithionitrobenzoic acid (DTNB) in 80 mM $NaP_i$, 1 mM EDTA, pH 8 in a 96 well plate and absorbance at 412 nm was measured after 30 min at room temperature and the thiol content determined from the GSH standard curve. The protein concentration was measured in parallel by the bicinchonininc assay using BSA as a standard.

Preparation of a Mitochondria-Enriched Fraction from C2C12 Cells

C2C12 cells were seeded (~$2\times10^6$ cells per 14 $cm^2$ dish) and grown with 25 ml medium/dish for 46 h giving ~$7\times10^6$ cells per 14 $cm^2$ dish. The medium was removed and replaced with 10 ml medium. To this DMSO or 20 µM FCCP was added and incubated for 5 min at 37° C. in the dark. After this 5 μM MitoSNAP or SNAP or ethanol was added and incubated for a further 5 min in the dark. The supernatant was aspirated and the cell sheet was washed first in PBS/10 mM NEM then in buffer A (100 mM sucrose, 1 mM EGTA, 20 mm MOPS, pH 7.4, 10 mM NEM, 100 μM DTPA, 10 μM neocuproine) while on ice. Cells were scraped into 1 ml SEM buffer and the plate washed in 4 ml of the same buffer. The cell suspension was centrifuged (200×g for 5 min at 4° C.) and the pellet resuspended in 500 μl buffer B (=buffer A supplemented with 0.1 mg/ml digitonin and 10 mM triethanolamine) and incubated on ice for 3 min then 2.5 vols of buffer A was added. This was homogenised 20× using a tight fitting Dounce, then spun 1 min at 1,000×g at RT. The supernatant was kept and the pellet was washed again in buffer A again the supernatant was retained. These were combined and spun at 10,000×g for 5 min at 4° C. The supernatant (cytosol fraction) was snap frozen and the pellets combined in 500 μl 25 mM HEPES pH 7.2, 100 μM DTPA, 10 μM neocuproine and 10 mM NEM and then snap frozen. Samples were freeze thawed 3× and aliquots prepared for S-nitrosothiol analysis.

Electrophoresis and Visualisation of S-Nitrosated Proteins

Isolated rat liver or rat heart mitochondria (4 mg protein/ml) were suspended in KCl buffer supplemented with 10 mM succinate and 8 μg/ml rotenone and were incubated with no additions, 10 μM MitoSNAP or 500 μM diamide at 37° C. for 5 min with occasional mixing. Mitochondria were then pelleted by centrifugation and resuspended in a blocking buffer containing 250 mM HEPES, pH 7.7, 1 mM EDTA, 1 mM DTPA, 10 μM neocuproine, 1% SDS, and 50 mM NEM. This blocking reaction was carried out for 5 min at 40° C. The reaction mixture was then passed three times through Micro-BioSpin Columns (cut off=6 kDa: BioRad, #732-6222) to remove NEM. Cy3 maleimide (200 μM; Amersham product number PA 13131), 1 mM ascorbate, and 10 μM $CuSO_4$ were added and the mixture gently vortexed and then incubated for 30 min at 37° C. The protein (10 μg) was then separated on a 12.5% SDS PAGE gel. After electrophoresis, the gel image was acquired with a Typhoon 9410 variable mode imager.

To assess S-nitrosation, bovine heart mitochondrial membranes (250 μg/ml) were incubated in KCl buffer±75 μM MitoSNAP at 37° C. for 5 min with occasional mixing. Then 10 mM NEM was added and incubated for 5 min at 40° C. The membranes were then pelleted by centrifugation and washed three times in 1 ml PBS buffer. The pellet was then resuspended in 100 μl PBS supplemented with 200 μM Cy3 maleimide, 1 mM ascorbate, and 10 μM $CuSO_4$ and incubated for 30 min at 37° C. When testing the reversibility of MitoSNAP S-nitrosation with GSH, membranes were treated with 1 mM GSH for 15 minutes prior to the blocking step. BN-PAGE samples were prepared and separated on a 5-12% gradient acrylamide gel. Following electrophoresis, the gel image was acquired with a Typhoon 9410 variable mode imager scanning for Cy3 fluorescence at 532 nm. Proteins were then transferred to a nitrocellulose membrane and probed with rabbit antisera against the bovine 24 kDa Complex I subunit (a gift from Prof John E. Walker), a mouse monoclonal against bovine complex III, core subunit 2 (from Molecular Probes/Invitrogen, A-11143) or a mouse monoclonal against bovine Complex V β subunit (from Molecular Probes/Invitrogen, A-21351). These were then probed with secondary antibody-horseradish peroxidase conjugates and visualised by enhanced chemiluminescence (Amersham Biosciences).

HPLC Analysis

MitoSNAP, MitoNAP and their derivatives were separated by reverse phase HPLC (RP-HPLC) on a C18 column (Jupiter 300 Å, Phenomenex) with a Widepore C18 guard column (Phenomenex), using a Gilson 321 pump. Samples were injected manually through a 0.22 μm PVDF filter (Millipore) into a 2 ml sample loop and then a gradient of A (0.1% TFA) and B (100% ACN, 0.1% TFA) was run at 1 ml.min$^{-1}$ (time in min, % B): 0-5, 5%; 5-10, 5-40% 10-25, 40-80%; 25-27.5, 80-100%; 27.5-30, 100%; 30-32.5, 100-5%. Peaks were detected at 220 nm using a Gilson UV/VIS 151 spectrophotometer. MitoNAP and MitoSNAP standards were used to identify peak elution times.

Mass Spectrometry

MitoSNAP decay products were identified by electrospray mass spectrometry (ESMS) using a Quattro triple quadrupole mass sepctrometer. RP-HPLC peaks were collected in 50-60% ACN, 0.1% TFA, transferred to sample vials and compared with 1 μM MitoNAP or MitoSNAP standards in 50% ACN, 0.1% TFA. An isocratic solvent (50% ACN) was infused continuously at 20 μl/min into a Quattro triple quad mass spectrometer and an automated sample injector was used to infuse samples (30 μl) into the solvent flow. Spectra over 400-700 m/z were accumulated continuously over 5 min. A MitoNAP standard used for internal callibration gave m/z=521.5 (expect 521.23).

Cell Hypoxia Experiments

HeLa cells were seeded and grown to 100% confluence with 15 ml medium/dish on 165 cm$^2$ dishes. The medium was aspirated and replaced with 15 ml fresh medium. The dishes were then placed in a humidified hypoxia workstation (Coy Laboratories) at 1% $O_2$ concentration with 5% $CO_2$ and the balance $N_2$ for 60 min. The indicated concentration of MitoNAP, MitoSNAP and myxothiazol was added to individual dishes which were incubated in the dark for a further 30 min. Extracellular $pO_2$ measurements were taken by fluorescence quenching oximetry (Oxylite-2000; Oxford Optronix). Statistical analysis was performed using SPSS 12.0.1.

EXAMPLE 1

A compound of formula (X) was prepared as described in Schemes 1 and 2 above.

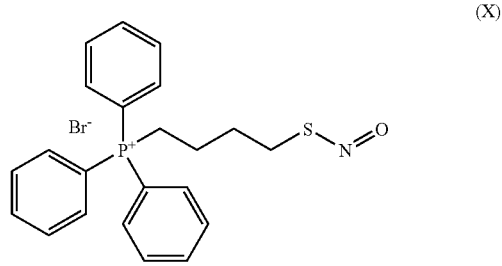 [SMILES: O=NSCCCC[P+](c1ccccc1)(c1ccccc1)c1ccccc1 ; [Br-]]

(X)

All solutions were sparged with argon for 60 sec before use. 4-Thiobutyltriphenylphosphonium bromide (25.4 mg, 56.8 μmol) was dissolved in ethanol (0.300 mL) and the solution was flushed with argon and cooled on ice in the dark, for 10 min. Aqueous hydrochloric acid (0.130 mL, 80.6 μmol) was added and the reaction vessel swirled in the ice and then 1 min later an aqueous solution of sodium nitrite (0.120 mL, 92.3 μmol) was added and the mixture went bright pink. After standing 30 min on ice the product was extracted with chloroform (1 mL). The organic solution was washed to 10% aqueous sodium bromide (1 mL), dried over anhydrous $MgSO_4$ (~50 mg) and kept in the dark at −20° C. until required. The solvents were removed in vacuo to give red residue of the compound of formula (X). $^{31}$P NMR (chloroform-d$_1$) δ 1.867 compared with ethyltriphenylphosphonium bromide reference (δ=0 ppm).

The compound, herein referred to as MitoSNO, was found to have a high resolution mass spectrum of 380.1238 (calc. for C$_{22}$H$_{23}$PSNO is 380.1). The compound was also found to have an extinction coefficient of 16 L mol$^{-1}$ cm$^{-1}$ (at λ=549 nm).

EXAMPLE 2

Figure 2:
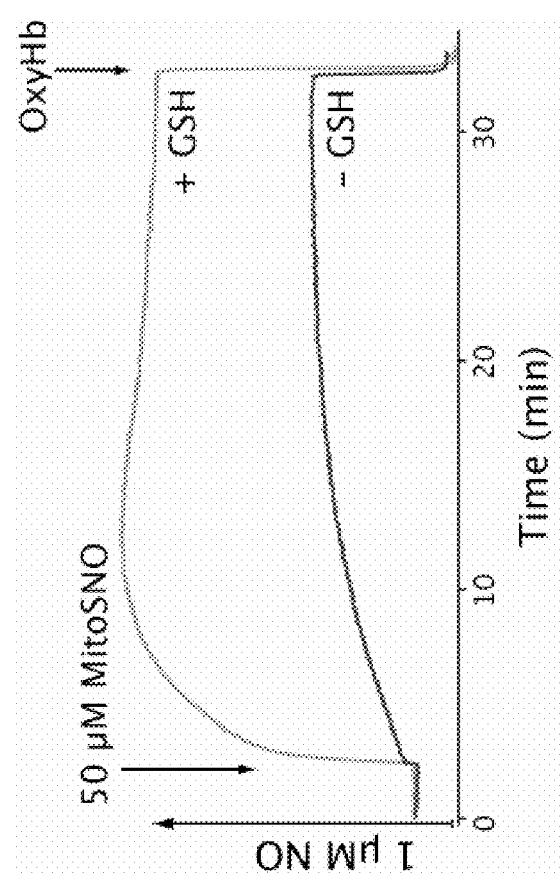
FIG. 2 is a trace showing NO release from a compound of the invention (MitoSNO) measured using a NO electrode in the presence and absence of glutathione (GSH). The trace shown is typical of two experiments.

An NO-selective electrode was used to demonstrate NO release from MitoSNO. 50 μM MitoSNO was incubated±10 mM GSH in KPi buffer, pH 8, at 37° C. for 30 min, then oxyhaemoglobin (5 μM) was added at the end of the incubation to degrade the free NO to nitrate (NO$_3^-$) and return the electrode response to the baseline. This showed that MitoSNO releases NO both in the presence and absence of GSH as can be seen in FIG. 2.

EXAMPLE 3

Rat liver mitochondria (1 mg protein/ml) in KCl buffer was incubated at 37° C. with 5 μM MitoSNO. 1 μM additions of MitoSNO were made sequentially before addition of 10 mM succinate. 200 nM FCCP was then added to uncouple the mitochondria. The concentrations of O$_2$ and MitoSNO in solution were measured simultaneously using a Clark-type O$_2$ electrode in combination with an ion-selective electrode for triphenylphosphonium cation (TPP$^+$). MitoSNO was found to be taken up by isolated mitochondria and inhibited respiration by NO release. This can be seen in FIG. 3.

Figure 3:
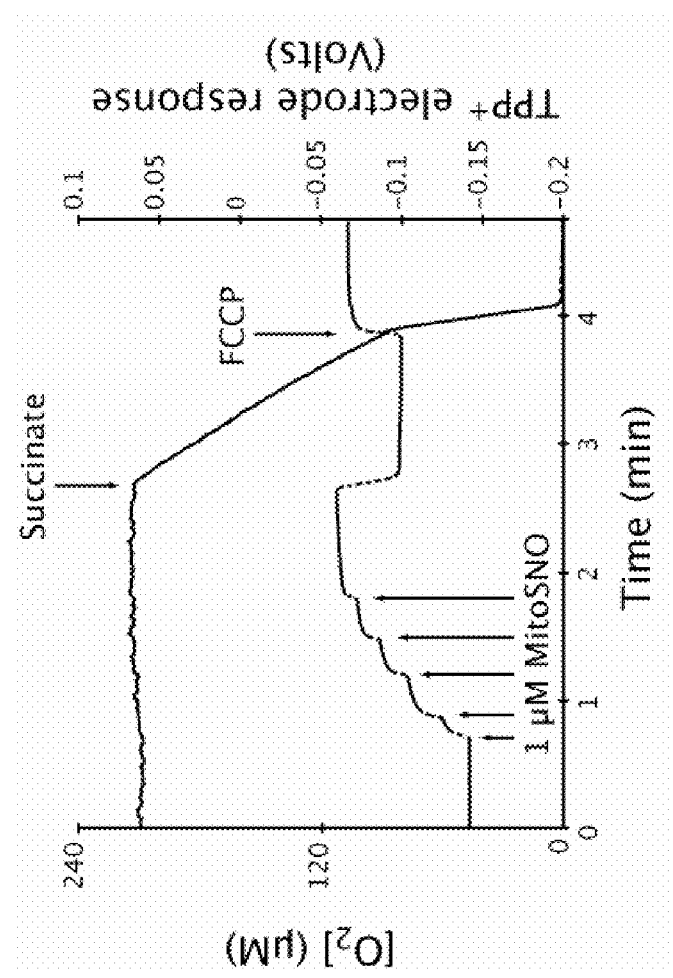
FIG. 3 is a trace showing MitoSNO uptake into energized respiring mitochondria in a Δψ-dependent manner. Oxygen (black trace) and TPP cation (dashed trace) concentrations were measured simultaneously. The trace shown is typical of two experiments.

When succinate was added, the mitochondria started respiring and set up a Δψ, which caused a decrease in the MitoSNO concentration, as detected by the ion-selective electrode (FIG. 3). When the mitochondria were uncoupled by FCCP, a concomitant increase in the concentration of MitoSNO, or its derivatives, in the medium was detected by the ion-selective electrode. The amount of MitoSNO taken up into the mitochondria from the trace in FIG. 3 corresponds to ~2.5 μM of the initial external concentration of 5 μM. Therefore 7.5 nmol MitoSNO have been taken up into 3 mg protein, and as the mitochondrial volume is ~0.5 μl/mg protein (Brown, G. C. and Brand, M. D. *Biochem J.*, 1985, 225, 399-405), the concentration of MitoSNO within mitochondria is ~5 mM. This represents a 2000 fold concentration relative to the 2.5 μM present in the external medium, and is consistent with a Nernstian uptake of MitoSNO.

EXAMPLE 4

Figure 4:
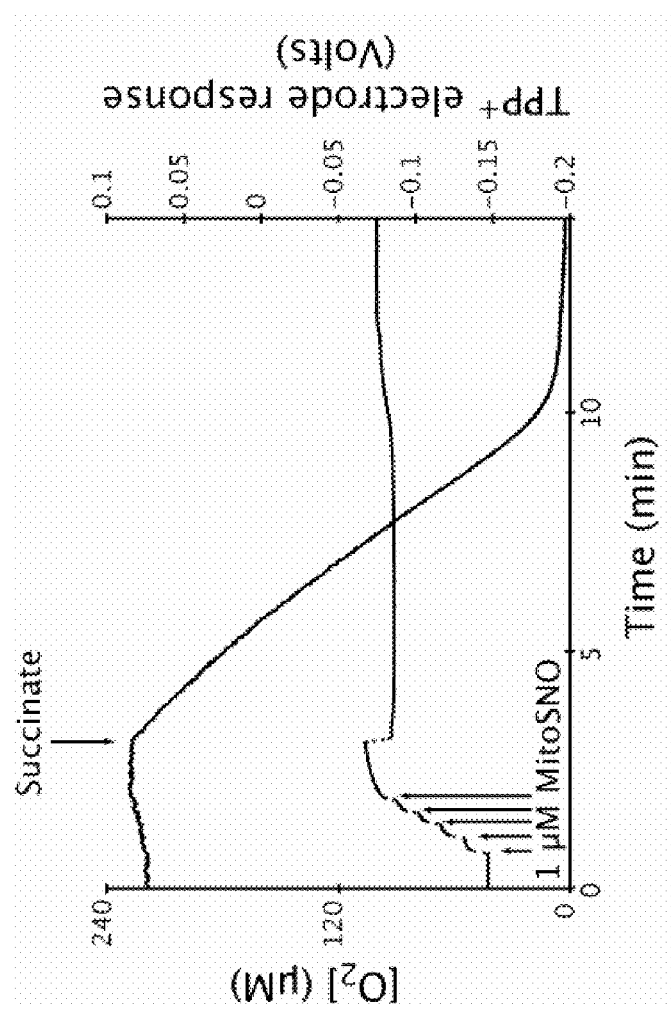
FIG. 4 is a trace showing MitoSNO uptake into respiring mitochondria in a Δψ-dependent manner. Oxygen (black trace) and TPP (triphenylphosphonium) cation (dashed trace) concentrations were measured. The trace shown is typical of two experiments. MitoSNO uptake leads to production of NO inside the mitochondria which gradually inhibits respiration, as indicated by the shape of the oxygen electrode trace. This also decreases the membrane potential, as shown by the decreased uptake of MitoSNO.

To show that MitoSNO released NO within energized mitochondria and inhibited mitochondrial respiration, 5 μM MitoSNO was incubated with a low concentration of rat liver mitochondria (0.5 mg protein/ml) in KCl buffer at 37° C., to enable a longer incubation period in order for sufficient NO release from MitoSNO to affect respiration. 1 μM additions of MitoSNO were made sequentially before addition of 10 mM succinate. The mitochondria were then allowed to respire until oxygen consumption reached a plateau. At low oxygen concentrations, inhibition of respiration and a concomitant gradual redistribution of MitoSNO, or its derived TPP cations, to the extramitochondrial solution through decreased Δψ were observed (FIG. 4).

EXAMPLE 5

A compound of formula (XI) was prepared as described in Scheme 6 above.

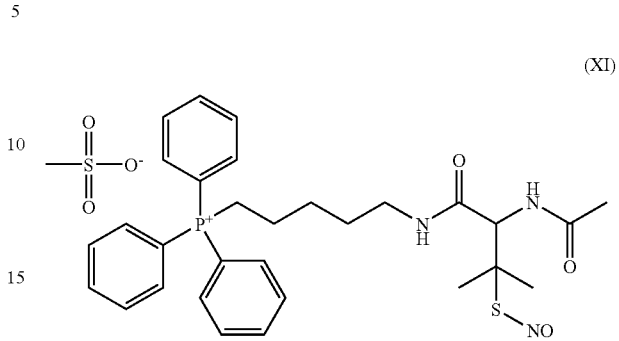

(XI)

A solution of 5-aminopentyltriphenylphosphonium bromide hydrogen bromide (McAllister, P. R.; Dotson, M. J.; Grim, S. O.; Hillman, G. R. *Journal of Medicinal Chemistry* 1980, 23, pp 862-5) (467 mg, 0.917 mmol) and triethylamine (136 μL, 0.920 mmol) in dichloromethane (10 mL) was stirred for 5 min after which time a solution of N-(2,2-Dimethyl-4-oxo-thietan-3-yl)-acetamide (Moynihan, H. A., Roberts, S. M. *Journal of the Chemical Society, Perkin Transactions* 1: *Organic and Bio-Organic Chemistry* (1972-1999) 1994, pp 797-805) (157 mg, 0.917 mmol) in dichloromethane (20 mL) was added in one aliquot and the reaction mixture was stirred for a further 4 h. After the mixture had been washed with a saturated solution of sodium methanesulfonate (3×20 mL), the organic fraction was collected, dried (MgSO$_4$), filtered and the solvents removed in vacuo to give pale yellow oil. The oil was dissolved in minimal dichloromethane (2 mL) and then excess diethyl ether (70 mL) was added. After the resultant precipitate had settled, the solvents were decanted and the residue was dried in vacuo (0.1 mmHg) for 2 h to give a thiol as a cream powder (374 mg, 0.607 mmol, 66%). HRPI ESMS (CE) calculated for C$_{30}$H$_{38}$N$_2$O$_2$PS$^+$: 521.2386, found: 521.2397. Analysis calculated for C$_{31}$H$_{41}$N$_2$O$_5$PS$_2$: C 60.4, H 6.7, N 4.5, S 10.4%; found C 59.8, H 6.9, N 4.8, S 10.2%. UV-vis: 2.7 mg in 10 mL ethanol, ε$_{268}$ 2660 Lmol$^{-1}$ cm$^{-1}$, ε$_{275}$ 2292 Lmol$^{-1}$ cm$^{-1}$. $^1$H NMR (chloroform-d$_1$) δ 7.94 (1H, t, J=5 Hz, CH$_2$—NH), 7.82-7.62 (16H, m, ArH, CH—NH), 4.67 (1H, d, J=10 Hz, CH), 3.58-3.47 (2H, m, CH$_2$—P$^+$), 3.42-3.27 (1H, m, CHH—NH), 3.27-3.14 (1H, m, CHH—NH), 2.76 (3H, s, SO$_3$—CH$_3$), 2.69 (1H, s, SH), 2.13 (3H, s, CO—CH$_3$), 1.55 (3H, s, CH$_3$), 1.43 (3H, s, CH$_3$), 1.80-1.52 (6H, m, CH$_2$) ppm. $^{13}$C NMR (chloroform-d$_1$, 125 MHz) δ170.7, (CO), 170.3, (CO), 135.1 (d, J=3 Hz, para-Ph), 133.6 (d, J=10 Hz, meta-Ph), 130.6 (d, J=13 Hz, ortho-Ph), 118.5 (d, J=86 Hz, ipso-Ph), 62.3 (CH), 46.5 (C), 39.8 (CH$_3$—SO$_3^-$), 38.2 (CH$_2$—NH), 30.7 (CH$_3$), 30.6, (CH$_3$), 27.6 (CH$_2$—CH$_2$NH), 27.1 (d, J=17 Hz, CH$_2$—CH$_2$—P$^+$), 23.4 (CH$_3$), 22.0 (d, J=53 Hz, CH$_2$—P$^-$), 21.9 (d, J=5 Hz, CH$_2$—CH$_2$—CH$_2$—P$^+$) ppm. $^{31}$P NMR (chloroform-d$_1$) δ 25.4 ppm. HPLC: mobile phase 50% acetonitrile, 50% water (0.1% trifluoroacetic acid); Prodigy 5μ OD53 11A 250×4 mm, detection 275 nm, flow rate 1.00 mL/min; retention time 4.76 min, one peak.

A sample of the thiol (50 mg, 0.081 mmol) was dissolved in ethanol (2 mL) flushed with argon and stored in the dark. Methane sulfonic acid stock (0.576 mL, 357 mmol) was added and the reaction vessel swirled for 1 min then aqueous sodium nitrite (0.420 mL, 323 mmol) was added and the reaction vessel was swirled again. The reaction mixture was held in the dark for 2 hr at room temperature. Dichloromethane (2 mL) was then added and the mixture was gently shaken for 10 sec. Distilled water (2 mL) was added and the reaction mixture was left to stand for 20 sec and the lower dichloromethane layer was removed and dried over anhydrous $MgSO_4$ (~200 mg). The dichloromethane solution was then filtered and evaporated (30° C., 2 mmHg) The green glassy residue was dissolved in minimal dichloromethane (0.5 mL) and added to diethyl ether(40 mL). The resulting pale green precipitate was isolated by decantation and drying under vacuum (2 mmHg) and in the dark to yield the product (V) (40 mg, 78%). HPLC. 50% acetonitrile, 50% water (0.1% trifluoroacetic acid); Prodigy 5μ OD53 11A 250×4 mm, detection 275 nm, flow rate 1.00 mL/min; retention time 8.17 min, one peak. UV-vis: ethanol $\lambda_{max}$=268 nm (ε 3191 $Lmol^{-1}cm^{-1}$), λ=275 nm (ε 2730 $Lmol^{-1}cm^{-1}$), λ=344 nm (ε 601 $Lmol^{-1}cm^{-1}$). HRPI ESMS (CE) (CE 6V, QIE 3V) calculated for $C_{30}H_{37}N_3O_3PS$: 550.229, found: 550.226. $^1H$ NMR δ (methanol-$d_4$): 8.38 (1H, bt, $CH_2$—NH), 7.73-7.92 (15H, m, Ar—H), 5.30 (1H, d, J=10 Hz, CH), 3.47-3.35 (2H, m, $P^+$—$CH_2$), 3.22-3.07 (2H, m, $CH_2$—NH), 2.68 (3H, s, $CH_3$—$SO_3^-$), 2.03 (3H, s, $CH_3$), 1.99 (3H, s, $CH_3$), 1.96 (3H, s, $CH_3$), 1.88-1.40 (6H, m, $CH_2$) ppm. $^{13}C$ NMR δ (methanol-$d_4$, 125 MHz): 173.1 (CO), 170.8 (CO), 136.3 (d, J=3 Hz, para-Ph), 134.8 (d, J=10 Hz, meta-Ph), 131.5 (d, J=13 Hz, ortho-Ph), 119.9 (d, J=86 Hz, ipso-Ph), 61.7 (CH), 59.2 (C), 39.8 ($CH_2$—NH), 39.5 ($CH_3$—$SO_3^-$), 29.3 ($CH_2$—$CH_2$—NH), 28.7 (d, J=17 Hz, $CH_2$—$CH_2$—$P^+$), 27.1 ($CH_3$), 25.9, ($CH_3$), 23.0 (d, J=9 Hz, $CH_2$—$CH_2$—$CH_2P^+$), 22.7 (d, J=56 Hz, $CH_2$—$P^+$), 22.4 ($CH_3$) ppm. $^{31}P$ NMR δ (methanol-$d_4$) 24.9 ppm. This compound, [5-(2-acetylamino-3-methyl-3-nitrosothio-butyrylamino)-penty1]-triphenylphosphonium methanesulfonate, is herein referred to as MitoSNAP.

EXAMPLE 6

Figure 5:
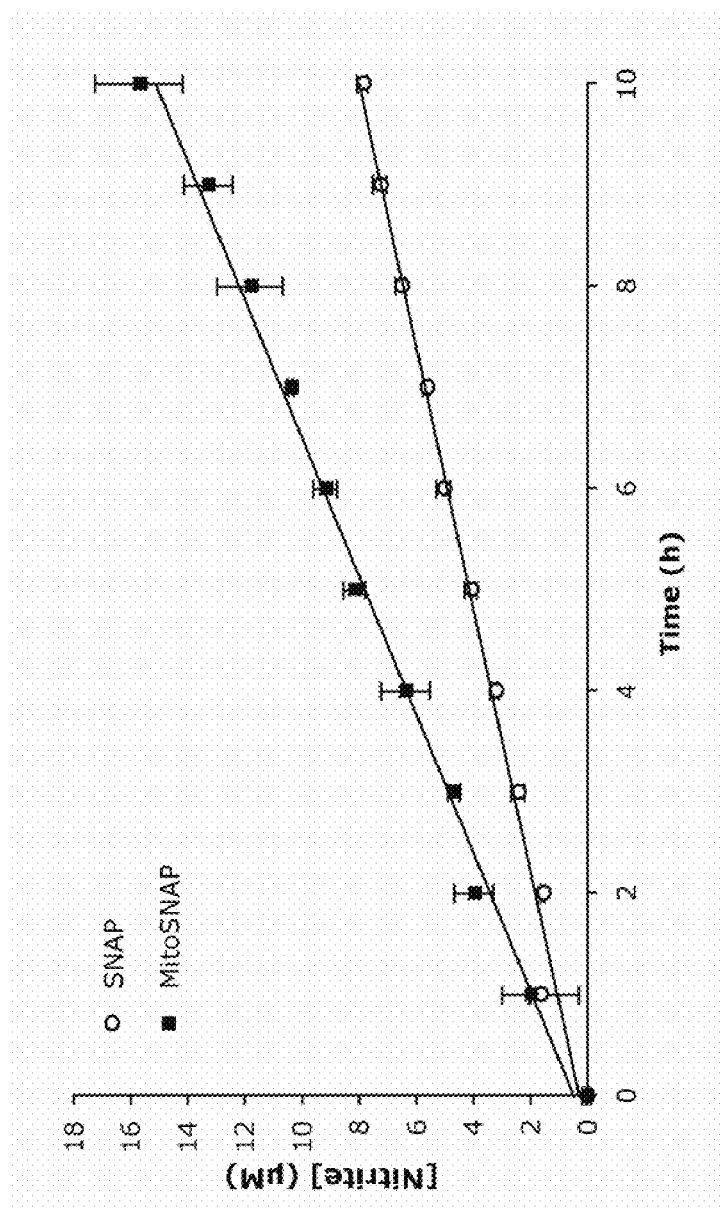
FIG. 5 is a graph showing the concentration of nitrate formed over time from a compound of the invention (MitoSNAP) compared to SNAP. The NO released from MitoSNAP reacts with oxygen to form nitrite.
Figure 6:
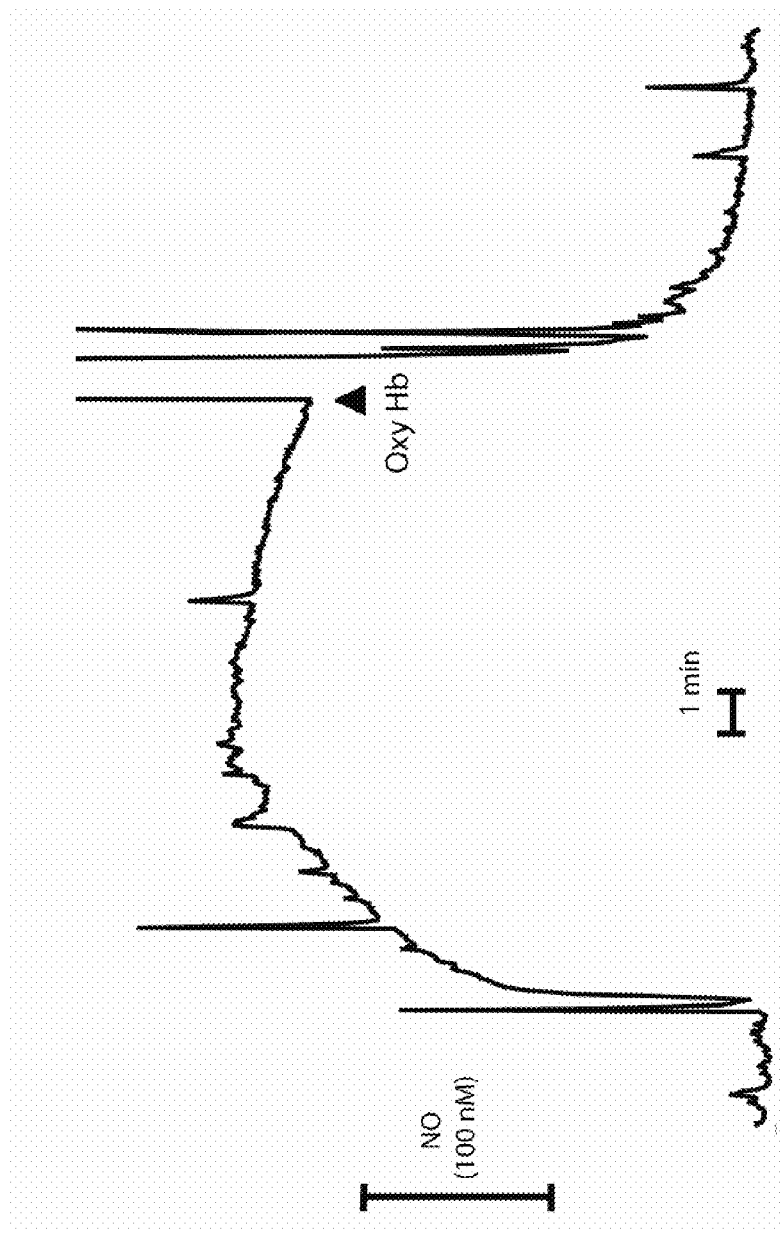
FIG. 6 is a trace showing release of NO from MitoSNAP, as assessed by measuring the formation of NO with an NO electrode then degrading the NO to nitrate by addition of oxyhemoglobin (Oxy Hb).
Figure 7:
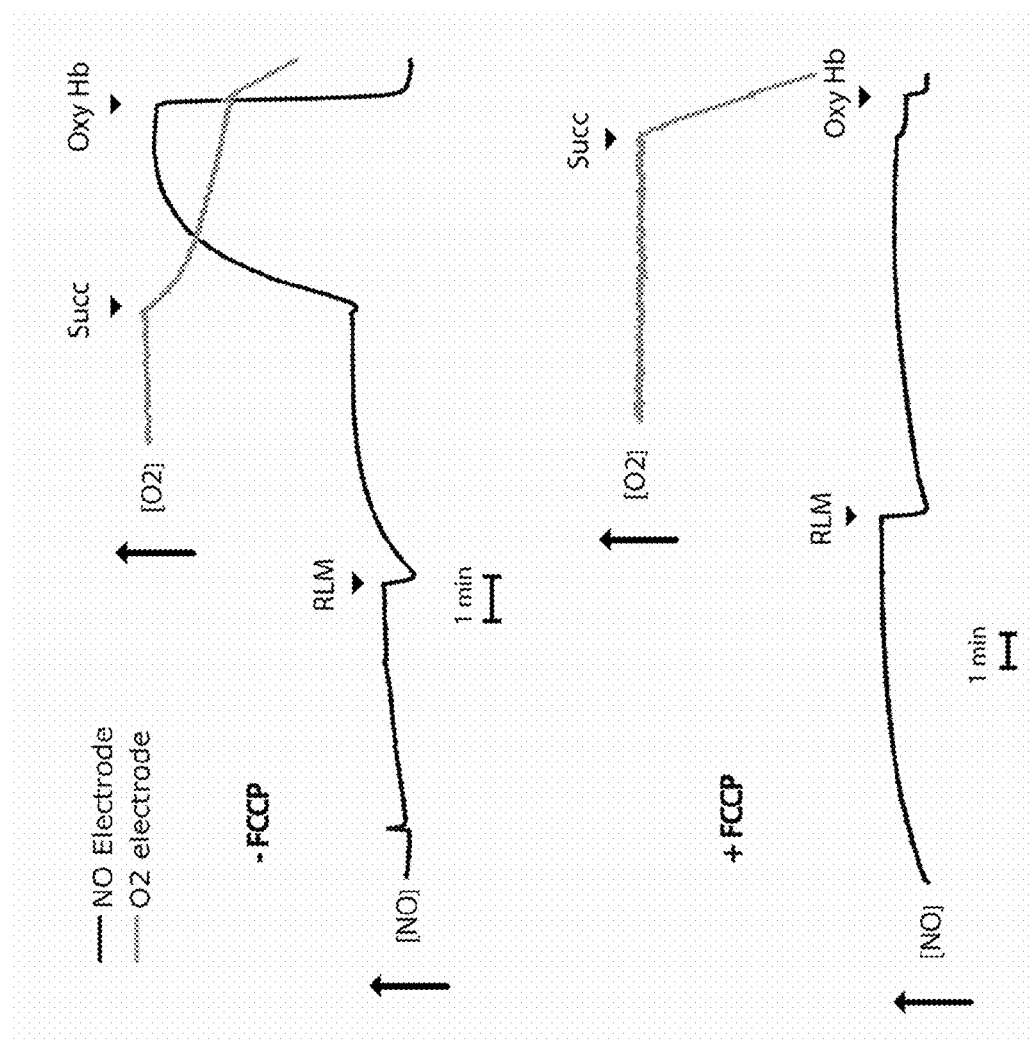
FIG. 7 is a trace showing the interaction of isolated mitochondria with MitoSNAP. The trace shows the results from an NO-electrode (measuring NO) and an oxygen electrode (measuring respiration of the mitochondria). In the upper trace, addition of succinate to energise the mitochondria leads to a large increase in NO formation due to accumulation of MitoSNAP into the mitochondria and subsequent NO release. The released NO then interacts with cytochrome oxidase to decrease respiration, as indicated by the curving off of the oxygen electrode trace. In contract, in the lower trace, the effects of MitoSNAP on NO production and inhibition of respiration are much lower in the presence of uncoupling molecules FCCP. FCCP abolishes the membrane potential preventing uptake of MitoSNAP into the mitochondria.

To show that MitoSNAP could spontaneously release NO, S-nitroso-N-acetyl-DL-penicillamine (SNAP) (50 μM) or MitoSNAP (50 μM) was incubated at 37° C. in opaque tubes in KCl buffer (120 mM KCl, 10 mM HEPES, 1 mM Ethylenebis(oxyethylenenitrilo)tetraacetic acid (EGTA)) with 100 μm Diethylenetriaminepentaacetic acid (DTPA) and Neocuproine (10 μM) that had been treated with Chelex (1%). Samples were taken hourly and snap frozen on dry ice. Samples were thawed and assayed for nitrite concentration using the Griess assay. Data are means of triplicate determinations of a single experiment that was repeated 3× with similar results (FIG. 5).

EXAMPLE 7

To show that MitoSNAP could release NO, nitrogen purged KCl buffer (as above) at 37° C. was incubated in the stirred chamber of a nitric oxide electrode (WPI Ltd). MitoSNAP (100 μM) was added and the formation of NO measured by the NO electrode. Where indicated oxyhaemoglobin (~5 μM) was added to degrade all the accumulated NO to nitrate.

EXAMPLE 8

To see the interaction of MitoSNAP with mitochondria, rat liver mitochondria (1 mg protein/ml) were incubated KCl buffer (as above) supplemented with rotenone (4 μg/ml) ±FCCP (0.5 μM) at 37° C. and the oxygen and NO concentrations were measured using appropriate electrodes. For the incubation without FCCP, MitoSNAP (50 μM) was added followed by succinate (10 mM) which induced a mitochondrial membrane potential leading to the uptake of MitoSNAP inside mitochondria which led to its activation by thiols within mitochondria and to the release of large amounts of NO. This NO led to the inhibition of respiration at cytochrome oxidase and this was reversed by the addition of oxyhaemoglobin (~5 μM) to degrade all accumulated NO to nitrate.

EXAMPLE 9

Membrane Potential-Dependent Mitochondrial Uptake of MitoSNAP and NO• Release

Figure 8:
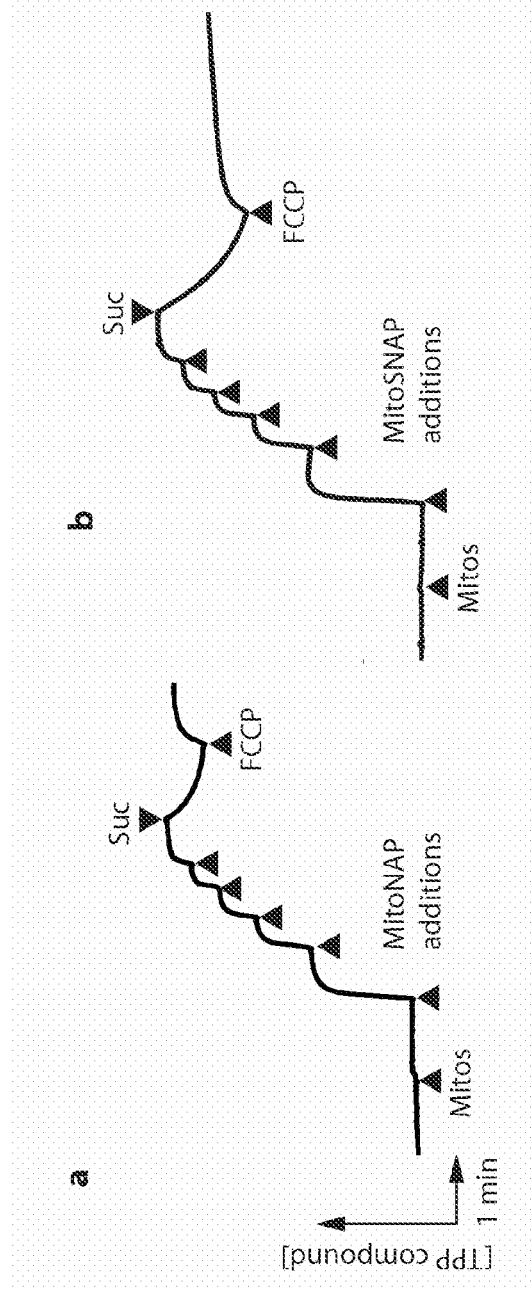
FIG. 8 is a trace showing the uptake of MitoSNAP and MitoNAP by energized mitochondria measured using an ion-selective electrode. For (a) and (b) mitochondria (2 mg protein/ml) were incubated in KCl buffer supplemented with rotenone in a stirred 3 ml chamber thermostatted at 37° C. and shielded from ambient light. An electrode selective for the TPP cation was inserted and calibrated by five sequential 1 μM additions of MitoNAP (a) or MitoSNAP (b). Succinate (10 mM) was then added to energize the mitochondria, followed by the uncoupler FCCP (0.5 μM). Rapid uptake of MitoNAP by energized mitochondria was observed and this was reversed by abolishing the membrane potential with the uncoupler FCCP (a). Energised mitochondria also rapidly accumulated MitoSNAP (b). However, in contrast to MitoNAP, uncoupling apparently led to only partial release of the accumulated MitoSNAP (b). This apparent incomplete release of MitoSNAP on uncoupling is presumably because MitoSNAP is converted to MitoNAP within mitochondria and this generates a different response from the electrode.
Figure 9:
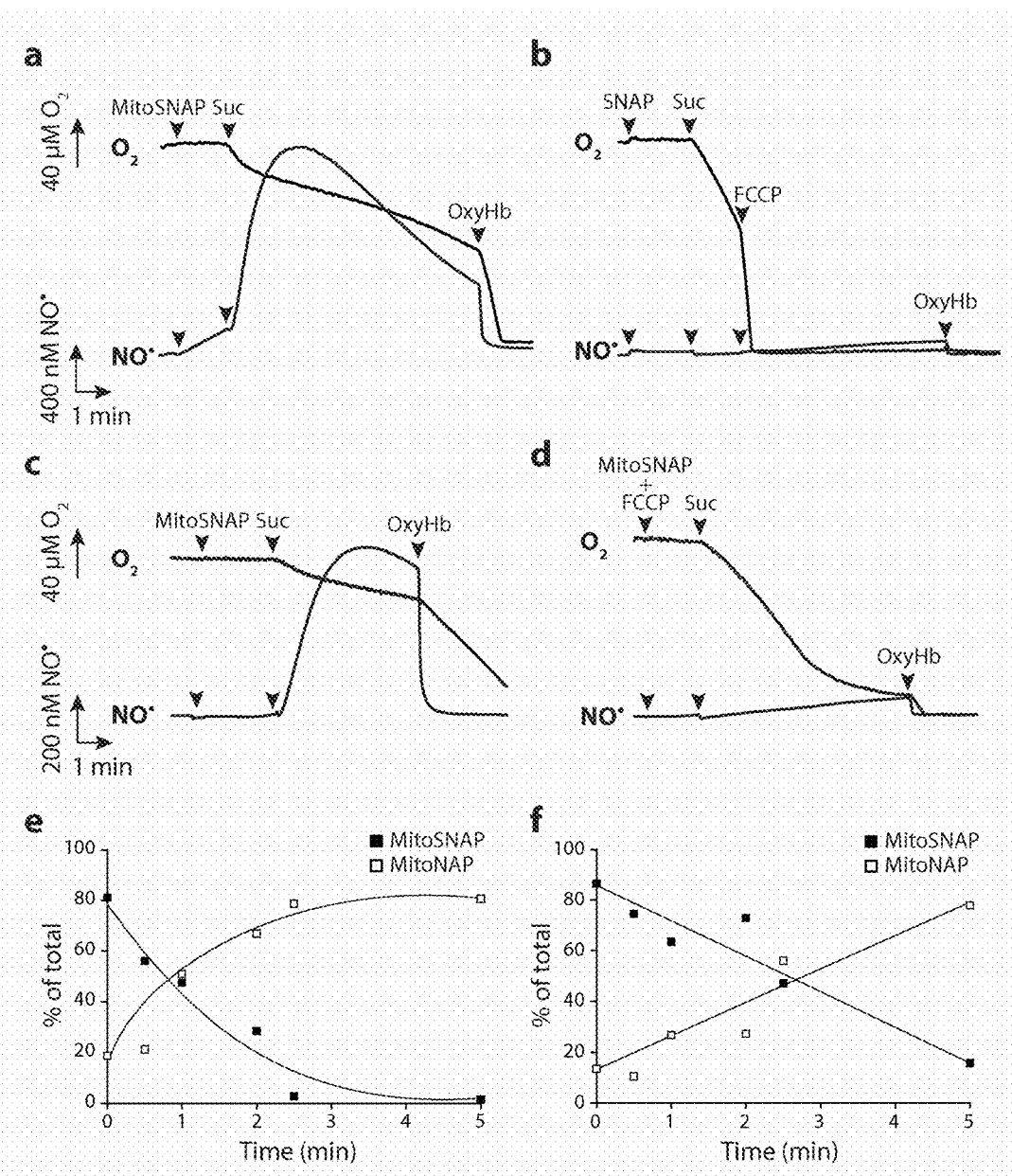
FIG. 9 is a series of traces and graphs showing membrane potential-dependent MitoSNAP mitochondrial uptake and NO˙ generation. (a-d) Liver mitochondria were incubated in KCl medium supplemented with rotenone in a stirred 3 ml chamber and electrodes were used to measure the concentrations of $O_2$ and $NO^\bullet$ simultaneously. Where indicated succinate (10 mM), OxyHb (5 μM) or FCCP (500 nM) were added. For (a) and (b) 2 mg mitochondrial protein/ml and 20 μM MitoSNAP (a) or SNAP (b) were used. For (c) and (d) 0.5 mg mitochondrial protein/ml and 5 μM MitoSNAP were used. There was no effect of 5 μM MitoNAP on respiration or $NO^\bullet$ production. All traces are from typical experiments repeated at least twice. (e-f) Mitochondria (1 mg protein) were incubated in 1 ml KCl medium without neocuproine or DTPA, supplemented with rotenone and succinate in the absence (e) or presence (f) of FCCP (500 nM). Mitochondria were then pelleted by centrifugation (10,000×g) then aliquots of the supernatant (700 μl) were mixed with 700 μl 0.1% TFA and analyzed by RP-HPLC. The amount of MitoSNAP and MitoNAP were calculated as the percentage of their peak areas relative to the sum of both peak areas.

By using a TPP-selective electrode (Asin-Cayuela, J., Manas, A. R., James, A. M., Smith, R. A. & Murphy, M. P. Fine-tuning the hydrophobicity of a mitochondria-targeted antioxidant. *FEBS Letts.* 571, 9-16 (2004)) a significant Δψ-dependent uptake of MitoSNAP into isolated mitochondria was observed (FIG. 8). Following its accumulation within mitochondria MitoSNAP interacted with the GSH-rich matrix to release NO• which then affected respiration by competitively inhibiting $O_2$ consumption at cytochrome c oxidase. This was demonstrated by using NO• and $O_2$ electrodes to measure respiration rate and NO• concentration simultaneously (FIG. 9). Mitochondria were incubated with the complex I inhibitor rotenone in the absence of substrate to prevent Δψ generation, and addition of 20 μM MitoSNAP produced a small amount of NO•, presumably due to MitoSNAP diffusion into the mitochondrial matrix and reaction with GSH (FIG. 9a). Addition of the respiratory substrate succinate initiated $O_2$ consumption and generated a Δψ, leading to a rapid increase in NO• production due to the accumulation of MitoSNAP within mitochondria and its reaction with GSH (FIG. 9a). The respiration rate slowed as NO• accumulated and this inhibition was reversed by degrading NO• with the addition of OxyHb, indicating that the respiratory inhibition was due to the reversible competition between NO• and $O_2$ at cytochrome c oxidase (FIG. 9a). As expected, addition of 20 μM MitoNAP, which lacks the SNO function, had no effect on respiration or the NO• electrode response. In contrast to MitoSNAP, the amount of NO• generated by 20 μM SNAP in the presence of energized mitochondria was negligible and did not affect respiration (FIG. 9b), presumably because it did not selectively enter the mitochondria.

To explore further the Δψ-dependence of NO• production by MitoSNAP, studies with decreased concentrations (5 μM) and fewer mitochondria (0.5 mg protein/ml) were undertaken (FIGS. 9c & d). Under these conditions the initial production of NO• from MitoSNAP was negligible, but subsequent mitochondrial energization with succinate led to a dramatic increase in NO• production (FIG. 9c). The build up of NO• decreased respiration and this was reversed by OxyHb, consistent with reversible inhibition of cytochrome c oxidase by NO• (FIG. 9c). Inclusion of the uncoupler carbonyl cyanide p-trifluoromethoxyphenylhydrazone (FCCP) in the incubation resulted in decreased NO• production as the Δψ was largely abolished, preventing the uptake of MitoSNAP into mitochondria (FIG. 9d). The decreased accumulation of NO• in the presence of FCCP still inhibited respiration, but in this case inhibition occurred at a lower $O_2$ concentration, again consistent with a competitive interaction between NO• and $O_2$ at cytochrome c oxidase (FIG. 9d). The metabolism of MitoSNAP by mitochondria was investigated by pelleting the mitochondria at various times and analyzing the amounts of MitoSNAP and MitoNAP in the supernatant by RP-HPLC as shown in (FIGS. 9e & f). Energized mitochondria rapidly consumed MitoSNAP and converted it to MitoNAP (FIG.

9e), while for unenergized mitochondria the conversion of MitoSNAP to MitoNAP was slower (FIG. 9f).

In summary, MitoSNAP is rapidly accumulated by energized mitochondria, driven by the $\Delta\psi$, and once inside the matrix it interacts with GSH and other thiols to produce $NO^\bullet$ and MitoNAP. The $NO^\bullet$ thus generated competes with $O_2$ for the active site of cytochrome c oxidase, reversibly inhibiting respiration. MitoSNAP is a $\Delta\psi$-dependent source of intramitochondrial $NO^\bullet$ that can reversibly modulate mitochondrial $O_2$ consumption, particularly at low $O_2$ concentrations.

EXAMPLE 10

Figure 10:
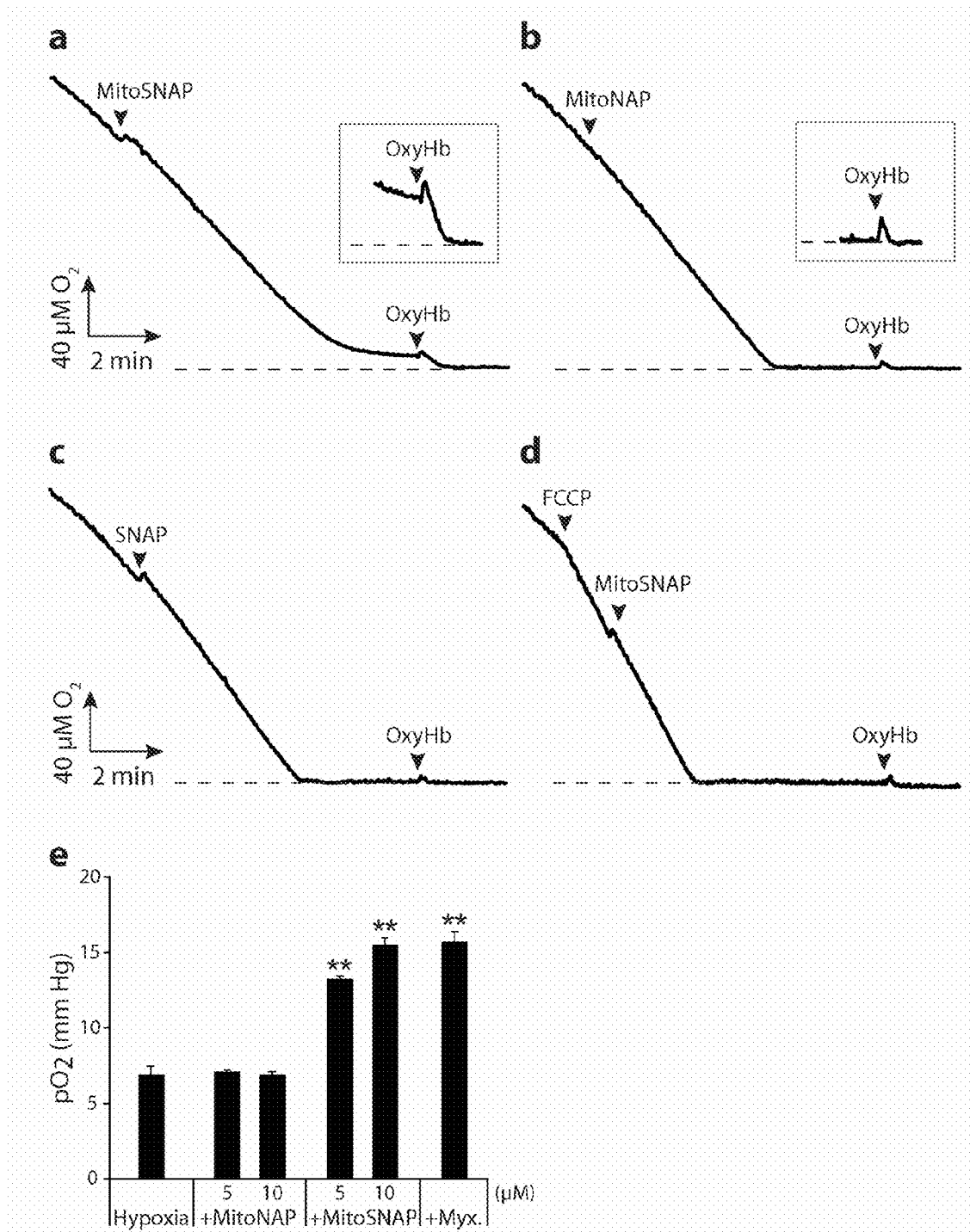
FIG. 10 is a series of traces and graphs showing the effect of MitoSNAP on respiration in cells. (a-d) Jurkat cells (55× $10^6$ cells) were incubated in PBS supplemented with 25 mM Hepes pH 7.2 (NaOH), 1 mM sodium pyruvate, 10 μM neocuproine and 100 μM DTPA in the stirred 2.5 ml chamber of an oxygen electrode at 37° C. with 5 μM MitoSNAP (a), MitoNAP (b), SNAP (c) or MitoSNAP and FCCP (500 nM) (d). Where indicated 5 μM OxyHb was added. Traces show typical experiments that were repeated at least three times. Sections of the $O_2$ electrode trace where OxyHb was added for (a) and (b) have been expanded 4-fold in the vertical dimension to facilitate inspection. In all traces the dashed line indicates anaerobiosis. (e) Effect of MitoSNAP on $O_2$ bioavailability in hypoxia. HeLa cells were incubated at 1% $O_2$ concentration with 5% $CO_2$ and the balance $N_2$ for 60 mM before the indicated treatments. Cellular $pO_2$ values, measured by fluorescence quenching oximetry and expressed as mean±sd, are shown. (**$p<0.001$ compared to hypoxia alone and to MitoNAP treatments by ANOVA).

Uptake of MitoSNAP by Cells Leads to $NO^\bullet$ Generation and Respiratory Inhibition To evaluate the selective uptake of MitoSNAP by mitochondria within cells, the effect of MitoSNAP on respiration by Jurkat cells, a T lymphocyte cell line that grows in suspension, was measured using an $O_2$ electrode (FIG. 10). There was no initial effect on respiration rate after addition of MitoSNAP, but as the cells consumed more $O_2$ the respiration rate decreased and approached zero even though there was still considerable $O_2$ remaining (FIG. 10a). This inhibition was reversible and was shown to be due to $NO^\bullet$, as degradation with OxyHb restored the maximal respiration rate and allowed the $O_2$ concentration to reduce to zero (FIG. 10a). It was noteworthy that at low $O_2$ concentrations the $NO^\bullet$ generated by MitoSNAP was sufficient to prevent mitochondrial oxygen consumption almost entirely and maintain a low $O_2$ concentration for at least 30 min in this system. This is clearly illustrated in the expanded section of the $O_2$ electrode trace in FIG. 10a, which shows that addition of OxyHb restores respiration causing the $O_2$ concentration to rapidly decrease to zero by degrading $NO^\bullet$. In contrast, MitoNAP did not affect respiration, as shown by the $O_2$ electrode trace decreasing rapidly to zero (FIG. 10b). SNAP also had no effect on respiration (FIG. 10c), and addition of the uncoupler FCCP prior to MitoSNAP prevented the inhibition of respiration (FIG. 10d). The effective $K_m$ of cytochrome c oxidase for $O_2$ is very low (<1 µM) (Wikstrom, M., Krab, K. & Saraste, M. *Cytochrome oxidase—a synthesis* London: Academic press (1981)), illustrated by the sharp transition from maximal $O_2$ consumption to zero respiration in FIG. 10b. This contrasts with the situation in the presence of MitoSNAP (FIG. 10a) where there is a gradual decline in $O_2$ consumption rate. These findings are consistent with the $\Delta\psi$-dependent uptake of MitoSNAP into mitochondria within cells facilitating $NO^\bullet$ release which slows respiration through the competitive inhibition between $NO^\bullet$ and $O_2$ at cytochrome c oxidase, which becomes more effective as the $O_2$ concentration decreases. These results support the proposal that the reversible inhibition of cytochrome c oxidase by the $NO^\bullet$ produced from MitoSNAP may increase $O_2$ bioavailability during hypoxic conditions. To explore this further, HeLa cells were maintained in a humidified hypoxia workstation at 1% $O_2$ concentration with 5% $CO_2$ and the balance $N_2$ for 60 min. Then the effects of a further 30 min incubation with MitoSNAP, MitoNAP or the mitochondrial inhibitor myxathiazol on the steady-state extracellular $pO_2$ was assessed by fluorescence quenching oximetry (FIG. 10e). MitoSNAP and the mitochondrial inhibitor myxathiazol both increased extracellular $O_2$ during hypoxia compared to untreated controls, while MitoNAP had no effect (FIG. 10e). This demonstrates that $NO^\bullet$ production by MitoSNAP within the mitochondria of hypoxic cells can be used to slow respiration sufficiently to modulate cytosolic $O_2$ concentration.

EXAMPLE 11

S-Nitrosation of Mitochondrial Protein Thiols by MitoSNAP

Figure 12:
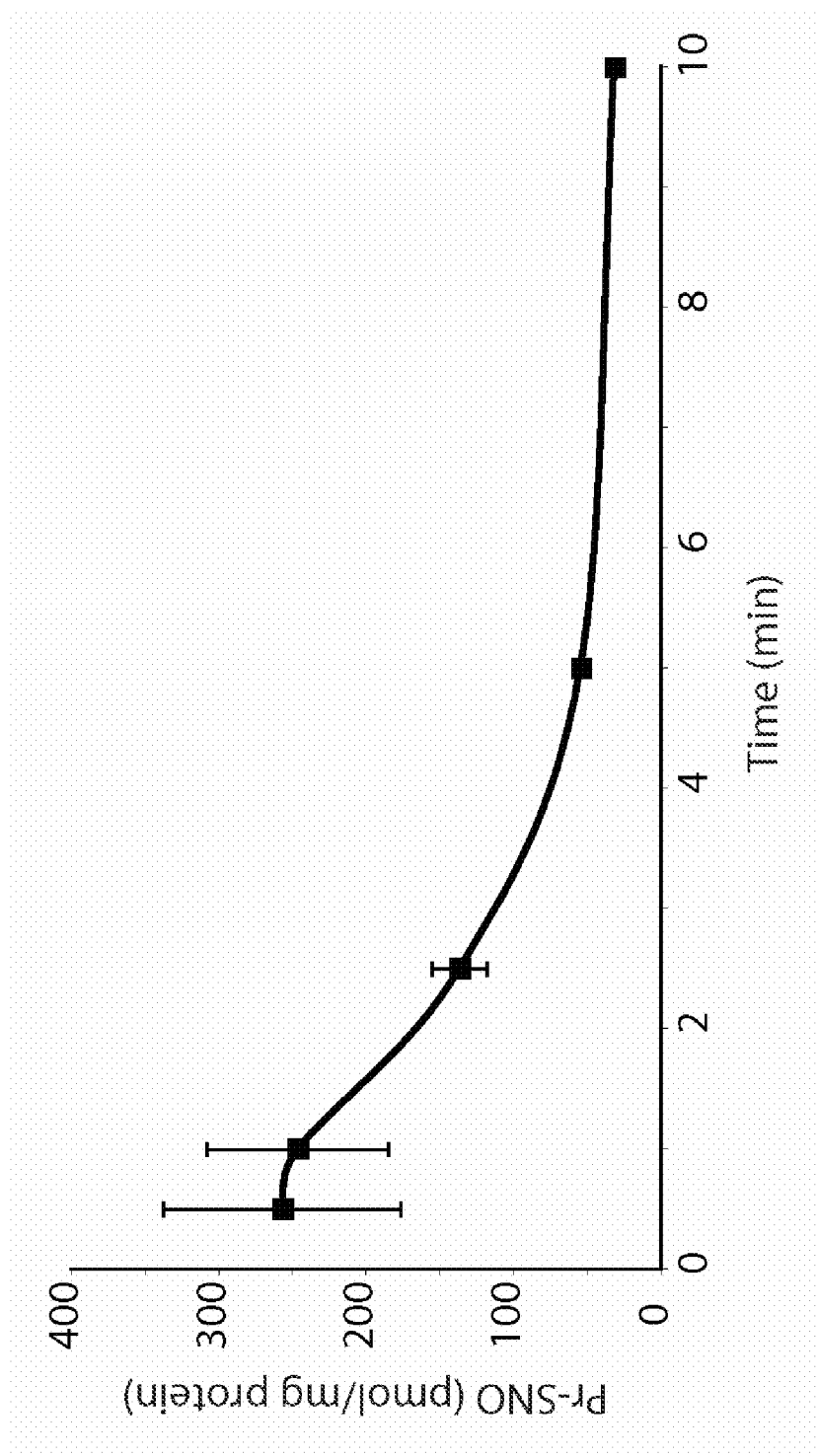
FIG. 12 is a graph showing the effect of OxyHb on S-nitrosation of mitochondrial thiols by MitoSNAP. Time course of S-nitrosation of mitochondrial proteins by MitoSNAP. Aliquots of liver mitochondria (1 mg protein/ml) were incubated at 37° C. in 1 ml KCl buffer supplemented with rotenone and succinate in the presence of 5 μM MitoSNAP and 5 μM OxyHb and at various times mitochondria were treated with 10 mM NEM and isolated by centrifugation and the S-nitrosothiol content assessed. Data are of a typical experiment showing means±range of duplicate samples for each time point, each measured in duplicate. The experiment was repeated twice with the same result.
Figure 13:
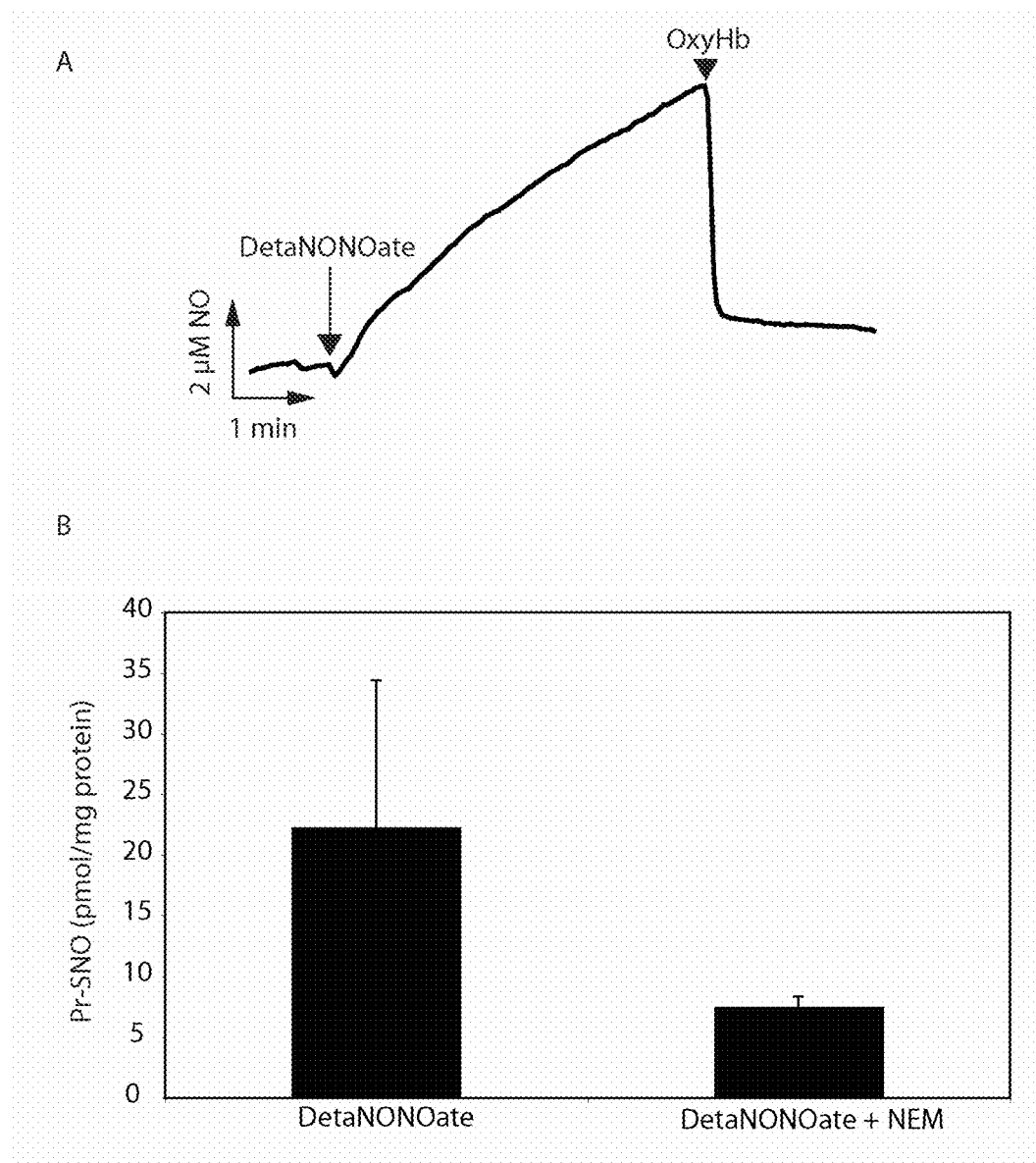
FIG. 13 is a trace and graph showing limited S-nitrosation of mitochondria by DetaNONOate. (a) Rat liver mitochondria (1 mg protein/ml) were incubated in KCl medium supplemented with rotenone and succinate at 37° C. in the 3 ml stirred chamber of an $NO^\bullet$ electrode. Where indicated 500 μM DetaNONOate was added and the concentration of $NO^\bullet$ was measured over time, before 5 μM OxyHb was added. B. Rat liver mitochondria (1 mg protein/ml) were incubated in 1 ml KCl medium supplemented with rotenone and succinate at 37° C. with 500 μM DetaNONOate for 5 min. Then protein pellets were resuspended and processed for analysis of protein S-nitrosothiols. Control incubations in the presence of 10 mM NEM were also carried out. Data are means±range of two independent experiments each being the average of four mitochondrial incubations.

To evaluate the S-nitrosation of mitochondrial thiol proteins by MitoSNAP, MitoSNAP was incubated with isolated mitochondria and a sensitive chemiluminescence assay was employed to measure SNOs (Feelisch, M. et al. Concomitant S—, N—, and heme-nitros(yl)ation in biological tissues and fluids: implications for the fate of NO in vivo. *FASEB. J.* 16, 1775-85 (2002)). S-nitrosation of mitochondrial proteins by MitoSNAP was found to peak over 2-3 min and then gradually decline (FIG. 11a), consistent with the metabolism of MitoSNAP by energized mitochondria seen in FIG. 9. Incubation of mitochondria with MitoSNAP for 2.5 min showed extensive, concentration-dependent S-nitrosation of mitochondrial proteins that was largely blocked by abolishing the $\Delta\psi$ with the uncoupler FCCP (FIG. 11b). In contrast, SNAP, even at 50 µM, led to negligible S-nitrosation (FIG. 11b). Functionalization of the free protein thiols by preincubation of mitochondria with the thiol alkylating agent N-ethyl maleimide (NEM) blocked S-nitrosation by MitoSNAP (FIG. 11b). Incubations in the absence of free $NO^\bullet$, achieved by addition of excess OxyHb, still led to extensive mitochondrial S-nitrosation FIG. 12. Incubation of mitochondria with 500 µM of the $NO^\bullet$-donor 3,3-bis(aminoethyl)-1-hydroxy-2-oxo-1-tri azene (Deta-NONOate), which spontaneously hydrolyzes to generate a five to ten-fold greater $NO^\bullet$ concentration than 5 µM MitoSNAP (FIG. 13a) but does not transnitrosate thiols (Dahm, C. C., Moore, K. & Murphy, M. P. Persistent S-nitrosation of complex I and other mitochondrial membrane proteins by S-nitrosothiols but not nitric oxide or peroxynitrite: Implications for the interaction of nitric oxide with mitochondria. *J. Biol. Chem.* (2006) 281, 10056-10065), gave ~20 pmol SNO/mg protein, ~30-fold less than that caused by 5 µM MitoSNAP (FIG. 13b). The contribution of free $NO^\bullet$ to S-nitrosation by MitoSNAP is thus seen as minor. In other words, MitoSNAP leads to the extensive S-nitrosation of mitochondrial thiol proteins following its $\Delta\psi$-dependent uptake into the matrix and this S-nitrosation is predominantly due to the direct transfer of $NO^+$ from MitoSNAP to thiolates within the matrix.

Figure 14:
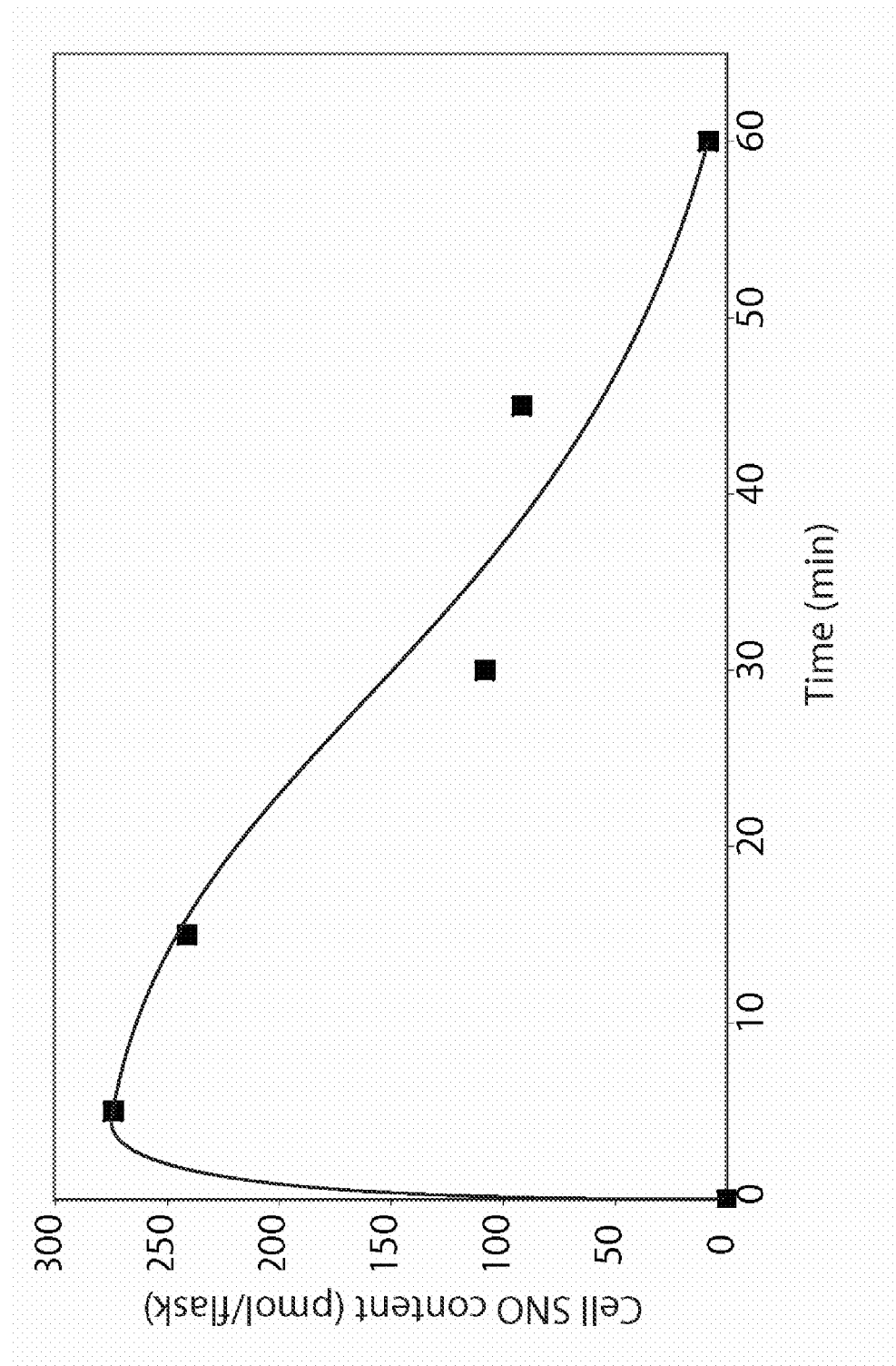
FIG. 14 is a graph showing the time course of S-nitrosation of cell proteins by MitoSNAP. Six 25 $cm^2$ flasks were seeded with C2C12 cells in 2 ml cell culture medium and incubated overnight. Then 5 μM MitoSNAP was added to each flask and they were incubated for the indicated times at 37° C. in the dark. The cells were then processed to measure S-nitrosated protein thiols. The experiment was repeated twice with similar results.

Incubation of C2C12 cells, an adherent mouse muscle cell line, with MitoSNAP led to the S-nitrosation of cell proteins reaching a maximum after 5-10 min FIG. 14. The extent of cell protein S-nitrosation by MitoSNAP after 5 min was considerably greater than that by SNAP (FIG. 11c), and the uncoupler FCCP greatly decreased S-nitrosation by MitoSNAP (FIG. 11c). These findings also signal that the S-nitrosation was $\Delta\psi$-dependent and due to mitochondrial accumulation of MitoSNAP. To assess this further, we isolated a mitochondria-enriched fraction from cells that had been incubated with MitoSNAP and found that the mitochondrial proteins were extensively S-nitrosated, a result that was decreased by abolishing the $\Delta\psi$ with FCCP (FIG. 11d). These data demonstrate the accumulation of MitoSNAP within mitochondria inside cells where it selectively S-nitrosates thiol proteins.

Figure 11:
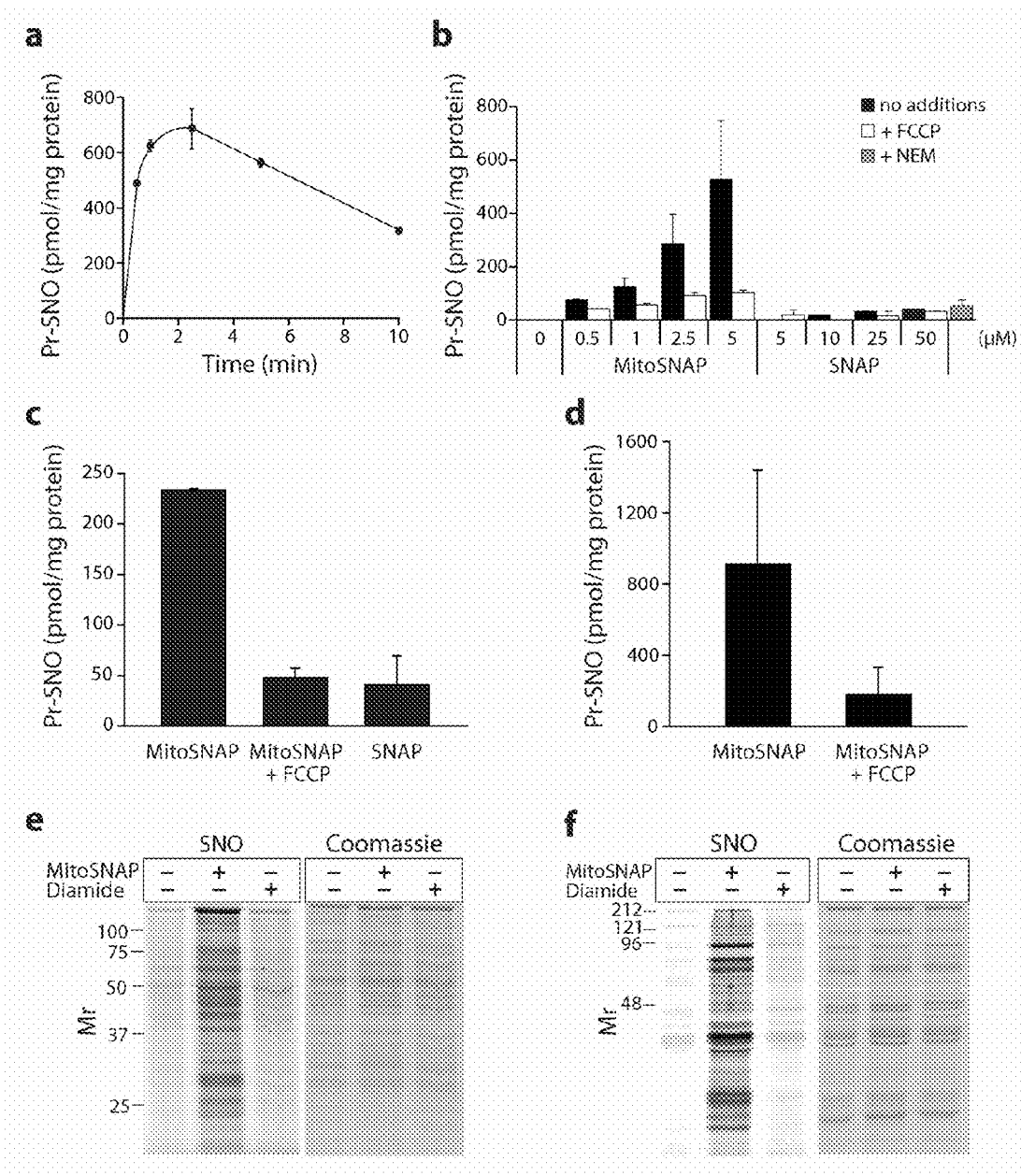
FIG. 11 is a series of graphs showing S-nitrosation of mitochondrial thiols by MitoSNAP. (a) Time course of S-nitrosation of mitochondrial proteins by MitoSNAP. Liver mitochondria (1 mg protein) were incubated in 1 ml KCl buffer supplemented with rotenone and succinate in the presence of 5 μM MitoSNAP. At various times mitochondria were treated with 10 mM N-ethylmaleimide (NEM), isolated by centrifugation and the S-nitrosothiol content assessed. Data are of a typical experiment showing means±range of duplicate samples for each time point, each measured in duplicate. The experiment was repeated twice. (b) S-nitrosation of mitochondrial proteins by different concentrations of MitoSNAP and SNAP. Aliquots of liver mitochondria were incubated with the indicated concentrations of MitoSNAP or SNAP for 2. min in the presence or absence of 500 nM FCCP and then assessed for S-nitrosothiol content as in (a). For the +NEM sample, 10 mM NEM was added to the mitochondria and 1 min later 5 μM MitoSNAP was added and incubated for a further 2.5 min. Data are of a typical experiment showing means±range of duplicate samples for each time point, each measured in duplicate. The experiment was repeated twice. (c) S-nitrosation of cellular protein thiols by MitoSNAP. C2C12 cells were preincubated for 5 min in 2 ml cell culture medium containing either 20 μM FCCP or DMSO carrier, then 5 μM MitoSNAP or SNAP was added. After further incubation for 5 min at 37° C. in the dark, the medium was removed and the content of S-nitrosated proteins was measured. Data are means±range of the duplicate determinations. Control incubations with 5 μM MitoNAP generated no RSNO. (d) S-nitrosation of a mitochondria-enriched cell subfraction. C2C12 cells were preincubated for 5 min in cell culture medium containing either 20 μM FCCP or dimethylsulfoxide (DMSO) carrier, then 5 μM MitoSNAP was added. After 5 min at 37° C. in the dark, the medium was removed and the cells were processed to isolate a mitochondria-enriched fraction and S-nitrosated protein was then determined Data are mean±sem of triplicate determinations (+MitoSNO1), or mean±range of duplicate determinations (+FCCP). (e & f) Visualisation of S-nitrosated mitochondrial proteins by copper/ascorbate-dependent labelling of thiols with a Cy3 fluorophore. Liver (e) or heart (f) mitochondria (1 mg protein) were incubated in 1 ml KCl buffer supplemented with rotenone and succinate in the presence of no additions, 10 μM MitoSNAP or 500 μM diamide for 5 min. S-nitrosated thiols were then selectively tagged with Cy3 maleimide and protein (10 μg) was then separated on a 12.5% SDS PAGE gel which was stained with coomassie blue and scanned for Cy3 fluorescence. The Cy3 fluorescence (SNO) and coomassie staining (coomassie) of each gel is shown. The experiment shows a typical result repeated twice.

The data shown in FIGS. 10 & 11 support the conclusion that $NO^\bullet$ production and S-nitrosation by MitoSNAP occurs selectively within mitochondria which in turn indicates that most MitoSNAP crosses the cytosol and enters mitochondria without being degraded by cytosolic GSH. The uptake of alkylTPP molecules into mitochondria within cells is rapid, equilibrating within 5-10 min (Ross, M. F. et al. Rapid and extensive uptake and activation of hydrophobic triphenylphosphonium cations within cells. *Biochem. J.* 411, 633-645 (2008)), and the rate limiting step is passage across the plasma membrane with rapid subsequent uptake into mitochondria (Ross, M. F. et al. Rapid and extensive uptake and activation of hydrophobic triphenylphosphonium cations within cells. *Biochem. J.* 411, 633-645 (2008) and Smith, R. A., Kelso, G. F., James, A. M. & Murphy, M. P. Targeting coenzyme Q derivatives to mitochondria. *Meth. Enzymol.* 382, 45-67 (2004)). Consequently, once through the plasma membrane, MitoSNAP should remain in the cytosol for a very short time before uptake into mitochondria. The rate of reaction of GSH with SNAP is $5.4 \, M^{-1}.s^{-1}$ (Hogg, N. The kinetics of S-transnitrosation-a reversible second-order reaction. *Anal. Biochem.* 272, 257-62 (1999)). While other pathways of MitoSNAP decay in the cytosol may also contribute, GSH is likely to be the major one and at a physiological GSH concentration of 5 mM the half-life for MitoSNAP in the cytosol should be ~25 s, giving plenty of time for MitoSNAP uptake into mitochondria. The greater pH of the mitochondrial matrix relative to the cytosol (8 vs 7.2) will also render mitochondrial thiols more reactive with MitoSNAP than those in the cytosol. These data suggest that most MitoSNAP is taken up from the cytosol into mitochondria without being extensively degraded by cytosolic GSH.

The interaction of MitoSNAP with mitochondrial thiol proteins is likely to initiate a dynamic process that may lead to other protein thiol modifications, such as disulfide formation, glutathionylation, sulfenylation or sulfenylamide formation, in addition to persistent S-nitrosation. To assess these, the content of reactive, solvent-exposed thiols on native liver mitochondrial proteins was measured. Under control conditions there were 43.2±3.8 nmol thiols/mg protein (mean±sem, n=3) and after incubation with 5 µM MitoSNAP for 5 min this did not change significantly (46.7±9.6; mean±sem, n=3). This is consistent with the finding that the maximum extent of mitochondrial protein S-nitrosation by 5 µM MitoSNAP (~500 pmol SNO/mg protein; FIG. 11) was only ~1% of the total number of protein thiols available. A small amount of MitoSNAP binding to mitochondrial thiol proteins through the formation of mixed disulfides was detectable by immunoblotting. Protein-glutathione mixed disulfides in mitochondria incubated with 5 µM MitoSNAP were not detectable, even though the thiol oxidant diamide led to extensive glutathionylation. Furthermore, incubation of mitochondria with 10 µM MitoSNAP for 10 min showed no loss of GSH or accumulation of GSSG. Under these conditions MitoSNAP does not lead to bulk changes in free protein thiol content or the GSH pool but instead causes the relatively persistent S-nitrosation of a small proportion of mitochondrial protein thiols.

To visualize these S-nitrosated mitochondrial proteins, we adapted a sensitive and robust extension of the "biotin switch technique" in which free thiols are first alkylated, then S-nitrosothiols are selectively degraded with ascorbate and copper to generate an exposed thiol that is then labelled with a fluorescently-tagged Cy3 maleimide (Wang, X., Kettenhofen, N.J., Shiva, S., Hogg, N. & Gladwin, M. T. Copper dependence of the biotin switch assay: modified assay for measuring cellular and blood nitrosated proteins. *Free Radic. Biol. Med.* 44, 1362-72 (2008)). The fluorescently-tagged proteins can then be sensitively detected by scanning the fluorescence of the gels. This technique showed that exposure of liver (FIG. 11e) or heart (FIG. 11f) mitochondria to Mito-SNAP led to the S-nitrosation of a large number of different proteins. In contrast, the thiol oxidant diamide did not label proteins, indicating that this technique is selective for SNOs over other thiol oxidative modifications. To summarize, MitoSNAP S-nitrosates a range of mitochondrial proteins, although only a small proportion of mitochondrial protein thiols are modified. This S-nitrosation persists in the presence of a reduced mitochondrial glutathione pool.

EXAMPLE 12

Effect of MitoSNAP on Complex I Activity and S-Nitrosation

Figure 15:
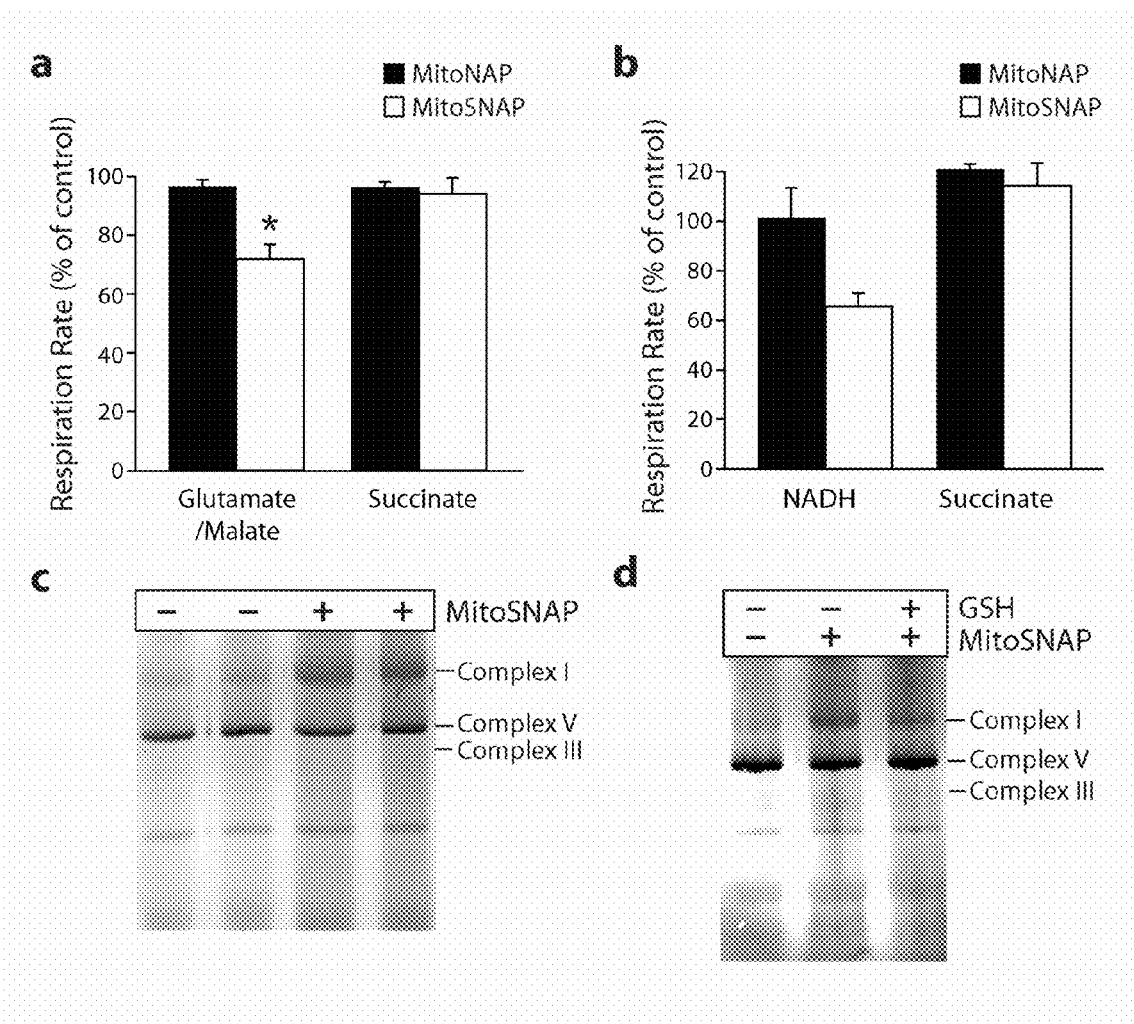
FIG. 15 is a series of graphs and pictures showing inhibition and S-nitrosation of complex I by MitoSNAP. (a) Effect of MitoSNAP on mitochondrial respiration. Heart mitochondria (1 mg protein/ml) were incubated in 1 ml KCl medium supplemented with 1 mM phosphate in an oxygen electrode with 5 mM glutamate and 5 mM malate, or succinate, and incubated with 10 μM MitoSNAP, 10 μM MitoNAP or carrier for 2 min (succinate) or 3 min (glutamate/malate), then 250 μM adenosine diphosphate (ADP) was added and the rate of respiration was measured. Respiration in the presence of MitoSNAP is expressed as a percentage of that with MitoNAP, and are means±sem from 3 separate mitochondrial preparations, each determined in triplicate; *p<0.05 by Student's paired t test. Respiration rates of control mitochondria on succinate and glutamate/malate were 140±8 and 92±5 nmol $O_2$/min/mg protein (means±sem, n=3), respectively. MitoNAP decreased control respiration on either substrate by about 3-4%. (b) Effect of MitoSNAP on respiration by mitochondrial membranes. Bovine heart mitochondrial membranes (0.25 mg protein/ml) were incubated in 1 ml KCl medium in an $O_2$ electrode at 37° C., and incubated with 75 µM MitoSNAP or MitoNAP, or ethanol carrier for 5 min in the presence or absence of rotenone, then 1 mM NADH or 10 mM succinate was added and the rate of respiration was measured. Data are expressed as respiration in the presence of MitoSNAP or MitoNAP as a percentage of the appropriate controls and are means±range of two separate experiments, each determined in triplicate. Respiration rates of control mitochondrial membranes on NADH or succinate were 198±33 and 56±3 nmol $O_2$/min/mg protein (means±range, n=2), respectively. (c) S-nitrosation of complex I by MitoSNAP. Bovine heart mitochondrial membranes (0.25 mg protein/ml) were incubated in duplicate in KCl medium at 37° C. with 75 µM MitoSNAP or carrier for 5 min. Then protein SNOs were labelled by maleimide-Cy3 and intact mitochondrial respiratory complexes were separated by BN-PAGE which was then scanned for Cy3 fluorescence. The location of respiratory complexes I, III and V on the gel was determined by immunoblotting. (d) Effect of GSH on S-nitrosation of complex I by MitoSNAP. Bovine heart mitochondrial membranes were incubated and processed as described for (c) except that after incubation±MitoSNAP the membranes were incubated±1 mM GSH for 15 min.

Complex I, the major entry point for electrons into the mitochondrial respiratory chain, can be S-nitrosated in vitro and in vivo, and this correlates with potentially important alterations to its activity. To evaluate the effect of MitoSNAP on complex I activity, we first examined the effect of Mito-SNAP on respiration in isolated heart mitochondria. Mito-SNAP inhibited respiration by about 30% relative to MitoNAP on the complex I-linked substrates glutamate/malate, but had very little effect on respiration with the complex II substrate succinate (FIG. 15a). As this inhibition occurred in the presence of high $O_2$ concentrations, did not vary as the $O_2$ concentration decreased and did not affect respiration on succinate, it was not due to NO• inhibition at cytochrome c oxidase (cf. FIG. 9) and MitoSNAP is either inhibiting NADH oxidation by complex I or affecting NADH supply. To distinguish between these, we next investigated respiration by fragments of heart mitochondrial membranes that directly oxidize both succinate and NADH (FIG. 15b) (Beer, S. M. et al. Glutaredoxin 2 Catalyzes the reversible oxidation and glutathionylation of mitochondrial membrane thiol proteins: implications for mitochondrial redox regulation and antioxidant defense. *J. Biol. Chem.* 279, 47939-51 (2004)). Results showed that MitoSNAP inhibited NADH respiration by about 35% while succinate was unaffected (FIG. 15b), strongly pointing to a specific effect of Mito-SNAP on complex I.

The inhibition of complex I by MitoSNAP in mitochondria occurred in the presence of a reduced GSH pool, and we next assessed the effect of GSH on the MitoSNAP inhibition of complex I in membranes. When MitoSNAP-treated mitochondrial membranes were isolated by centrifugation and resuspended in the presence of 1 mM GSH for 10-15 min the inhibition of NADH respiration by MitoSNAP was not reversed. Incubation of mitochondrial membranes with Mito-SNAP for 5 min under the conditions described in FIG. 15b led to the formation of 4.8±0.9 nmol protein SNOB/mg protein (mean±SD, n=4) and GSH treatment as above only decreased the SNO content by ~53%, thus the inhibition of complex I activity on MitoSNAP treatment may result from S-nitrosation that is relatively resistant to reversal by GSH. To confirm that complex I was S-nitrosated, we incubated mitochondrial membranes with MitoSNAP for 5 min and then blocked exposed thiols with NEM before selectively converting S-nitrosothiols to thiols by reaction with copper/ascorbate and then tagging them with the fluorescent label Cy3-maleimide as before[37]. Complex I was then isolated by blue native polyacrylamide gel electrophoresis (BN-PAGE) and this showed that complex I was S-nitrosated (FIG. 15c). (The reason for the intense but invariant labelling of complex V by Cy3-maleimide is unclear). Incubation of membranes with 1 mM GSH for 15 min did not reverse the S-nitrosation of complex I (FIG. 15d), therefore the continued inhibition of complex I by MitoSNAP even after incubation with GSH may be due to the persistence of S-nitrosation. To summarize, MitoSNAP persistently S-nitrosates complex I and this correlates with partial inhibition of its activity.

EXAMPLE 13

Vasorelaxation of Blood Vessels by MitoSNAP

Figure 16:
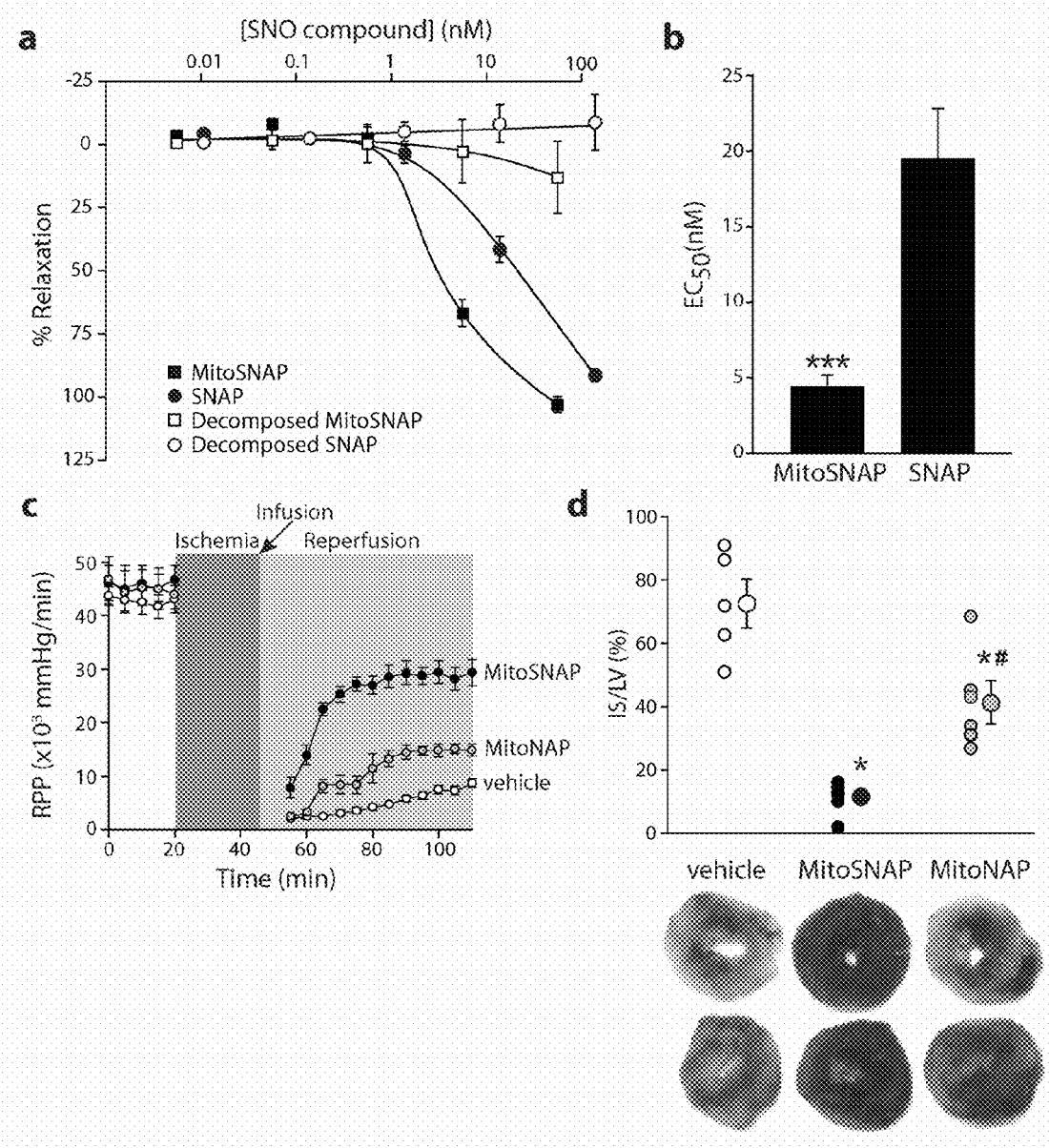
FIG. 16 is a series of graphs showing the vasodilatory and tissue protective effects of MitoSNAP. (a) Dose-response curves for the effect of MitoSNAP and related compounds on blood vessel relaxation. The effects of intact or decomposed MitoSNAP and SNAP on pre-contracted rat thoracic aorta mounted in a myograph were determined Data represent means±sem. For MitoSNAP n=8 from experiments on two independent rat aorta preparations. For decomposed MitoSNAP and SNAP experiments the data (n=4) are from one aorta preparation. (b) $EC_{50}$ for the effect of MitoSNAP and SNAP on blood vessel relaxation. The $EC_{50}$ values were determined from experiments shown in (a) above. ***p<0.001 by Student's unpaired t-test. (c & d) MitoSNAP protects against I/R injury in Langendorff-perfused mouse hearts. Hearts from C57BL6 mice were Langendorff perfused and subjected to 25 min global normothermic ischemia followed by 1 h of reperfusion. MitoSNAP or MitoNAP (100 nM final), or vehicle carrier, was added via an infusion port above the aortic cannula during reperfusion. Hearts were then stained with 2,3,5-triphenyltetrazolium chloride (TTC) to visualize infarct. (c) Protection of heart function by MitoSNAP during I/R injury. Left ventricular contractile function was recorded throughout the I/R protocol. Data show Rate Pressure Product (RRP, the heart rate multiplied by the left ventricular developed pressure (systolic minus diastolic). The arrow indicates where infusion with MitoSNAP or MitoNAP was initiated. Data are means±sem, n=6-7. (d) Decreased cardiac infarct size following infusion with MitoSNAP. Upper panel shows typical infarct staining in vehicle control, MitoNAP and MitoSNAP treated hearts. Pale white staining is necrotic infarct, while live tissue stains deep red. Lower panel shows quantitation of infarct size versus area at risk. Data are means±sem, n=6-7. *p<0.05 versus vehicle control group, #p<0.05 versus vehicle control group (ANOVA).
Figure 17:
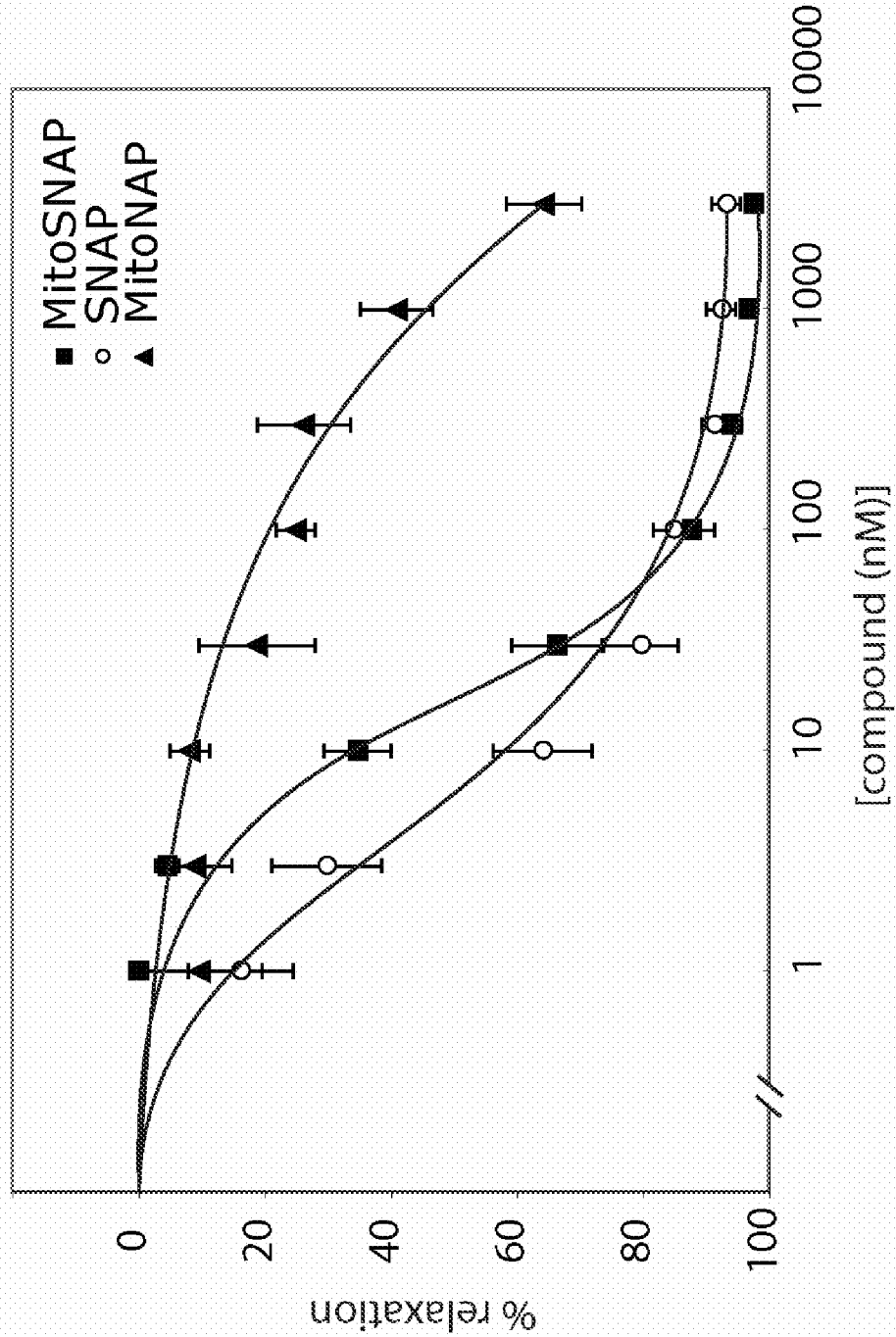
FIG. 17 is a graph showing vasorelaxation of endothelium-denuded rat small mesenteric artery preparations by MitoSNAP and SNAP. To measure vessel relaxation in endothelium-denuded rat mesenteric artery male Wistar rats (250-350 g) were anesthetized with sodium pentobarbitone (60 mg/kg ip Sagatal, Rhone Merieux, Harlow, Essex UK). The mesentery was removed and placed in ice-cold, gassed (95% $O_2$/5% $CO_2$) Krebs-Henseleit buffer. Segments (2 mm in length, 250-350 µm in diameter) of third order branches of the superior mesenteric artery were removed, endothelium was removed by rubbing the intima with a human forearm hair and mounted in a Mulvany-Halpern myograph (Model 500A, JP trading, Aarhus, Denmark) as described[2]. Vessels were maintained at 37° C. in Krebs-Henseleit solution containing indomethacin (10 µM) and bubbled with 95% $O_2$/5% $CO_2$ and were allowed to equilibrate under zero tension for 60 min. After equilibration vessels were normalized to a tension equivalent that generated at 90% of the diameter of the vessel at 100 mm Hg[3]. Vessels were precontracted with methoxamine and then sequential cumulative additions of test compounds were made to relax the vessels shielded from direct light. Relaxation of muscle tone are expressed as a percentage of relaxation of the initial tone. Data are means of four determination of MitoNAP and MitoSNAP and of 6 for SNAP. Data from the dose-response curves were fitted to a logistic curve, with the following parameters: MitoSNAP, $EC_{50}$=16.5±1.1 nM, max. relaxation of induced tone=96±1% and slope function (Hill slope)=1.3±0.1; SNAP, $EC_{50}$=5.2±0.5 nM, max. relaxation of induced tone=92±2% and slope function (Hill slope)=1.0±0.1. The data for MitoNAP did not fit to a logistic curve.

The uptake of MitoSNAP into mitochondria within vascular tissue and the subsequent NO• release may make MitoSNAP a potent vasodilator. This was evaluated by determining whether MitoSNAP could relax the smooth muscle in blood vessel walls. Sections of rat thoracic aorta were mounted in a myograph, pre-contracted and then cumulative amounts of MitoSNAP were added (FIG. 16a). This showed that MitoSNAP was a vasodilator, and that pretreating MitoSNAP to degrade its SNO moiety rendered it ineffective (FIG. 16a). In this assay MitoSNAP was a more potent vasodilator than SNAP with an $EC_{50}$ of 4.5 nM compared to 19.5 nM for SNAP (FIG. 16b). MitoSNAP was also an effective vasodilator in endothelium-denuded rat resistance mesenteric arteries (FIG. 17). These data demonstrate MitoSNAP is an effective endothelium-independent vasodilator acting via NO• release within tissues.

EXAMPLE 14

MitoSNAP Protects Against Cardiac Ischemia-Reperfusion Injury (Ex Vivo)

There is considerable evidence pointing to mitochondrial damage during the reperfusion phase of cardiac ischemia-reperfusion (I/R) injury. This damage can be decreased by ischemic preconditioning (IPC), whereby previous exposure to short periods of I/R protects against subsequent I/R injury (Burwell, L. S. & Brookes, P. S. Mitochondria as a target for the cardioprotective effects of nitric oxide in ischemia-reperfusion injury. *Antioxid. Redox Signal.* 10, 579-99 (2008)). While the nature of the protection afforded by IPC remains obscure, mitochondrial NO• and $NO_2^-$ metabolism may play a role. As MitoSNAP is rapidly taken up by mitochondria within cells where it S-nitrosates mitochondrial thiol proteins, including complex I (FIGS. 11 & 15), it may also protect heart mitochondria from I/R damage. Therefore we determined if MitoSNAP could decrease I/R injury in a mouse heart Langendorff model (FIGS. 16c & d). When mouse hearts were Langendorff perfused and subjected to 25 min global normothermic ischemia followed by 1 h of normoxic reperfusion there was extensive heart damage, as indicated by the decrease in heart function (rate pressure product, RPP) (FIG. 16c) and by the large infarcted area (FIG. 16d). When MitoSNAP (100 nM, final) was perfused into the heart during reperfusion there was significantly less heart damage, as indicated by the better recovery of heart function (FIG. 16c) and the decrease in infarct size (FIG. 16d), compared to the control and MitoNAP-infused hearts. Infusion of 100 nM MitoNAP during the reperfusion phase was also slightly protective, but was far less so than MitoSNAP (FIGS. 16c & d), indicating that uptake of the intact NO• donor into mitochondria was required for full protection.

Figure 18:
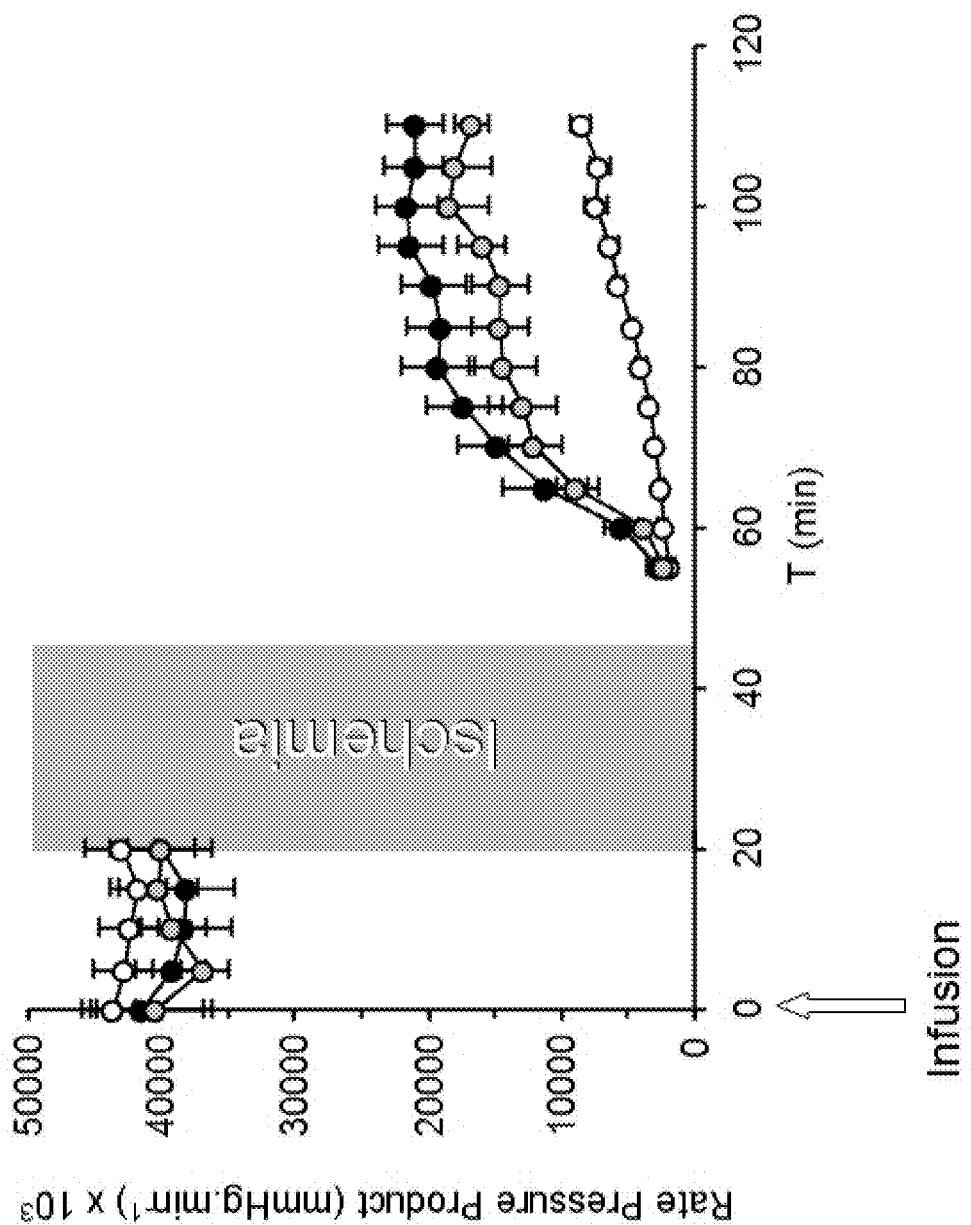
FIG. 18 is a graph showing the effect of pre-ischemic administration of MitoSNAP or MitoNAP on recovery of heart function (rate pressure product) from IR injury. Experiments were carried out exactly as described in FIGS. 16c & 16d, except that MitoSNO1 or MitoNAP were infused into the heart for 20 min, followed by a 2 min wash-out period, prior to the onset of ischemia. White symbols=vehicle control, black symbols=MitoSN01, gray symbols=MitoNAP. Data are means±sem, n≥6.

The small protective effect of MitoNAP may be due to the antioxidant effect of accumulating the N-acetylpenicillamine group, or the TPP cation, in mitochondria. A small degree of protection was also observed when MitoSNAP was delivered before the I/R injury, similar to that observed with the parent compound MitoNAP (FIG. 18). The rapid metabolism of MitoSNAP in cells may be such that pre-treatment does not induce S-nitrosation at the critical time point of reperfusion required for maximal protection and the mild protection seen during pre-treatment is therefore likely to be due to residual antioxidant activity of the N-acetylpenicillamine function on MitoNAP. These findings support the S-nitrosation of mitochondrial proteins as a therapeutic strategy in minimizing I/R injury and is also consistent with the S-nitrosation of mitochondrial proteins such as complex I contributing to both IPC and to the protection of mitochondrial function by NO• and $NO_2^-$ during I/R injury.

EXAMPLE 15

MitoSNAP Protects Against Cardiac Ischemia-Reperfusion Injury (In Vivo)

Following anesthesia (Avertin, 2,2,2-tribromoethanol, 0.5 mg/kg IP) mice were intubated with a 20 gauge PE catheter which was connected to a rodent ventilator (Harvard Mini-Vent, 120 cycles/min., 0.3 ml tidal volume). A thoracotomy was performed and the left anterior descending coronary artery (LAD) was then ligated and occluded with a 9-0 proline suture for 30 min. MitoSNAP or MitoNAP (100 ng/kg) were dissolved in 0.9% NaCl saline (final volume 50 µl) and then administered 5 min prior to reperfusion into left ventricle (LV) using 30G½ needle. Reperfusion was initiated by removing the suture. The chest and skin were sutured closed, the endotracheal tube removed and the animal returned to its cage to recover. After 24 hrs. the animal was re-anesthetized, the LAD re-ligated, and Evans' blue dye (1.0% w/v, 1.5 ml) perfused via the LV. The heart was removed and cut transversely into 5 sections, which were incubated in 1.0% 2,3,5-triphenyltetrazolium chloride, 37° C. for 10 min. The area at risk (AR) and infarct zone were indicated by the areas unstained with Evans' blue and TTC, respectively. Slices were scanned and infarct/AR ratios determined with NIH ImageJ software. The results are shown in FIG. 19.

Industrial Applicability

The compounds of the invention provide a delivery system for NO directly into the mitochondria. The compounds are selectively taken up by the mitochondria driven by the membrane potential. Selective delivery of NO in the mitochondria allows targeting of local NO-sensitive variables, such as the inhibition of respiration. The compounds of the invention can also S-nitosylate proteins present in the mitochondria. Conventional NO donors produce NO throughout the cell and affect a great number of NO signaling pathways.

The compounds of the invention are of use in the treatment of conditions which are affected by mitochondrial respiration such as ischaemia-reperfusion injury. They are also able to inhibit angiogenesis and therefore are of use in the treatment and prevention of tumour growth and/or metastasis.

What we claim is:

1. A compound comprising a lipophilic cation linked by a linker group to a thionitrite moiety, wherein the compound has the structure of the general formula I and the lipophilic cation is capable of mitochondrially targeting the thionitrite moiety,

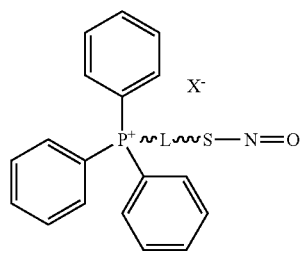

(I)

wherein L is the linker group and X_ is an anion, and the linker group is selected from the group consisting of
- (a) $(C_{1-30})$ alkylene,
- (b) $(C_{1-x})$ alkylene-NR—$(C_{1-y})$ alkylene, wherein R is H, alkyl, or aryl,
- (c) $(C_{1-x})$ alkylene-NR—C(=O)—$(C_{1-y})$ alkylene, wherein R is H, alkyl, or aryl,
- (d) $(C_{1-x})$ alkylene-C(=O)—NR—$(C_{1-y})$ alkylene, wherein R is H, alkyl, or aryl,
- (e) $(C_{1-x})$ alkylene-O—$(C_{1-y})$alkylene,
- (f) $(C_{1-x})$ alkylene-O—C(=O)—$(C_{1-y})$ alkylene,
- (g) $(C_{1-x})$ alkylene-S—$(C_{1-y})$ alkylene, or
- (h) $(C_{1-x})$ alkylene-aryl$(C_{1-y})$ alkylene, wherein x +y =30; and wherein each alkylene is optionally substituted with one or more functional groups independently selected from the group consisting of hydrogen, alkyl, cycloalkyl, alkenyl, alkynyl, haloalkyl, aryl, aminoalkyl, hydroxyalkyl, alkoxyalkyl, alkylthio, alkylsulfinyl, alkylsulfonyl, carboxyalkyl, cyano, oxy, amino, alkylamino, aminocarbonyl, alkoxycarbonyl, aryloxycarbonyl, alkylaminocarbonyl, arylaminocarbonyl, aralkylaminocarbonyl, alkylcarbonylamino, arylcarbonylamino, aralkylcarbonylamino, alkylcarbonyl, heterocyclocarbonyl, aminosulfonyl, alkylaminosulfonyl, alkylsulfonyl, and heterocyclosulfonyl, or the substituent groups of adjacent carbon atoms in the linker group can be taken together with the carbon atoms to which they are attached to form a carbocycle or a heterocycle.

2. A compound of claim 1 wherein the anion is an anion derived from an acid selected from the group comprising hydrochloric, hydrobromic, hydroiodic, sulfuric, sulfurous, nitric, nitrous, phosphoric, phosphorous, alkylsulfonic or arylsulfonic acid.

3. A compound of claim 1 wherein the compound is of formula (II)

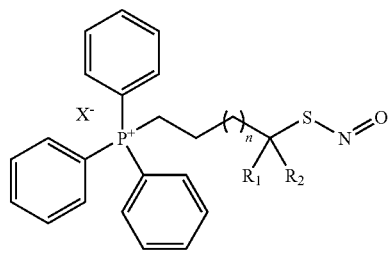

(II)

wherein n is from 0 to 27X, is an anion and $R_1$ and $R_2$ are independently selected from the group comprising hydrogen, alkyl and aryl.

4. A compound of claim 1 wherein the compound is of formula (III)

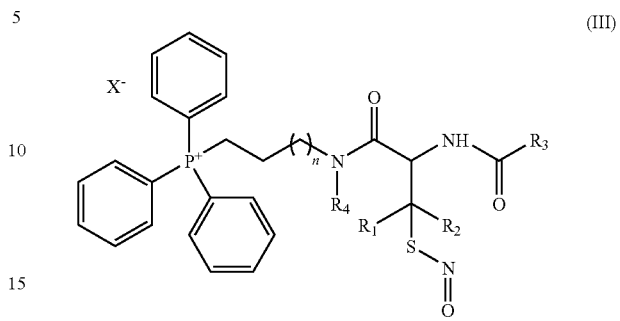

(III)

wherein n is from 0 to 27, $X^-$ is an anion and $R_1$, $R_2$, $R_3$ and $R_4$ are independently selected from the group comprising hydrogen, alkyl and aryl.

5. A compound of claim 1 wherein the compound is of formula (IV)

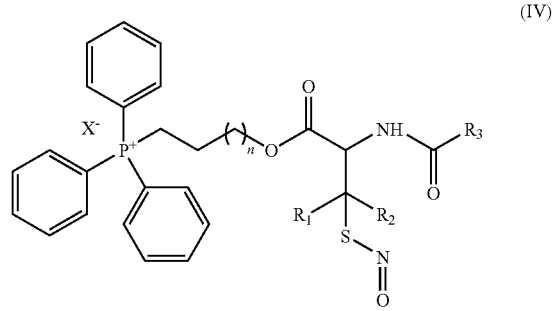

(IV)

wherein n is from 0 to 27X, is an anion and $R_1$, $R_2$ and $R_3$ are independently selected from the group comprising hydrogen, alkyl and aryl.

6. A compound of claim 1 wherein the compound is formula (V)

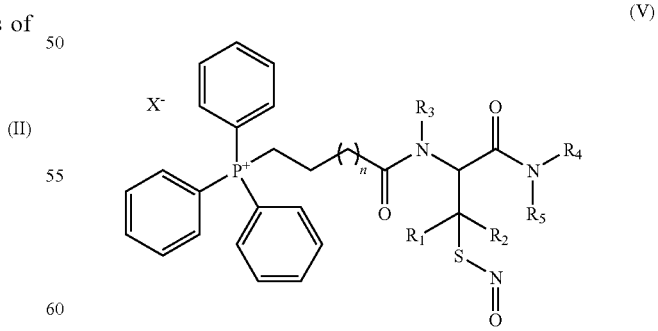

(V)

wherein n is from 0 to 27X, is an anion and $R_1$, $R_2$, $R_3$, $R_4$ and $R_5$ are independently selected from the group comprising hydrogen, alkyl and aryl.

7. A compound of claim 1 wherein the compound is of formula (VI)

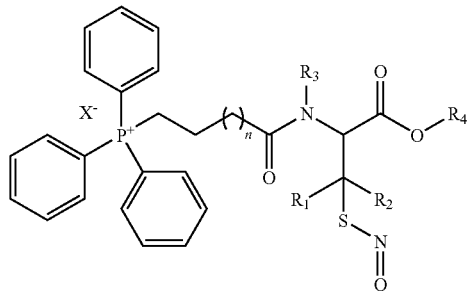

(VI)

wherein n is from 0 to 27X, is an anion and $R_1$, $R_2$, $R_3$ and $R_4$ are independently selected from the group comprising hydrogen, alkyl and aryl.

8. A pharmaceutical composition comprising a therapeutically effective amount of a compound of claim 1 with one or more pharmaceutically acceptable excipients, carriers or diluents.

9. A method for generating NO in the mitochondria of a subject comprising administering to the subject, a therapeutically effective amount of a compound of claim 1 or a pharmaceutical composition comprising same.

10. A method for S-nitrosylating proteins in the mitochondria of a subject comprising administering to the subject, a therapeutically effective amount of a compound of claim 1 or a pharmaceutical composition comprising same.

11. A compound selected from the group comprising:

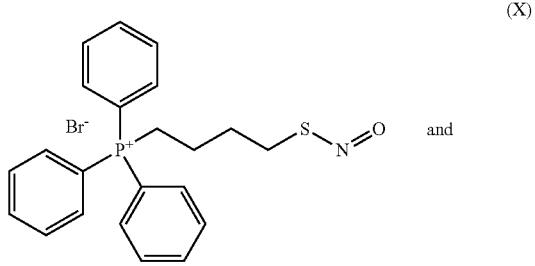

(X)

and

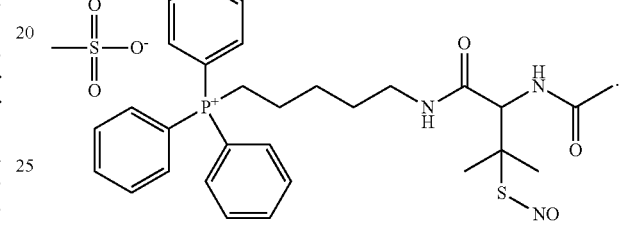

(XI)

* * * * *

UNITED STATES PATENT AND TRADEMARK OFFICE
CERTIFICATE OF CORRECTION

PATENT NO. : 9,045,505 B2
APPLICATION NO. : 12/732909
DATED : June 2, 2015
INVENTOR(S) : Robin Andrew James Smith and Michael Patrick Murphy Page 1 of 1

It is certified that error appears in the above-identified patent and that said Letters Patent is hereby corrected as shown below:

In the claims

In claim 1:
Insert: (i) --$X^-$-- after "group and" on line 14, column 45; and (ii) a space after "$(C_{1-y})$" on line 24, column 45.
Delete: "$X\_$" after "group and" on line 14, column 45.

In claim 3:
Insert: --27, $X^-$-- after "from 0 to" on line 65, column 45.
Delete: "27X," after "from 0 to" on line 65, column 45.

In claim 5:
Insert: --27, $X^-$-- after "from 0 to" on line 42, column 46.
Delete: "27X," after "from 0 to" on line 42, column 46.

In claim 6:
Insert: --27, $X^-$-- after "from 0 to" on line 65, column 46.
Delete: "27X," after "from 0 to" on line 65, column 46.

In claim 7:
Insert: --27, $X^-$-- after "from 0 to" on line 18, column 47.
Delete: "27X," after "from 0 to" on line 18, column 47.

Signed and Sealed this
First Day of December, 2015

Michelle K. Lee
*Director of the United States Patent and Trademark Office*